US012692504B2

(12) United States Patent
Mairhofer

(10) Patent No.: US 12,692,504 B2
(45) Date of Patent: Jul. 28, 2026

(54) CONTINUOUS BIOPRODUCTION BY DECOUPLING GROWTH AND PRODUCTION

(71) Applicant: ENGENES BIOTECH GMBH, Vienna (AT)

(72) Inventor: Juergen Mairhofer, Vienna (AT)

(73) Assignee: enGenes Biotech GmbH, Vienna (AT)

( * ) Notice: Subject to any disclaimer, the term of this patent is extended or adjusted under 35 U.S.C. 154(b) by 942 days.

(21) Appl. No.: 17/787,493

(22) PCT Filed: Dec. 20, 2020

(86) PCT No.: PCT/EP2020/087354
§ 371 (c)(1),
(2) Date: Jun. 20, 2022

(87) PCT Pub. No.: WO2021/123402
PCT Pub. Date: Jun. 24, 2021

(65) Prior Publication Data
US 2023/0167457 A1     Jun. 1, 2023

(30) Foreign Application Priority Data
Dec. 20, 2019     (LU) ....................................... 101582

(51) Int. Cl.
*C12N 15/70* (2006.01)
*C12M 1/00* (2006.01)
*C12M 1/06* (2006.01)
*C12P 5/00* (2006.01)

(52) U.S. Cl.
CPC ............. *C12N 15/70* (2013.01); *C12M 23/58* (2013.01); *C12M 27/02* (2013.01); *C12P 5/007* (2013.01)

(58) Field of Classification Search
CPC ... A61K 8/64; C12N 1/20; C12N 7/00; C12N 15/74; C12N 15/11; C12P 23/00; C12P 2203/00; C12P 5/007; C12P 7/6427; C12M 21/14; C12M 23/58; C12M 27/02
USPC ....................................................... 435/69.1
See application file for complete search history.

(56) References Cited

U.S. PATENT DOCUMENTS

2018/0282737 A1     10/2018  Mairhofer
2019/0367930 A1     12/2019  Li et al.

FOREIGN PATENT DOCUMENTS

WO         2016174195 A1    11/2016

OTHER PUBLICATIONS

Whisstock et al., (Quarterly Reviews of Biophysics 2003, vol. 36 (3): 307-340.*
Devos et al., (Proteins: Structure, Function and Genetics, 2000, vol. 41: 98-107.*
Witkowski et al., (Biochemistry 38:11643-11650, 1999.*
Kisselev L., (Structure, 2002, vol. 10: 8-9.*
Cámara B, et al., (2010) "T7 phage protein Gp2 inhibits the *Escherichia coli* RNA polymerase by antagonizing stable DNA strand separation near the transcription start site", Proc Natl Acad Sci USA, 107:2247-2252.
Rai N, Huynh L, Kim M, Tagkopoulos I., "Population collapse and adaptive rescue during long-term chemostat fermentation", Biotechnol Bioeng. Mar. 2019; 116(3):693-703. doi: 10.1002/bit.26898. Epub Jan. 16, 2019. PMID: 30536368.
Stargardt P, Feuchtenhofer L, Cserjan-Puschmann M, Striedner G, Mairhofer J., "Bacteriophage Inspired Growth-Decoupled Recombinant Protein Production in *Escherichia coli*.", ACS Synth Biol. Jun. 19, 2020;9(6):1336-1348. doi: 10.1021/acssynbio.0c00028. Epub May 7, 2020. PMID: 32324989.
Lemmerer, M, Mairhofer, J, Lepak, A, Longus, K, Hahn, R, Nidetzky, B., "Decoupling of recombinant protein production from *Escherichia coli* cell growth enhances functional expression of plant Leloir glycosyltransferases", Biotechnology and Bioengineering. 2019; 116: 1259-1268. https://doi.org/10.1002/bit.26934.
Gagnon M, Nagre S, Wang W, Coffman J, Hiller GW., "Novel, linked bioreactor system for continuous production of biologics", Biotechnol Bioeng. Aug. 2019;116(8):1946-1958. doi: 10.1002/bit.26985. Epub May 23, 2019. PMID: 30950040.
Wolf, M.K.F., (2018) "Development and Optimization fo Mammalian Cell Perfusion Cultures for Continuous Biomanufacturing", Doctoral Thesis, Diss. Eth No. 25284, ETH Zurich Research Collection, 245 pages.

* cited by examiner

*Primary Examiner* — Tekchand Saidha
*Assistant Examiner* — Mohammad Y Meah
(74) *Attorney, Agent, or Firm* — Mueting Raasch Group

(57)     ABSTRACT

The present invention is in the field of recombinant biotechnology, in particular in the field of protein expression and nucleotide production. The invention generally relates to systems and processes that are suitable or comprise a two stage production process, in which the growth of the bacterial host cell is spatiotemporally separated from the production of the protein or nucleic acid of interest. Accordingly, the present invention relates to a system and a process for use in continuous production of a protein of interest or a nucleotide of interest by a bacterial host cell.

15 Claims, 11 Drawing Sheets

Specification includes a Sequence Listing.

Seed reactor for biomass production SpA / uninduced
Cell dry mass (CDM) BL21(DE3) vs enGenes-X-press Production reactor / induced Cell dry mass (CDM) and productivity of secreted SpA

CONTINUOUS BIOPRODUCTION BY DECOUPLING GROWTH AND PRODUCTION

PRIORITY CLAIM

This application claims priority to International Application No. PCT/EP2020/087354, filed Dec. 20, 2020, which claims priority to Luxembourg Application No. 101582, filed Dec. 20, 2019, wherein the contents of said applications are incorporated herein by reference in their entireties. Also, the entire contents of the ASCII text file entitled "IPM0140US_Sequence_Listing.txt" created on Jun. 19, 2022, having a size of 32 kilobytes is incorporated herein by reference.

TECHNICAL FIELD OF THE INVENTION

The present invention is in the field of recombinant biotechnology, in particular in the field of nucleotide and protein expression. The invention generally relates to systems and processes that are suitable for or comprise a two stage production process, in which the growth of the bacterial host cell is spatially separated from the production of the protein or nucleic acid or of interest to allow a continuous production.

BACKGROUND

Production of proteins of interest (POI) or nucleotides of interests has been accomplished with many prokaryotic hosts. The most prominent examples are bacteria like *Escherichia coli, Bacillus subtilis, Pseudomonas fluorescens, Streptomyces griseus*, or *Corynebacterium glutamicum*. A great number of biological pharmaceuticals (e.g. antibodies or functional fragments thereof) have been produced in the last decade and an increasing number is nearing approval for use in humans but their efficient production remains a challenging task. Therapeutically active doses are often in the order of milligram (mg) per administration. Thus, considerable amounts of protein are needed as active ingredients, making an efficient and cost-effective production worthwhile.

Bacterial cell expression systems have long been, and still are, one of the major tools for production of these types of molecules. The key objective of process optimization is to achieve a high yield of product having the required quality at the lowest possible cost, which is often determined by the properties of a specific expression construct or system. Very often, a batch process is used for protein expression. A batch process however is labour-intensive because the bioreactors require constant surveillance and must be cleaned thoroughly after each production. While the bioreactors are cleaned, production cannot take place making batch processes inefficient.

By applying a continuous expression system instead of a batch process, these various problems associated with a batch process can be overcome. However, also in a continuous process, high-level recombinant protein expression may overwhelm the metabolic capacity of a host cell and consequently leads to plasmid loss, reduced oxygen transfer, generation of toxic by-products, formation of inclusion bodies, and/or triggering of a stress response which often impairs efficient protein production. It is also known that sometimes high expression of an mRNA encoding a protein of interest does not necessarily lead to high amounts of the protein.

Different approaches have been taken by scientists to deal with these problems, also for continuous expression systems. However, continuous expression systems that ensure the genetic stability of the host cells for a longer period of time to express proteins or nucleic acids of interest have not been described yet. Since a continuous expression system has many advantages including higher yield at lower costs, e.g. an improved space-time-yield (S-T-Y), there still is a need for a continuous production of proteins or nucleotides of interests in microbial host cells. Accordingly, the technical problem underlying the present invention is to comply with this need, e.g. by developing continuous manufacturing processes with an improved time-span of significant expression levels.

SUMMARY OF THE INVENTION

The present invention provides as a solution to the technical problem new means and methods to increase the yield and/or productivity defined as yield/time but also as productivity per volume of the culture of recombinant protein or nucleotide production by applying a continuous expression system and process, which are simple and efficient and suitable for use in industrial methods. In this continuous expression, the growth of the microbial or bacterial host cells is spatially separated from the production of the protein or nucleotide of interest ("growth decoupling"). These means and methods are described herein, illustrated in the Examples, and reflected in the claims.

Accordingly, the present invention relates to a system for use in continuous production of a protein of interest or a nucleotide of interest by a bacterial host cell, wherein the bacterial host cell comprises under the control of a first inducible promoter a nucleotide sequence encoding a protein from a phage which inhibits growth of said bacterial host cell, comprising (a) a seed reactor comprising said bacterial host cell in an uninduced state with respect to the nucleotide sequence encoding a protein from a phage which inhibits growth of said bacterial host cells, the seed reactor having at least one inlet and at least one outlet, and (b) at least one production reactor comprising said bacterial host cells in an induced state with respect to the nucleotide sequence encoding a protein from a phage which inhibits growth of said bacterial host cells, each production reactor having at least one inlet and at least one outlet, wherein an inlet of the production reactor is connected to an outlet of the seed reactor.

In one embodiment of the system of the invention, the bacterial host cell comprises a nucleotide encoding the protein of interest or the nucleotide of interest.

In one embodiment of the system of the invention, the protein of interest or the nucleotide of interest is produced in the at least one production reactor.

In one embodiment of the system of the invention, said nucleotide of interest encodes one or more proteins of interest.

In one embodiment of the system of the invention, said nucleotide is a nucleic acid molecule.

In one embodiment of the system of the invention, said nucleic acid molecule is a plasmid, minichromosome, or RNA.

In one embodiment of the system of the invention, said nucleotide of interest or said nucleotide encoding the protein of interest is under the control of a second inducible promoter or under the control of a constitutive promoter.

In one embodiment of the system of the invention, the promoter of said heterologous nucleotide of interest is recognized by a RNA polymerase which is heterologous for said bacterial host cell, said heterologous RNA polymerase is encoded by a nucleotide sequence comprised by said bacterial host cell.

In one embodiment of the system of the invention, said RNA polymerase is bacteriophage T3 RNA polymerase, T7 bacteriophage RNA polymerase, engineered orthogonal T7 RNA polymerase, bacteriophage SP6 RNA polymerase or bacteriophage Xp10 RNA polymerase.

In one embodiment of the system of the invention, said nucleotide sequence encoding said RNA polymerase is under the control of a third inducible promoter or under the control of a constitutive promoter.

In one embodiment of the system of the invention, said first, second or third inducible promoter is regulated by arabinose, IPTG, tryptophan, xylose, lactose, rhamnose, phosphate, propionate, benzoic acid, phage lambda cl protein or heat.

In one embodiment of the system of the invention, said first, second or third promoter are different.

In one embodiment of the system of the invention, said bacterial host cell has a non-functional arabinose operon.

In one embodiment of the system of the invention, said bacterial host cell is *E. coli*, preferably *E. coli* B-lineage.

In one embodiment of the system of the invention, growth is inhibited by inhibiting transcription, DNA-replication and/or cell division.

In one embodiment of the system of the invention, said phage protein is (i) a protein which inhibits bacterial host cell RNA polymerase, wherein said protein is
   (a) a protein having the amino acid sequence shown in Seq Id No: 1 or a fragment thereof which inhibits bacterial host cell RNA polymerase; or
   (b) a protein having an amino acid sequence which has an identity of 40% or more to the amino acid sequence shown in Seq Id No: 1 and which inhibits bacterial host cell RNA polymerase;

(ii) a protein which inhibits bacterial host cell RNA polymerase, wherein said protein is
   (a) a protein having the amino acid sequence shown in Seq Id No: 2 or a fragment thereof which inhibits bacterial host cell RNA polymerase; or
   (b) a protein having an amino acid sequence which has an identity of 40% or more to the amino acid sequence shown in Seq Id No: 2 and which inhibits bacterial host cell RNA polymerase;

(iii) a protein which phosphorylates bacterial host cell RNA polymerase, wherein said protein is
   (a) a protein having the amino acid sequence shown in Seq Id No: 3 or a fragment thereof which phosphorylates bacterial host cell RNA polymerase; or
   (b) a protein having an amino acid sequence which has an identity of 40% or more to the amino acid sequence shown in Seq Id No: 3 and which phosphorylates bacterial host cell RNA polymerase;

(iv) a protein which inhibits bacterial host cell DNA replication, wherein said protein is
   (a) a protein having the amino acid sequence shown in Seq Id No: 4 or a fragment thereof which inhibits bacterial host cell DNA replication; or
   (b) a protein having an amino acid sequence which has an identity of 40% or more to the amino acid sequence shown in Seq Id No: 4 and which inhibits bacterial host cell DNA replication;

(v) a protein which inhibits bacterial host cell DNA replication, wherein said protein is
   (a) a protein having the amino acid sequence shown in Seq Id No: 5 or a fragment thereof which inhibits bacterial host cell DNA replication; or
   (b) a protein having an amino acid sequence which has an identity of 40% or more to the amino acid sequence shown in Seq Id No: 5 and which inhibits bacterial host cell DNA replication; or (vi) a protein which inhibits bacterial host cell DNA replication, wherein said protein is
   (a) a protein having the amino acid sequence shown in Seq Id No: 6 or a fragment thereof which inhibits bacterial host cell DNA replication; or
   (b) a protein having an amino acid sequence which has an identity of 40% or more to the amino acid sequence shown in Seq Id No: 6 and which inhibits bacterial host cell DNA replication;

(vii) a protein which inhibits bacterial host cell RNA polymerase, wherein said protein is
   (a) a protein having the amino acid sequence shown in Seq Id No: 7 or a fragment thereof which inhibits bacterial host cell RNA polymerase; or
   (b) a protein having an amino acid sequence which has an identity of 40% or more, such as 50%, 60%, 70%, 80% or 90% to the amino acid sequence shown in Seq Id No: 7 and which inhibits bacterial host cell RNA polymerase;

(viii) a protein which causes host transcription shut-off, wherein said protein is
   (a) a protein having the amino acid sequence shown in Seq Id No: 8, 9, 10, 11, 12, 13, 14 or a fragment thereof which causes host transcription shut-off; or
   (b) a protein having an amino acid sequence which has an identity of 40% or more, such as 50%, 60%, 70%, 80% or 90% to the amino acid sequence shown in Seq Id No: 8, 9, 10, 11, 12, 13 or 14 and which causes host transcription shut-off; or (ix) a protein which inhibits bacterial host cell RNA polymerase, wherein said protein is
   (a) a protein having the amino acid sequence shown in Seq Id No: 17 or a fragment thereof which inhibits bacterial host cell RNA polymerase; or
   (b) a protein having an amino acid sequence which has an identity of 40% or more to the amino acid sequence shown in Seq Id No: 17 and which inhibits bacterial host cell RNA polymerase.

In one embodiment of the system of the invention, the bacterial host cell is cultured in an uninduced state with respect to the nucleotide sequence encoding a protein from a phage which inhibits growth of said bacterial host cell in the seed reactor for biomass production.

In one embodiment of the system of the invention, the bacterial host cell is cultured in an induced state with respect to the nucleotide sequence encoding a protein from a phage which inhibits growth of said bacterial host cell in the production reactor for production of said nucleotide sequence of interest by said bacterial host cells.

In one embodiment of the system of the invention, the system further comprises (c) a means for operating the seed and production reactors as linked chemostats or turbidostats.

In one embodiment of the system of the invention, the seed reactor outflow serves as inflow to the production reactor.

In one embodiment of the system of the invention, the seed reactor does not comprise or does not essentially comprise an inducer for the first inducible promoter.

In one embodiment of the system of the invention, at least one of the at least one production reactor comprises an inducer for the first inducible promoter.

In one embodiment of the system of the invention, at least one of the at least one of the at least one production reactor comprises an inducer for the second inducible promoter.

In one embodiment of the system of the invention, the first inducible promoter and the second inducible promoter can be induced by the same inducer.

In one embodiment of the system of the invention, the seed reactor comprises a means for regulating pH.

In one embodiment of the system of the invention, the seed reactor comprises a means for regulating dissolved oxygen.

In one embodiment of the system of the invention, the seed reactor comprises a means for regulating temperature.

In one embodiment of the system of the invention, the seed reactor comprises a gas inlet and a gas outlet and a means for regulating the gas flow.

In one embodiment of the system of the invention, the at least one production reactor comprises a means for regulating pH.

In one embodiment of the system of the invention, the at least one production reactor comprises a means for regulating dissolved oxygen.

In one embodiment of the system of the invention, the at least one production reactor comprises a means for regulating temperature.

In one embodiment of the system of the invention, the at least one production reactor comprises a gas inlet and a gas outlet and a means for regulating the gas flow.

In one embodiment of the system of the invention, the at least one production reactor comprises a biomass sensor.

In one embodiment of the system of the invention, the system comprises a first feed container containing a first feed medium comprising a carbon source, wherein the first feed container is operably connected to an inlet of the seed reactor, wherein the system preferably comprises means for regulating feed flow from the first feed container to the seed reactor.

In one embodiment of the system of the invention, the system comprises second feed container containing a second feed medium comprising a carbon source, wherein the second feed container is operably connected to an inlet of the at least one production reactor, wherein the system preferably comprises means for regulating feed flow from the second feed container to the at least one production reactor.

In one embodiment of the system of the invention, an outlet of the seed reactor and an outlet of a second feed reactor are connected to a mixing chamber, wherein an outlet of the mixing chamber is connected to an inlet of the at least one production reactor.

In one embodiment of the system of the invention, the seed reactor is a stirred tank reactor or plug flow reactor.

In one embodiment of the system of the invention, the at least one production reactor is a stirred tank reactor or a plug flow reactor.

In one embodiment of the system of the invention, the seed reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

In one embodiment of the system of the invention, the at least one production reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

In one embodiment of the system of the invention, the volume ratio of the seed reactor to the at least one production reactor is from about 1:10 to about 2:1, from about 1:5 to about 2:1, from about 1:2 to about to about 2:1, from about 1.5:1 to about 1:1.5, or about 1:1.

In one embodiment of the system of the invention, the at least one production reactor comprises a culture medium comprising cells with a biomass concentration from about 10 to about 90 g/L cell dry weight, preferably from about 20 to about 80 g/L cell dry weight, preferably from about 30 to about 70 g/L cell dry weight, preferably from about 35 to about 60 g/L cell dry weight.

The present invention further relates to a continuous fermentation process for the production of a nucleotide of interest or a protein of interest by a bacterial host cell, wherein the bacterial host cell comprise under the control of a first inducible promoter a nucleotide sequence encoding a protein from a phage which inhibits growth of said bacterial host cell, comprising (a) culturing said bacterial host cell in an uninduced state with respect to the nucleotide sequence encoding a protein from a phage which inhibits growth of said bacterial host cell in a seed reactor;

(b) transferring at least an amount of the bacterial host cells obtained in (a) from said seed reactor to a production reactor; and (c) culturing said bacterial host cells in said production reactor in an induced state with respect to the nucleotide sequence encoding a protein from a phage which inhibits growth of said bacterial host cells;

wherein the seed reactor and production reactor is configured as an independent continuous fermentor and wherein the seed reactor and production reactor are connected with each other.

In one embodiment of the continuous fermentation process of the invention, (a) is for biomass production.

In one embodiment of the continuous fermentation process of the invention, in (c) growth of said bacterial host cells is inhibited by culturing said bacterial host cells in an induced state with respect to the nucleotide sequence encoding a protein from a phage which inhibits growth of said bacterial host cells, while said nucleotide of interest or said protein of interest is produced.

In one embodiment of the continuous fermentation process of the invention, the bacterial host cell comprises the nucleotide of interest or a nucleotide encoding the protein of interest.

In one embodiment of the continuous fermentation process of the invention, said nucleotide of interest encodes one or more proteins of interest.

In one embodiment of the continuous fermentation process of the invention, said nucleotide is a nucleic acid molecule.

In one embodiment of the continuous fermentation process of the invention, said nucleic acid molecule is a plasmid, minichromosome, or RNA.

In one embodiment of the continuous fermentation process of the invention, said nucleotide of interest or said nucleotide encoding the protein of interest is under the control of a second inducible promoter or under the control of a constitutive promoter.

In one embodiment of the continuous fermentation process of the invention, the promoter of said heterologous nucleotide sequence of is recognized by a RNA polymerase which is heterologous for said bacterial host cell, said heterologous RNA polymerase is encoded by a nucleotide sequence comprised by said bacterial host cell.

In one embodiment of the continuous fermentation process of the invention, said heterologous RNA polymerase is bacteriophage T3 RNA polymerase, T7 bacteriophage RNA polymerase, engineered orthogonal T7 RNA polymerase, bacteriophage SP6 RNA polymerase or bacteriophage Xp10 RNA polymerase.

In one embodiment of the continuous fermentation process of the invention, said nucleotide sequence encoding said heterologous RNA polymerase is under the control of a third inducible promoter or under the control of a constitutive promoter.

In one embodiment of the continuous fermentation process of the invention, said first, second or third inducible promoter is regulated by arabinose, IPTG, tryptophan, xylose, lactose, rhamnose, phosphate, propionate, benzoic acid, phage lambda cl protein or heat.

In one embodiment of the continuous fermentation process of the invention, said first, second or third promoter are different.

In one embodiment of the continuous fermentation process of the invention, said bacterial host cell has a non-functional arabinose operon.

In one embodiment of the continuous fermentation process of the invention, said bacterial host cell is *E. coli*, preferably *E. coli* B-lineage.

In one embodiment of the continuous fermentation process of the invention, (a) further comprises culturing said bacterial host cells in an uninduced state with respect to the nucleotide sequence encoding a protein from a phage which inhibits growth of said bacterial host cells in culture medium in a production reactor for biomass production.

In one embodiment of the continuous fermentation process of the invention, (c) further comprises inducing said first inducible promoter controlling said nucleotide sequence encoding a protein from a phage which inhibits growth of said bacterial host cells.

In one embodiment of the continuous fermentation process of the invention, (b) or (c) comprises inducing said second inducible promoter controlling said nucleotide of interest or said nucleotide encoding the protein of interest.

In one embodiment of the continuous fermentation process of the invention, (a), (b) or (c) comprises inducing said third inducible promoter controlling said nucleotide sequence encoding said heterologous RNA polymerase.

In one embodiment of the continuous fermentation process of the invention, the continuous fermentation process further comprises (d) harvesting the product resulting from the production of said nucleotide sequence of interest.

In one embodiment of the continuous fermentation process of the invention, the seed reactor does not comprise or does not essentially comprise an inducer for the first inducible promoter.

In one embodiment of the continuous fermentation process of the invention, at least one of the at least one production reactor comprises an inducer for the first inducible promoter.

In one embodiment of the continuous fermentation process of the invention, at least one of the at least one of the at least one production reactor comprises an inducer for the second inducible promoter.

In one embodiment of the continuous fermentation process of the invention, the first inducible promoter and the second inducible promoter can be induced by the same inducer.

In one embodiment of the continuous fermentation process of the invention, pH is regulated in the seed reactor.

In one embodiment of the continuous fermentation process of the invention, dissolved oxygen is regulated in the seed reactor.

In one embodiment of the continuous fermentation process of the invention, temperature is regulated in the seed reactor.

In one embodiment of the continuous fermentation process of the invention, gas flow is regulated in the seed reactor.

In one embodiment of the continuous fermentation process of the invention, the biomass concentration is regulated in the seed reactor by feed inflow and/or biomass outflow.

In one embodiment of the continuous fermentation process of the invention, pH is regulated in the at least one production reactor.

In one embodiment of the continuous fermentation process of the invention, dissolved oxygen is regulated in the at least one production reactor.

In one embodiment of the continuous fermentation process of the invention, temperature is regulated in the at least one production reactor.

In one embodiment of the continuous fermentation process of the invention, gas flow is regulated in the at least one production reactor.

In one embodiment of the continuous fermentation process of the invention, the at least one production reactor comprises a biomass sensor.

In one embodiment of the continuous fermentation process of the invention, the biomass concentration is regulated in the at least one production reactor by feed inflow, biomass inflow, and/or biomass outflow.

In one embodiment of the continuous fermentation process of the invention, the mean residence time of biomass in the at least one production reactor is from about 5 h to about 24 h, preferably from about 7 h to about 20 h, preferably from about 10 h to about 15 h.

In one embodiment of the continuous fermentation process of the invention, the continuous fermentation process further comprises a first feed container containing a first feed medium comprising a carbon source, wherein the first feed container is operably connected to an inlet of the seed reactor, wherein feed flow from the first feed container to the seed reactor is preferably regulated.

In one embodiment of the continuous fermentation process of the invention, the continuous fermentation process comprises a second feed container containing a second feed medium comprising a carbon source, wherein the second feed container is operably connected to an inlet of the at least one production reactor, wherein feed flow from the second feed container to the at least one production reactor is preferably regulated.

In one embodiment of the continuous fermentation process of the invention, an outlet of the seed reactor and an outlet of a second feed reactor are connected to a mixing chamber, wherein an outlet of the mixing chamber is connected to an inlet of the at least one production reactor.

In one embodiment of the continuous fermentation process of the invention, the seed reactor is a stirred tank reactor or a plug flow reactor.

In one embodiment of the continuous fermentation process of the invention, the at least one production reactor is a stirred tank reactor or a plug flow reactor.

In one embodiment of the continuous fermentation process of the invention, the seed reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

In one embodiment of the continuous fermentation process of the invention, the at least one production reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

In one embodiment of the continuous fermentation process of the invention, the volume ratio of the seed reactor to the at least one production reactor is from about 1:10 to about 2:1, from about 1:5 to about 2:1, from about 1:2 to about to about 2:1, from about 1.5:1 to about 1:1.5, or about 1:1.

In one embodiment of the continuous fermentation process of the invention, the at least one production reactor comprises a culture medium comprising cells with a biomass concentration from about 10 to about 90 g/L cell dry weight, preferably from about 20 to about 80 g/L cell dry weight, preferably from about 30 to about 70 g/L cell dry weight, preferably from about 35 to about 60 g/L cell dry weight.

In one embodiment of the continuous fermentation process of the invention, the bacterial host cells in the at least one production reactor is genetically stable for at least about 5 days, preferably at least about 7 days, preferably at least about 10 days.

In one embodiment of the continuous fermentation process of the invention, the process is operated for at least about 5 days, preferably at least about 7 days, preferably at least about 10 days.

$F2_{IN}$ is indicative of the feed medium flow, containing growth medium and inducer (IPTG and L-arabinose); $F2_{OUT}$ is indicative of the outflow of the production vessel containing the product enriched-biomass (in the case of Example 1, GFP) or the product enriched cell free supernatant (in the case of Example 2, SpA protein from *Staphylococcus aureus*).

Figure 4:
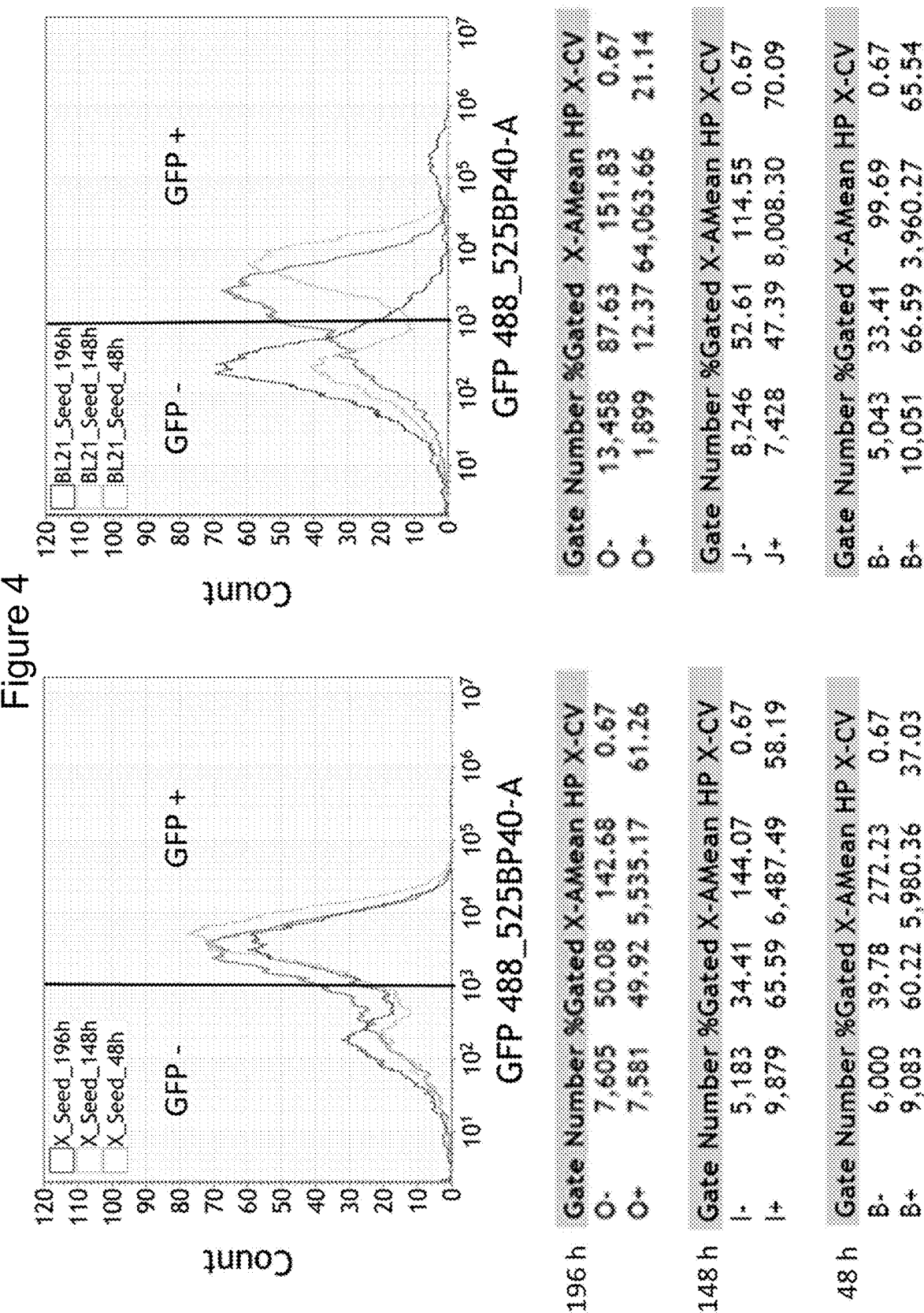

FIG. 4: FACS histogram for fluorescence readings shown for BL21(DE3)pET30a<GFP> in the seed reactor ($1^{st}$ stage) compared to enGenes-X-press pET30a<GFP> for different time points (48 h, 148 h, 196 h) in Example 1. Cells were gated in GFP positive (GFP+) and GFP negative (GFP−) cells with a fluorescent intensity of $1 \times 10^3$ arbitrary units. The table below gives the absolute number (Number), the percentage (% Gated), the mean fluorescence intensity (X-AMean) and half peak coefficient of variation (HP X-CV) of cells in the corresponding gate (O+/−, I+/−, B+/−) for the different timepoints (48 h, 148 h, 196 h). enGenes-X-press shows a more uniform population fluorescence distribution compared to BL21(DE3), in which the major cell population shows low level fluorescence after 196 h.

Figure 5:
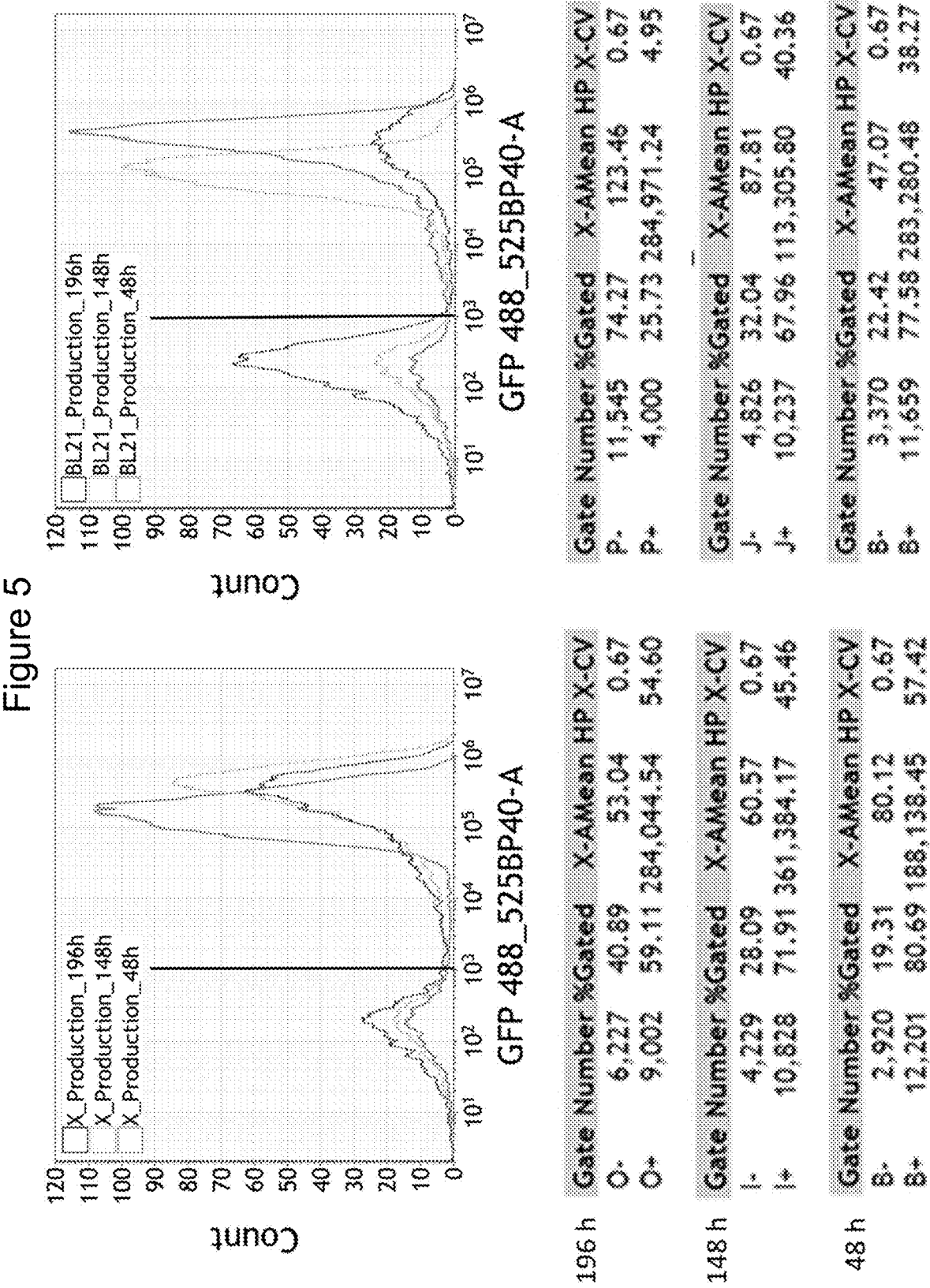

FIG. 5: FACS histogram for fluorescence readings shown for BL21(DE3)pET30a<GFP> in the production reactor ($2^{nd}$ stage) compared to enGenes-X-press pET30a<GFP> for different time points (48 h, 148 h, 196 h) in Example 1. Cells were gated in GFP positive (GFP+) and GFP negative (GFP−) cells with a fluorescent intensity of $1 \times 10^3$ arbitrary units. The table below gives the absolute number (Number), the percentage (% Gated), the mean fluorescence intensity (X-AMean) and half peak coefficient of variation (HP X-CV) of cells in the corresponding gate (O+/−, I+/−, B+/−) for the different time points (48 h, 148 h, 196 h). BL21(DE3) shows a clearly disappearing productive population after 196 h (25% GFP+ for BL21(DE3) vs. 59% GFP+ cells for enGenes-X-press).

Figure 6:
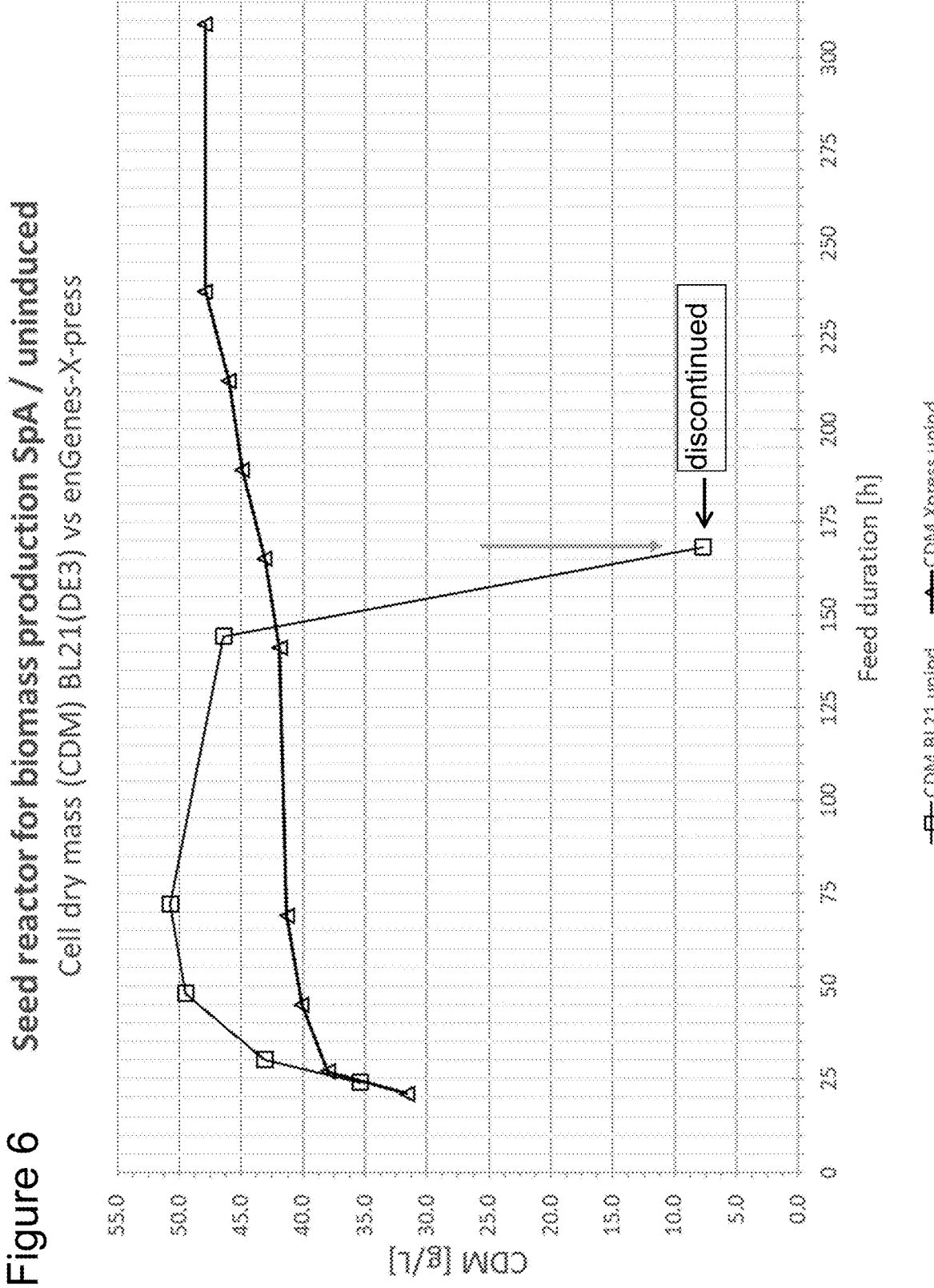

FIG. 6: Cell dry mass concentration [CDM, in g/L] for the seed reactor for biomass production (uninduced, without addition of IPTG and L-arabinose) in Example 2. Empty squares (□) shows BL21(DE3)pET30a<SpA> whereas empty triangle (Δ) shows enGenes-X-press pET30a<SpA>. CDM was followed for a period of 309 h, corresponding to more than 12 days. Abrupt population collapse is indicated by a grey arrow. Here, a drop in CDM is observable for BL21(DE3)pET30a<SpA> after 150 h in chemostat mode, but not observable for enGenes-X-press pET30a<SpA>, thereby showing an improved (genetic) stability and productivity of continuous production. Overall process was terminated for BL21(DE3) after population collapse in seed reactor.

Figure 7:
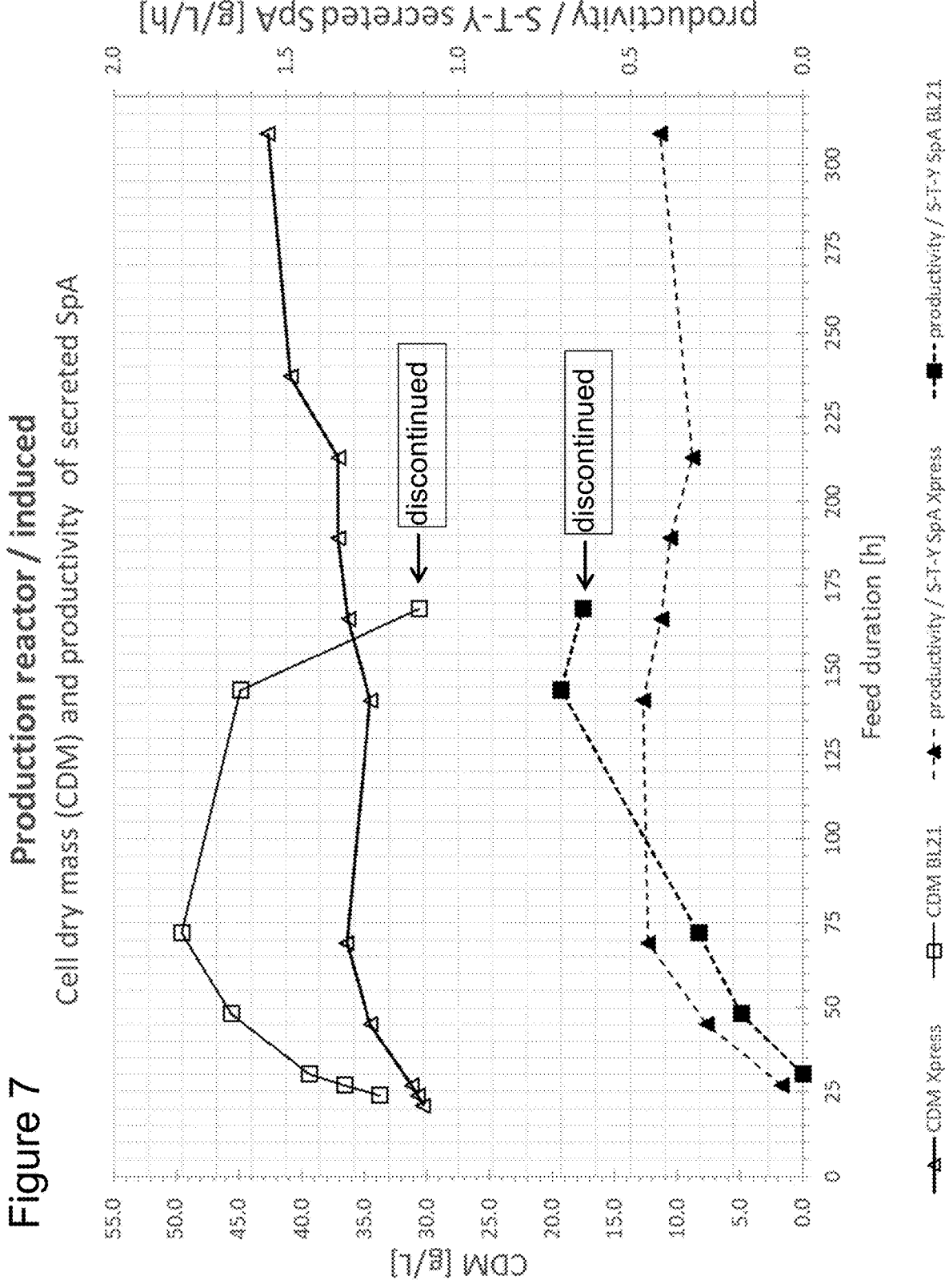

FIG. 7: Cell dry mass concentration [CDM, in g/L] and total volumetric yield for secreted SpA [g/L] for the production reactor (2nd stage) (induced, with addition of IPTG and L-arabinose in the case of X-press) in Example 2. Dashed line with filled square (□) shows BL21(DE3) pET30a<SpA> whereas dashed line with filled triangle (▲) shows enGenes-X-press pET30a<SpA>. CDM and total volumetric yield were followed for a period of 309 h, corresponding to 8 days. enGenes-X-press pET30a<SpA> shows a constant productivity of 0.4 g/L/h of secreted SpA yield over a time span of 309 h operated in 2-stage chemostat mode whereas the process for BL21(DE3) pET30a<SpA> had to terminated after 168 h due to abrupt population collapse in seed reactor 1.

Figure 8:
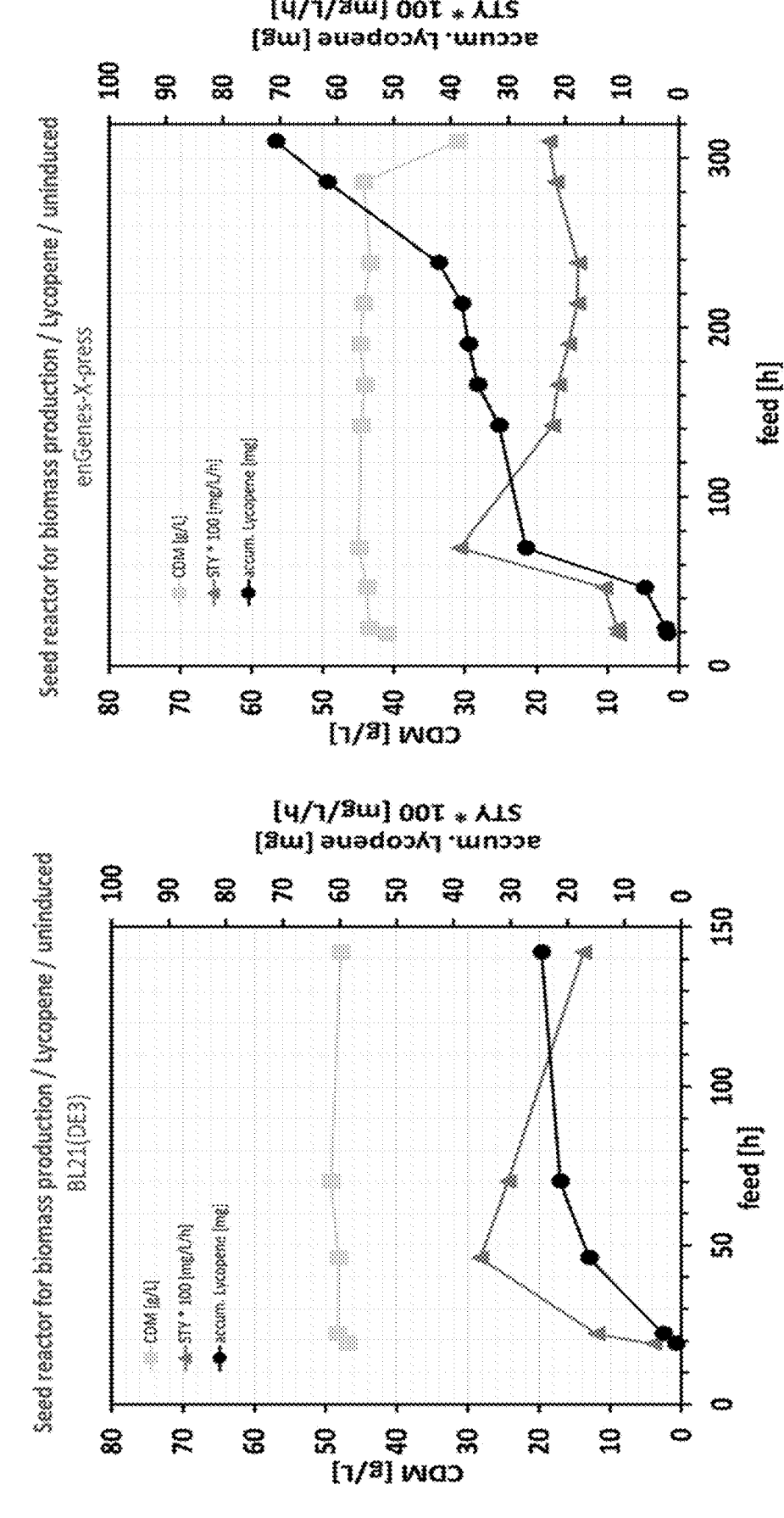
Figure 8:
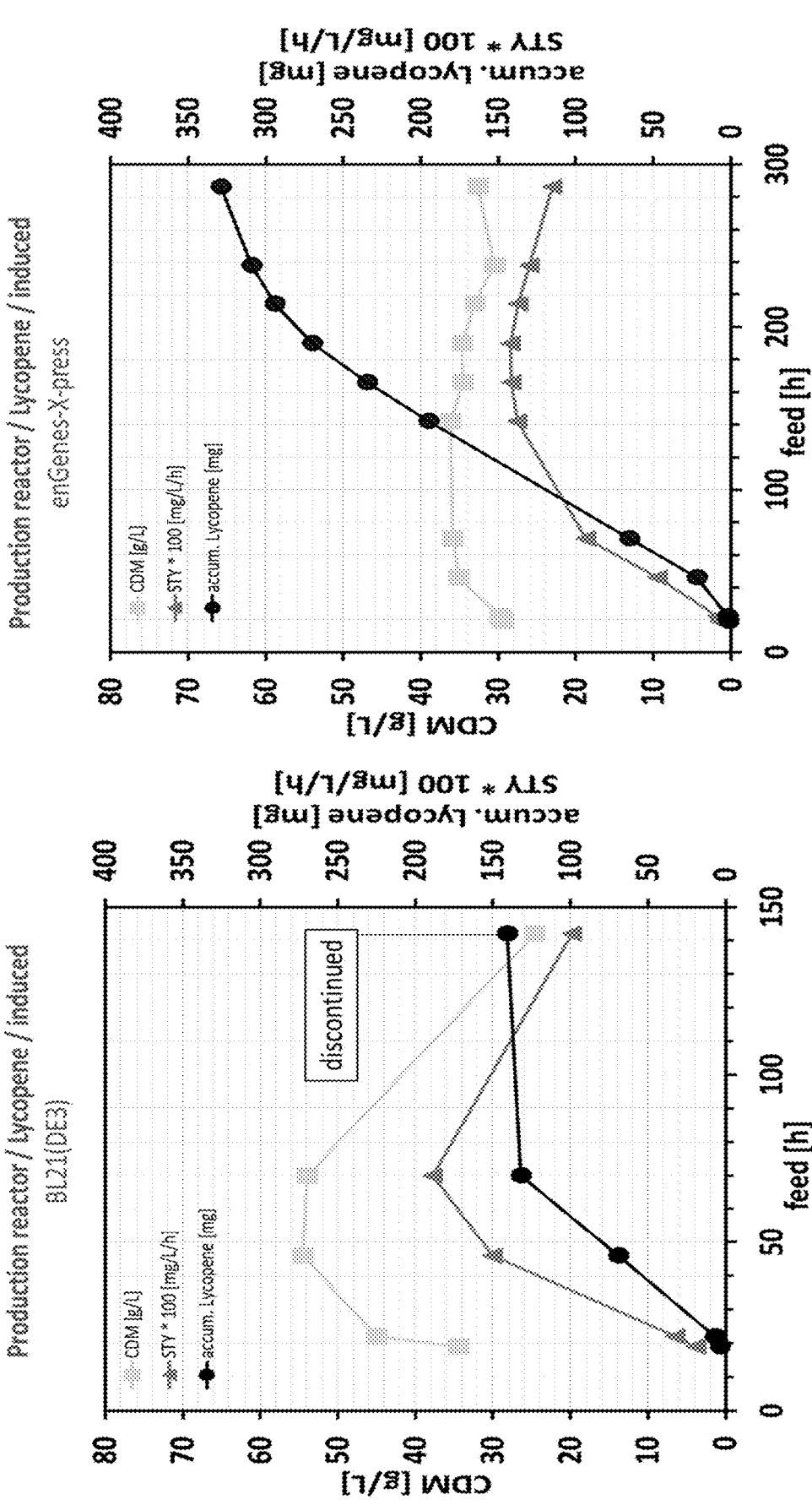

FIG. 8: Cell dry mass concentration [CDM, in g/L], total produced lycopene [mg] and space time yield (STY) for the seed (phase 1) and production reactor (phase 2) (induced, with addition of IPTG and L-arabinose in the case of X-press) for BL21(DE3) pET30a<crtE-crtB-crtl>cer and enGenes-X-press pET30a<crtE-crtB-crtl>cer are shown. Process lasted for 310 h, or 13 days (enGenes-X-press), respectively 142 h, or 6 days for BL21(DE3). enGenes-X-press pET30a<crtE-crtB-crtl>cer shows a constant increase in produced lycopene over a time span of 310 h operated in 2-stage chemostat mode whereas the process for BL21(DE3) pET30a<crtE-crtB-crtl>cer had to terminated after 142 h due to abrupt population collapse in production reactor (phase 2).

Figure 9:
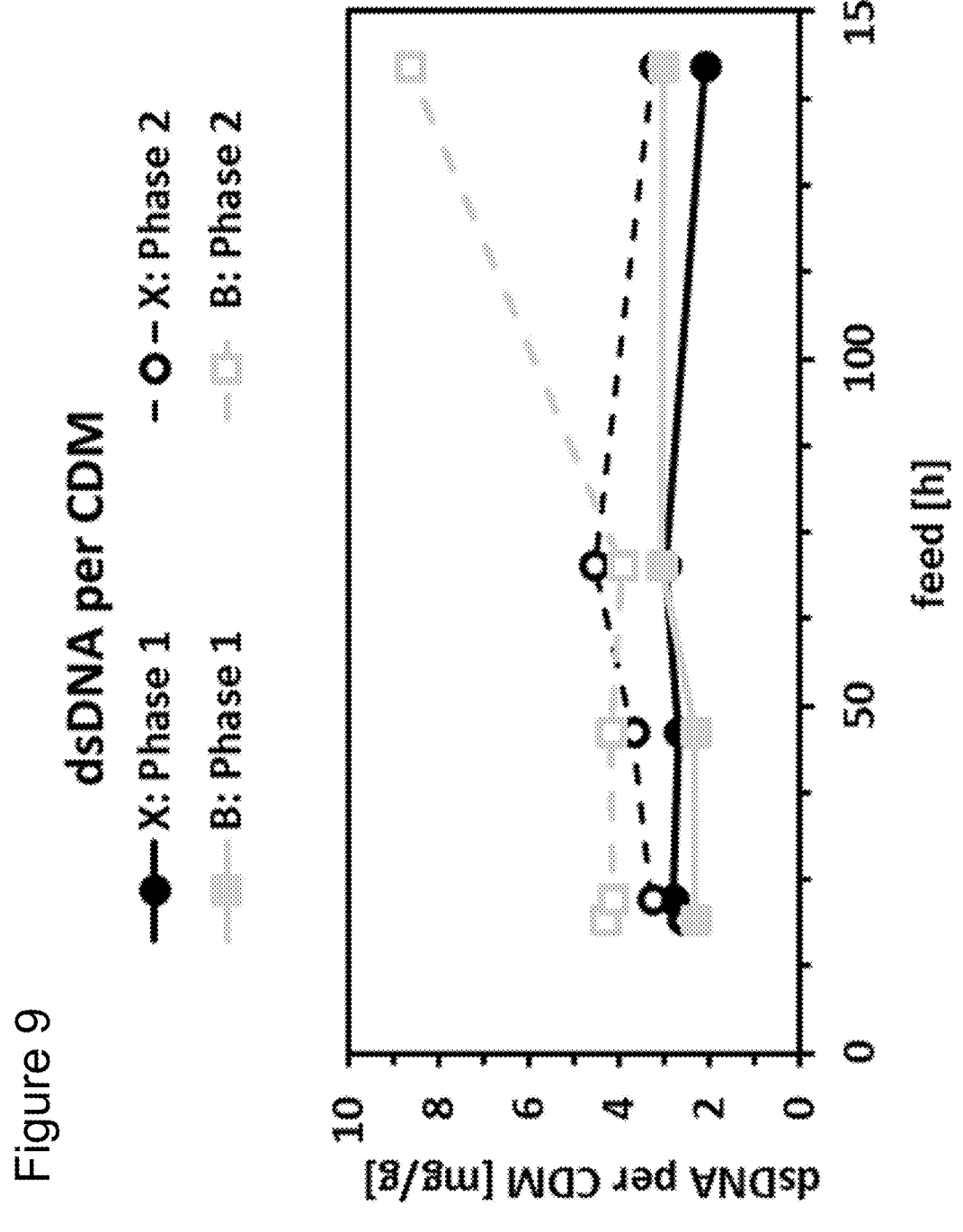

FIG. 9: Double stranded DNA (dsDNA) per g cell dry mass (CDM) for the seed (phase 1) and production reactor (phase 2) (induced, with addition of IPTG and L-arabinose in the case of X-press) for BL21(DE3) pET30a<crtE-crtB-crtl>cer (B) and enGenes-X-press pET30a<crtE-crtB-crtl>cer (X) are shown. enGenes-X-press pET30a<crtE-crtB-crtl>cer (X) shows a constant amount of dsDNA in the fermentation supernatant (phase 1 and 2) during 2-stage chemostat mode whereas the process for BL21(DE3) pET30a<crtE-crtB-crtl>cer (B) had to terminated after 142 h due to abrupt population collapse in production reactor (phase 2) after 70 h.

Figure 10:
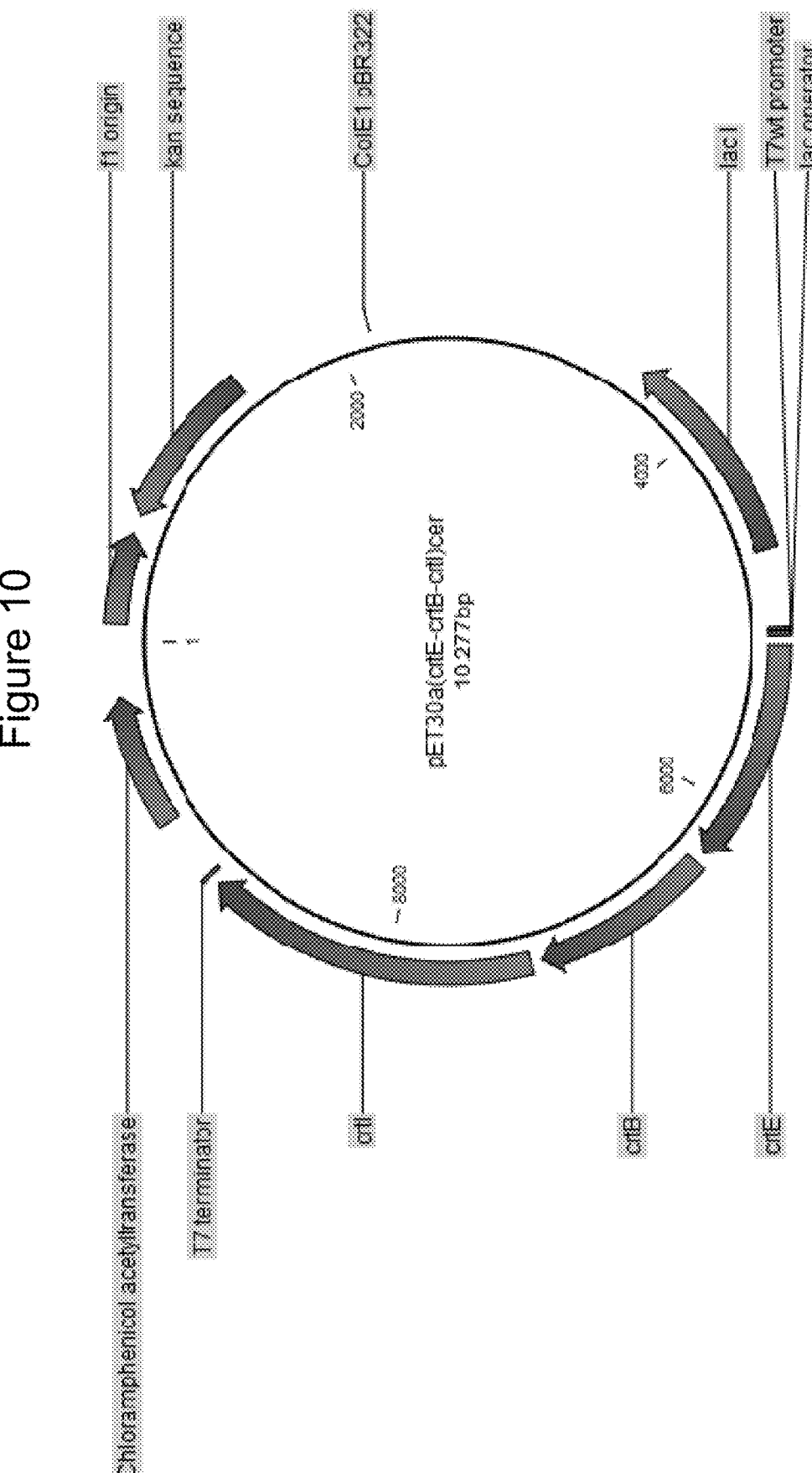

FIG. 10: Schematic representation of the pET30a<crtE-crtB-crtl>cer plasmid used in Example 3.

DETAILED DESCRIPTION

The present inventors successfully developed a system and a process for continuous production of proteins and nucleotides, such as plasmids. The present invention is based on the uncoupling of the growth ("growth-decoupling") of the host cell from the production of a protein or nucleotide of interest in a two stage process. In the inventive system and process of the invention, the growth, i.e. the propagation of the host cells, is spatially separated from the production of the nucleotide or protein of interest. In one bioreactor, the seed reactor, the host cells are kept under conditions that are ideal for their propagation. No production of the nucleotide or protein of interest is induced. Host cells from the seed reactor are continuously transferred into a second bioreactor, the production reactor. The growth of the host cell is inhibited and the production of the protein or nucleotide of interest is induced in the production reactor. This concept is referred to herein as "growth decoupling. This allows a continuous production. A fraction of the host cells or the supernatant/culture medium of the production reaction is continuously removed from the production reactor and the protein or nucleotide of interest can be harvested. The fraction that is removed from the production reactor will be preferably continuously replaced by fresh host cells from the seed reactor. As shown in Examples 1 and 2, this process can be employed for longer periods of times such as about 12 days as shown in Example 2. This technology therefore allows the continuous production of proteins or nucleotides of interest in rather small reactors with still high yield/ productivity and therefore improved S-T-Y (space-time-yield) of proteins or nucleotides of interest.

The double burden of a host cell caused by its proliferation and simultaneous expression of a heterologous protein reduces the yield of a protein of interest. In fact, the proliferation of the host cell during the production of a protein of interest poses an overload to the host cell resulting in a conflict in distribution of cellular resources. Thereby, several unwanted side effects like generation of toxic by-products, reduced oxygen transfer and induction of a stress response or plasmid loss ("genetic instability") are provoked, eventually resulting in a reorientation of the cellular metabolism constraining transcription and translation and potentially cell death. Given that the cellular synthesis capacity is the basis of heterologous protein expression, one has to take the capacity of a host cell into account. In order to reduce or abolish the unwanted side effects of heterologous protein expression, the present inventors have developed an expression system that uncouples the production of the protein of interest from the proliferation of the host cell, thereby considerably reducing the burden on the host cell and increasing the yield of a protein of interest—see also WO 2016/174195, incorporated hereby by reference in its entirety.

More particularly, the present inventors employ phage proteins that inhibit growth of the bacterial host cells by designing a host cell comprising a phage protein inhibiting growth of the bacterial host cell under the control of an inducible promoter and apply these host cells in a two stage process. This allows switching OFF the host cell's proliferation in the production reactor and allows high yield production in the production reactor. By applying a seed reactor, a continuous flow of fresh host cells into the production reactor is established. This allows a continuous production of the protein or nucleotide of interest. Separation of growth and production further surprisingly improves genetic stability at both seed and production stage reactor. Rai et al. (2018), Biotechnology and Bioengineering, 116: 693-703, describe a phenomenon which they refer to as "abrupt population collapse in chemostat fermentation" once minimal medium is employed. They observed a significant drop in biomass concentration in chemostat mode after ~150 h. This phenomenon may be due to genetic instability (e.g. loss of plasmid encoding the protein or nucleic acid of interest or mutations preventing the expression of the protein or nucleic acid of interest) was also observed by the present inventors when using bacterial host cells without an inducible protein from a phage, which inhibits growth of said bacterial host cell (see Examples 1 and 2). Thus, a person skilled in the art willing to develop a continuous fermentation process with a "standard" bacterial host cell, e.g., *E. coli*, does not have a reasonable expectation of success.

However, this abrupt population collapse is surprisingly not taking place in a bacterial host cell, wherein the bacterial host cell comprises under the control of a first inducible promoter a nucleotide sequence encoding a protein from a phage which inhibits growth of said bacterial host cell such as a modified BL21(DE3) strain, having the Gp2 protein integrated into its genome under control of an L-arabinose inducible promoter (c.f. the enGenes-X-press strain disclosed herein). Using the bacterial host cell of the invention, a continuous production process in form a two stage production regime could by performed for extended periods of time, i.e. at least 12 days as described in experiment 1 and 2. The continuous fermentation process of the invention results in elevated continuous product yields and improved productivity. Thus, the system and method of the present invention surprisingly also overcomes the problem of abrupt population collapse. The bacterial host cells of the invention can therefore be described more genetically stable in comparison to standard bacterial host cells.

Furthermore, oxygen consumption, nutritional requirements and metabolic heat development are reduced, a stress response in the production reactor is circumvented and therefore sufficient (internal) microbial metabolic resources for the production of the protein or nucleotide of interest are available. An additional problem of heterologous protein expression is the incorporation of the protein of interest in inclusion bodies that results in a decreased solubility and thereby yield. This effect can be avoided by reducing cellular proliferation and induction temperature as shown by Vernet et al. (2010, Protein Expression and Purification, Vol. 77, Issue 1: 104-111) and thus by the present growth decoupled production system.

Phage proteins which inhibit cell growth have been found by the present inventors to be useful in uncoupling growth of a host cell and production of a protein of interest of said host cell. In fact, the phage protein ideally brings the host cell to halt, while an expression system that is insensitive to said phage protein can ideally fully exploit the protein production machinery of the halted host cell. For example, bacteriophage T7 uses its proteins gp0.7 and Gp2 to shut off *E. coli* RNA polymerase after infection. Immediately after infection early viral class I genes of bacteriophage T7, under control of bacterial promoters, are expressed, such as T7 RNA polymerase which is highly specific for viral genes under control of the T7 promoter. Among the class I genes is Gp0.7, which phosphorylates inter alia *E. coli* RNA polymerase resulting in transcription termination of early genes and in switching from host to viral RNA polymerase. Subsequently, the viral gene Gp2 is expressed, binding to and further inhibiting the beta subunit of the host RNA polymerase. Together Gp0.7 and/or Gp2 inhibit *E. coli* RNA polymerase and thereby cellular proliferation, resulting in a take-over of the bacterial protein synthesis machinery for viral purposes. Inhibition of *E. coli* RNA polymerase by Gp2 was shown by Studier and Moffat (1986, J. Mol. Biol., 189, 113-130), whereas they missed to disclose an impact on cellular proliferation, yet provide any incentive to apply the host cell shut-off in a two stage production process as described herein.

Yet, apart from Gp0.7 and Gp2 further such phage proteins are available and have been used by the present inventors to show that their concept of using a phage protein for uncoupling growth of a host cell from its capacity of producing a nucleotide or protein of interest by using an expression system that is insensitive to such a phage protein. Further such phage proteins are, for example, Nun, Gp6, Gp8 or A*, *Bacillus* phage SPO1 GP40 SPO1 GP40, *Staphylococcus* phage G1 GP67, *Thermus thermophilus* phage P23-45 GP39, Enterobacteria phage PhiEco32 GP79, *Xanthomonas oryzae* bacteriophage Xp10 P7 protein, Enterobacteria phage T4 Alc protein, Enterobacteria phage T4Asia or *Bacillus subtilis* ykzG protein which are known in the art and are also described herein.

The present inventors adopted this functional principle in a two stage process in two separate bioreactors for the purpose of producing a nucleotide or protein of interest. A (bacterial) host cell suitable for the system or the process of the invention may comprise (i) a phage protein under control of an inducible promoter which inhibits growth of the bacterial host cell, (ii) a heterologous RNA polymerase absent in the bacterial host cell and (iii) a protein of interest under control of a promoter recognized by said heterologous RNA polymerase, thereby facilitating to inhibit the cellular proliferation and concentrate the host cells capacity on the production of the protein of interest.

As described herein, the inventors developed a new and inventive system suitable for the continuous production of proteins or nucleotides of interest applying a two stage process, in which microbial or bacterial growth is spatially separated.

Accordingly, the present invention provides a system for use in continuous production of a protein or nucleotide of interest by a bacterial host cell, wherein the bacterial host cell comprises under the control of a first inducible promoter a nucleotide sequence encoding a protein from a phage which inhibits growth of said bacterial host cell, comprising (a) a seed reactor comprising said bacterial host cell in an uninduced state with respect to the nucleotide sequence encoding a protein from a phage which inhibits growth of said bacterial host cells, the seed reactor having at least one inlet and at least one outlet, and (b) at least one production reactor comprising said bacterial host cells in an induced state with respect to the nucleotide sequence encoding a protein from a phage which inhibits growth of said bacterial host cells, each production reactor having at least one inlet and at least one outlet, wherein an inlet of the production reactor is connected to an outlet of the seed reactor.

In a preferred embodiment, the present invention relates to a system for use in continuous production of a protein of interest by a bacterial host cell, wherein the bacterial host cell comprises under the control of a first inducible promoter a nucleotide sequence encoding a protein from a phage which inhibits growth of said bacterial host cell, comprising (a) a seed reactor comprising said bacterial host cell in an uninduced state with respect to the nucleotide sequence encoding a protein from a phage which inhibits growth of said bacterial host cells, the seed reactor having at least one inlet and at least one outlet, and (b) at least one production reactor comprising said bacterial host cells in an induced state with respect to the nucleotide sequence encoding a protein from a phage which inhibits growth of said bacterial host cells, each production reactor having at least one inlet and at least one outlet, wherein an inlet of the production reactor is connected to an outlet of the seed reactor.

The present invention further relates to a system for use in continuous production of a heterologous nucleotide sequence of interest by microbial host cells which comprise said heterologous nucleotide sequence of interest, wherein growth of said microbial host cells can be decoupled from production of said heterologous nucleotide sequence of interest through induction of genetic inhibition of growth of said microbial host cells, comprising (a) a seed reactor comprising said microbial host cells in an uninduced state with respect to the genetic inhibition of growth, the seed reactor having at least one inlet and at least one outlet, and (b) at least one production reactor comprising said microbial host cells in an induced state with respect to the genetic inhibition of growth, thereby growth of said microbial host cells is genetically inhibited, while said nucleotide sequence of interest is produced, each production reactor having at least one inlet and at least one outlet, wherein an inlet of the production reactor is connected to an outlet of the seed reactor.

Preferably, genetic inhibition of growth is accomplished by a protein from a phage which inhibits growth of said bacterial host cells, said protein from a phage is encoded by a nucleotide sequence which is under the control of a first inducible promoter and is comprised by said bacterial host cells. Preferably, genetic inhibition of growth is accomplished by repressing bacterial DNA replication [targeting dnaA and oriC] or blocking nucleotide synthesis [targeting pyrF or thyA] through CRISPR interference technology.

The system of the present may also be used in a process for the production of a nucleotide of interest or a protein of interest. I.e., the present invention not only relates to a system for the production of a protein or nucleotide of interest but also to the 2 stage process itself that can be carried out making use of the system of the invention. 2 stage in this context does not necessarily mean that the growth of the microbial or bacterial host cells and the production of the protein or nucleotide of interest are followed by each other but they preferably are carried out at the same time. In other words, the growth and production preferably take place simultaneously and not in two separate steps followed by each other.

Accordingly, the present invention relates to a continuous fermentation process for the production of a protein or nucleotide of interest by a bacterial host cell, wherein the bacterial host cell comprise under the control of a first inducible promoter a nucleotide sequence encoding a protein from a phage which inhibits growth of said bacterial host cell, comprising (a) culturing said bacterial host cell in an uninduced state with respect to the nucleotide sequence encoding a protein from a phage which inhibits growth of said bacterial host cell in a seed reactor;

(b) transferring at least an amount of the bacterial host cells obtained in (a) from said seed reactor to a production reactor; and (c) culturing said bacterial host cells in said production reactor in an induced state with respect to the nucleotide sequence encoding a protein from a phage which inhibits growth of said bacterial host cells;

wherein the seed reactor and production reactor is configured as an independent continuous fermenter and wherein the seed reactor and production reactor are connected with each other.

In a preferred embodiment, the present invention relates to a continuous fermentation process for the production of a protein of interest by a bacterial host cell, wherein the bacterial host cell comprise under the control of a first inducible promoter a nucleotide sequence encoding a protein from a phage which inhibits growth of said bacterial host cell, comprising (a) culturing said bacterial host cell in an uninduced state with respect to the nucleotide sequence encoding a protein from a phage which inhibits growth of said bacterial host cell in a seed reactor;

(b) transferring at least an amount of the bacterial host cells obtained in (a) from said seed reactor to a production reactor; and (c) culturing said bacterial host cells in said production reactor in an induced state with respect to the nucleotide sequence encoding a protein from a phage which inhibits growth of said bacterial host cells;

wherein the seed reactor and production reactor is configured as an independent continuous fermenter and wherein the seed reactor and production reactor are connected with each other.

"Continuous fermentation" relates to operating conditions, in which a liquid medium, such as a culture or nutrient medium, or a cells broth, is added to the fermenter, while culture fluid is released from the fermenter. The influx of the liquid medium is preferably constant at a certain rate or intermittently. The efflux of the culture fluid is preferably at the same rate so that the amount of liquid in the fermenter remains essentially constant. During continuous fermentation, biomass preferably remain essentially unchanged. In the steady state, the fermentation condition can be maintained, such as nutrient concentration, product concentration, constant pH, biomass according to the need. Reactors used for continuous fermentation can be stirred tank reactors or tubular reactors. A "continuous fermenter" as used herein is a fermenter that is suitable for continuous fermentation.

(Initial) initiation of the continuous process of the invention may be done as following. Both, the seed and the production reactor, may be started as a batch culture followed by fed-batch until the necessary biomass concentration is achieved. Thus, during the initiation or, in other words, starting of the process of the invention, the microbial or bacterial host cells preferably are (both in the seed reactor and the production reactor) in an uninduced state with respect to the nucleotide sequence encoding a protein form a phage which inhibits growth of said microbial or bacterial host cells. When the required cell density is reached, the production in the production reactor can be induced by addition of the inducer—in other words: The production reactor now is in an induced state with respect to the nucleotide sequence encoding a protein form a phage which inhibits growth of said microbial or bacterial host cells. Additionally, the continuous process can be started by transferring microbial or bacterial host cells from the seed reactor to the production reactor, e.g. by starting a flow of culture medium into the seed reactor, thereby creating a flow from the seed reactor outlet to the production reactor inlet. Thus, in the continuous process of the invention, the cell growth is preferably inhibited in the production reactor.

As described herein, the seed reactor is for propagation of the host cells. Accordingly, in the continuous fermentation process of the invention, (a) preferably is for biomass production.

In the continuous fermentation process of the invention, in (c) growth of said bacterial host cells preferably is inhibited by culturing said bacterial host cells in an induced state with respect to the nucleotide sequence encoding a protein from a phage which inhibits growth of said bacterial host cells, while said nucleotide of interest or said protein of interest is produced.

In the process of the invention, (a) may further comprise culturing said bacterial host cells in an uninduced state with respect to the nucleotide sequence encoding a protein from a phage which inhibits growth of said bacterial host cells in culture medium in a production reactor for biomass production.

In the process of the invention, (c) may further comprise inducing said first inducible promoter controlling said nucleotide sequence encoding a protein from a phage which inhibits growth of said bacterial host cells.

In the process of the invention, (b) or (c) may comprise inducing said second inducible promoter controlling said nucleotide of interest or said nucleotide encoding the protein of interest.

In the process of the invention, (a), (b) or (c) may comprise inducing said third inducible promoter controlling said nucleotide sequence encoding said heterologous RNA polymerase.

The process of the invention may further comprise (d) harvesting the product resulting from the production of said nucleotide sequence of interest. The harvesting may be done continuously or a defined volume can be removed from the production reactor on a regular basis.

Since the host cells continuously are replaced by the volume flow from the seed reactor, one advantage of the present invention is that the production reactor comprises genetic stable host cells or, in other words, cell division is stopped in the production reactor and adaptive evolution (leading to genetic instability) is hindered. Additionally, microbial or bacterial host cells preferably are replaced before they can lose their expression plasmids. Accordingly, the bacterial host cells in the at least one production reactor preferably are genetically stable for at least about 5 days, preferably at least about 7 days, preferably at least about 10 days, more preferably at least 13 days. The genetic stability may also be accompanied by the option to operate the process for a longer period of time, thereby enabling automation of the process. Thus, the process of the invention may be operated for at least about 5 days, preferably at least about 7 days, preferably at least about 10 days, more preferably at least 13 days. A further possibility to genetically stabilize a plasmid-based continuous production system can be the use of auxotrophic markers in combination with an auxotrophic host strain.

The present invention further relates to a continuous fermentation process for the production of a heterologous nucleotide sequence of interest by microbial host cells comprising said heterologous nucleotide sequence of interest, wherein growth of said microbial host cells can be decoupled from production of said heterologous nucleotide sequence of interest through induction of genetic inhibition of growth of said microbial host cells, comprising (a) culturing said microbial host cells in an uninduced state with respect to the genetic inhibition of growth in culture medium in a seed reactor for biomass production;

(b) transferring at least an amount of said bacterial host cells from said seed reactor to culture medium of a production reactor; and (c) culturing said bacterial host cells in said production reactor in an induced state with respect to the genetic inhibition of growth, thereby growth of said microbial host cells is genetically inhibited, while said nucleotide sequence of interest is produced;

wherein the seed reactor and production reactor is configured as an independent continuous fermentor and wherein the seed reactor and production reactor are directly connected with each other.

Preferably, genetic inhibition of growth is accomplished by a protein from a phage which inhibits growth of said bacterial host cells, said protein from a phage is encoded by a nucleotide sequence which is under the control of a first inducible promoter and is comprised by said bacterial host cells. Preferably, genetic inhibition of growth is accomplished by repressing bacterial DNA replication [e.g., targeting dnaA and oriC] or blocking nucleotide synthesis [e.g., targeting pyrF or thyA] through CRISPR interference technology.

The term "microbial host cell" as used herein relate to microscopically small organisms that are not visible to the naked eye as individuals, into which a nucleic acid comprising an expression cassette or vector has been introduced, i.e. which has been genetically-engineered. Most microorganisms are unicellular organisms, but they may also include small organisms (fungi, algae, yeast) of corresponding size. Microorganisms include, but are not limited to, bacteria (e.g. lactic acid bacteria), many fungi including yeasts such as baker's yeast, microscopic algae (e.g. chlorella) and protozoa. Preferably, the microbial host cells are fungal host cells, yeast host cells or bacterial host cells. Most preferably, the microbial host cells are bacterial host cells.

The term "bacterial host cell", as used herein, is intended to refer to any prokaryotic cell, into which a nucleic acid comprising an expression cassette or vector has been introduced, i.e. which has been genetically-engineered. A preferred example of a prokaryotic host cell is E. coli. However, also Pseudomonas species, Salmonella species, Bacillus species, Lactobacillus species, Corynebacterium species, Microbacterium species or Actinomycetes species are envisaged. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell, preferably grown in culture. In a preferred embodiment or the present invention the bacterial host cell is E. coli. In a more preferred embodiment, the bacterial host cell is E. coli B-lineage such as E. coli BL21 or more preferably E. coli BL21(DE3). The E. coli may also be from the K-lineage such as E. coli K12 or W-lineage. In a preferred embodiment, the bacterial host cell is E. coli BL21(DE3)::TN7(PPΔAra), wherein "PP" relates to a protein from a phage as described herein. The bacterial host cell may thus comprise a knockout of araABCD and a protein from a phage preferably under the control of an inducible promoter and preferably integrated at the attTN7 site. The protein from a phage may however also be integrated at another suitable site. In a more preferred embodiment, the bacterial host cell is E. coli BL21(DE3)::TN7 (Gp2ΔAra), wherein Gp2 preferably has the amino acid sequence shown in SEQ ID NO: 1 or a fragment thereof which inhibits bacterial host cell RNA polymerase or has an identity of 40% or more to the amino acid sequence shown in SEQ ID NO: 1 and which inhibits bacterial host cell RNA polymerase. In a preferred embodiment, Gp2 is SEQ ID NO: 1. E. coli BL21(DE3)::TN7(Gp2ΔAra), wherein Gp2 has the amino acid sequence shown in SEQ ID NO: 1 is also described herein as "enGenes-X-press". The bacterial host cells described herein may be created as described in WO 2016/174195, hereby incorporated by reference.

A skilled artisan is aware of genetic engineering techniques known in the art in order to generate a bacterial host cell for use in the system or process of the invention. For example, various kits are available for genetic engineering of bacterial host cell for the integration of nucleic acids comprising nucleotide sequences into a bacterial genome, either randomly or targeted; see e.g. Zhang et al. (1998), Nature Genetics 20, 123-128 or Sharan et al. (2009), Nature Protocols 4(2), 206-223. A skilled artisan is further aware of techniques for the transformation of bacterial host cell as well as with any other cloning technique which he can use for the generation of extrachromosomal elements such as plasmids, cosmids, bacmids, etc.

The term "growth" of the host cell as used herein means an increase of cell number due to cell division.

A promoter sequence as used herein is a non-coding expression control sequence preferably inserted nearby the start of the coding sequence of the expression cassette and regulates its expression. Put into a simplistic yet basically correct way, it is the interplay of the promoter with various specialized proteins called transcription factors that determine whether or not a given coding sequence may be transcribed and eventually translated into the actual protein encoded by the gene. It will be recognized by a person skilled in the art that any compatible promoter can be used for recombinant expression in host cells. The promoter itself may be preceded by an upstream activating sequence, an enhancer sequence or combination thereof. These sequences are known in the art as being any DNA sequence exhibiting a strong transcriptional activity in a cell and being derived from a gene encoding an extracellular or intracellular protein. It will also be recognized by a person skilled in the art that termination and polyadenylation sequences may suitably be derived from the same sources as the promoter.

The term "inducible promoter" as used herein refers to a promoter that regulates the expression of an operably linked gene or functional RNA in response to the presence or absence of an endogenous or exogenous stimulus. Such stimuli can be but are not limited to chemical compounds or environmental signals such as temperature shifts. Examples for inducible promoters include, but are not limited to, pBAD, OR2-OR1-PR, pLtetO, pLlacO, PesR, pLac, lacUV, Tac promoter, pPrpB, pTetO, FixK2, pLtetO-1 or PcpcG2.

In one embodiment, the bacterial host cell comprises the nucleotide of interest or a nucleotide encoding the protein of interest. In a preferred embodiment, the bacterial host cell comprises a nucleotide encoding the protein of interest.

As outlined herein, the production of the nucleotide or protein of interest preferably takes place in the production reactor. Accordingly, the nucleotide of interest or the protein of interest preferably is produced in the at least one production reactor.

The system and the process of the present invention are both suitable for the production of a nucleotide of interest or a protein of interest; they thus cannot only be used for the production of proteins but also to produce nucleotides, such as plasmids, in high amounts.

The terms "nucleotide", "nucleotide sequence" or "nucleic acid molecule" as used herein may be used interchangeably and refer to a polymeric form of nucleotides (i.e. polynucleotide) which are usually linked from one deoxyribose or ribose to another. The term "nucleotide sequence" preferably includes single and double stranded forms of DNA or RNA. A nucleic acid molecule of this invention may include both sense and antisense strands of RNA (containing ribonucleotides), cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

In this regard, a nucleic acid being an expression product is preferably a DNA such as a plasmid, whereas a nucleic acid to be introduced into a cell is preferably DNA, e.g. genomic DNA or cDNA.

The nucleic acid molecule preferably is a plasmid, minichromosome, or RNA.

The nucleic acid can be in any topological conformation. For instance, the nucleic acid can be single-stranded, double-stranded, triple-stranded, quadruplexed, partially double-stranded, branched, hairpinned, circular, or in a padlocked conformation.

The nucleotide may be a nucleic acid molecule.

The nucleotide of interest preferably is inducible, e.g. by specific environmental conditions. The nucleotide of interest may be capable of runaway replication, e.g. as described in Camps (2010), Rect Pat DNA Gene Seq, 4(1):58-73, hereby incorporated by reference. The induction of the nucleotide of interest, which is suited for runaway replication, in the production reactor may be done, e.g., by amino acid starvation in the production bioreactor.

A "polypeptide" refers to a molecule comprising a polymer of amino acids linked together by peptide bonds. Said term is not meant herein to refer to a specific length of the molecule and is therefore herein interchangeably used with the term "protein". When used herein, the term "polypeptide" or "protein" also includes a "polypeptide of interest" or "protein of interest", which is expressed by the expression cassettes or vectors or can be isolated from the host cells of the invention. A protein of interest also includes proteins which may potentially be harmful or even toxic for host cells.

Examples of a protein of interest are enzymes more preferably an amylolytic enzyme, a lipolytic enzyme, a proteolytic enzyme, a cellulytic enzyme, an oxidoreductase or a plant cell-wall degrading enzyme; and most preferably an enzyme having an activity selected from the group consisting of aminopeptidase, amylase, amyloglucosidase, carbohydrase, carboxypeptidase, catalase, cellulase, chitinase, cutinase, cyclodextrin glycosyltransferase, desoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, and xylanase. Furthermore, a protein of interest may also be a growth factor, cytokine, receptors, receptor ligands, therapeutic proteins such as interferons, BMPs, GDF proteins, fibroblast growth factors, peptides such as protein inhibitors, membrane proteins, membrane-associated proteins, peptide/protein hormones, peptidic toxins, peptidic antitoxins, antibody or functional fragments thereof such as Fab or $F(ab)_2$ or derivatives of an antibody such as bispecific antibodies (for example, scFvs), chimeric antibodies, humanized antibodies, single domain antibodies such as Nanobodies or domain antibodies (dAbs) or an anticalin and others.

A "polypeptide" as used herein encompasses both naturally-occurring and non-naturally-occurring proteins, and fragments, mutants, derivatives and analogues thereof. Polypeptides may be a polypeptide homologous (native) or heterologous to the host cell. The polypeptide of interest may also encompass a polypeptide native to the host cell, which is encoded by a nucleic acid sequence, which expression is controlled by one or more control sequences foreign to the nucleic acid sequence encoding the polypeptide. Polypeptides may be of any length. Polypeptides include proteins and/or peptides of any activity or bioactivity. A "peptide" encompasses analogues and mimetics that mimic structural and thus biological function.

Polypeptides may further form dimers, trimers and higher oligomers, i.e. consisting of more than one polypeptide molecule. Polypeptide molecules forming such dimers, trimers etc. may be identical or non-identical. The corresponding higher order structures are consequently termed homo- or heterodimers, homo- or heterotrimers etc.

Further, a polypeptide may comprise a number of different domains each of which has one or more distinct activities.

The nucleic acid sequence encoding a protein of the present invention or protein of interest may be obtained from any prokaryotic, eukaryotic, or other source.

As described herein, a nucleotide sequence encoding a protein of the present invention or protein of interest is preferably regulated by a (second) promoter. Said (second) promoter is preferably specifically transcribed by an RNA polymerase that is heterologous for said host cell and the expression of which may be inducible. However, said RNA polymerase may also be constitutively expressed.

The nucleotide of interest may encode more than one protein of interest to, e.g., encode a complete biosynthesis pathway or cluster. Accordingly, the nucleotide of interest may encode one or more proteins of interest.

In the two stage process and system of the invention, the growth of the microbial or bacterial host cells is inhibited in the production reactor. Thereby, the microbial or bacterial host cells concentrate on the production while growth that would disturb the production, is inhibited.

When "growth of a bacterial host cell" is inhibited as described herein, growth may be inhibited by inhibition of transcription, DNA-replication and/or cell division. Accordingly, it is preferred that a phage protein, particularly one or more of the phage proteins described herein, inhibits transcription, DNA-replication and/or cell division.

"Genetic inhibition" as used herein relates to inhibition of growth of the microbial or bacterial host cell by expressing a molecule, e.g. a protein or RNA, that interferes with the growth of the microbial or bacterial host cell. Such a protein may be a phage protein.

A "phage protein" when referred to herein is a protein from a (bacterio)phage. A phage infects bacteria and is able to replicate in said bacterium. When infecting a bacterium and replicating in said bacterium a phage may have one or more proteins that inhibit growth of said bacterium, e.g., by inhibiting transcription, DNA-replication and/or cell division in order to fully exploit the protein synthesis machinery of said bacterium.

Accordingly, the present invention can be put into practice with any phage protein that effects the inhibition of the growth of the bacterial host cell by causing, e.g. a host transcription shut-off. In this case the bacterial host cell comprises under the control of an inducible promoter a nucleotide sequence encoding a protein from a phage which causes a transcription shut-off of said bacterial host cell. The term "host transcription shut-off" as used herein relates to the inhibition of transcription of the bacterial host cell. Proteins that can be used to cause a host transcription shut-off are described herein, such as Gp2 (e.g. SEQ ID NO: 1), GP0.7 (e.g. SEQ ID NO: 3), Nun (e.g. SEQ ID NO: 2), Gp6 (e.g. SEQ ID NO: 4), Gp8 (e.g. SEQ ID NO: 5), A* (e.g. SEQ ID NO: 6), YkzG Epsilon-Subunit (e.g. SEQ ID NO: 7), preferably Gp2. However, further proteins that effect a host transcription shut-off may be used as well to put the present invention into practice. Such proteins are for example *Bacillus* phage SPO1 GP40 (e.g. SEQ ID NO: 8), *Staphylococcus* phage G1 GP67 (e.g. SEQ ID NO: 9), *Thermus thermophilus* phage P23-45 GP39 (e.g. SEQ ID NO: 10), Enterobacteria phage PhiEco32 GP79 (e.g. SEQ ID NO: 11), *Xanthomonas oryzae* bacteriophage Xp10 P7 protein (e.g. SEQ ID NO: 12), Enterobacteria phage T4 Alc protein (e.g. SEQ ID NO: 13), Enterobacteria phage T4 Asia protein (e.g. SEQ ID NO: 14). Another example for a phage protein which inhibits growth of the bacterial host cell is T7 Gp5.7 (e.g. SEQ ID NO: 17).

Accordingly, the phage protein of the present invention is preferably (i) a protein which inhibits bacterial host cell RNA polymerase, wherein said protein is
  (a) a protein having the amino acid sequence shown in Seq Id No: 1 or a fragment thereof which inhibits bacterial host cell RNA polymerase; or
  (b) a protein having an amino acid sequence which has an identity of 40% or more, such as 50%, 60%, 70%, 80% or 90% to the amino acid sequence shown in Seq Id No: 1, the protein is preferably capable of inhibiting bacterial host cell RNA polymerase;

(ii) a protein which inhibits bacterial host cell RNA polymerase, wherein said protein is
  (a) a protein having the amino acid sequence shown in Seq Id No: 2 or a fragment thereof which inhibits bacterial host cell RNA polymerase; or
  (b) a protein having an amino acid sequence which has an identity of 40% or more, such as 50%, 60%, 70%, 80% or 90% to the amino acid sequence shown in Seq Id No: 2, the protein is preferably capable of inhibiting bacterial host cell RNA polymerase;

(iii) a protein which phosphorylates bacterial host cell RNA polymerase, wherein said protein is
  (a) a protein having the amino acid sequence shown in Seq Id No: 3 or a fragment thereof which phosphorylates bacterial host cell RNA polymerase; or
  (b) a protein having an amino acid sequence which has an identity of 40% or more, such as 50%, 60%, 70%, 80% or 90% to the amino acid sequence shown in Seq Id No: 3, the protein is preferably capable of phosphorylating bacterial host cell RNA polymerase;

(iv) a protein which inhibits bacterial host cell DNA replication, wherein said protein is
  (a) a protein having the amino acid sequence shown in Seq Id No: 4 or a fragment thereof which inhibits bacterial host cell DNA replication; or
  (b) a protein having an amino acid sequence which has an identity of 40% or more, such as 50%, 60%, 70%, 80% or 90% to the amino acid sequence shown in Seq Id No: 4, the protein is preferably capable of inhibiting bacterial host cell DNA replication;

(v) a protein which inhibits bacterial host cell DNA replication, wherein said protein is
  (a) a protein having the amino acid sequence shown in Seq Id No: 5 or a fragment thereof which inhibits bacterial host cell DNA replication; or
  (b) a protein having an amino acid sequence which has an identity of 40% or more, such as 50%, 60%, 70%, 80% or 90% to the amino acid sequence shown in Seq Id No: 5, the protein is preferably capable of inhibiting bacterial host cell DNA replication; or (vi) a protein which inhibits bacterial host cell DNA replication, wherein said protein is
  (a) a protein having the amino acid sequence shown in Seq Id No: 6 or a fragment thereof which inhibits bacterial host cell DNA replication; or
  (b) a protein having an amino acid sequence which has an identity of 40% or more, such as 50%, 60%, 70%, 80% or 90% to the amino acid sequence shown in Seq Id No: 6, the protein is preferably capable of inhibiting bacterial host cell DNA replication;

(vii) a protein which inhibits bacterial host cell RNA polymerase, wherein said protein is
  (a) a protein having the amino acid sequence shown in Seq Id No: 7 or a fragment thereof which inhibits bacterial host cell RNA polymerase; or (b) a protein having an amino acid sequence which has an identity of 40% or more, such as 50%, 60%, 70%, 80% or 90% to the amino acid sequence shown in Seq Id No: 7, the protein is preferably capable of inhibiting bacterial host cell RNA polymerase;

(viii) a protein which causes host transcription shut-off, wherein said protein is (a) a protein having the amino acid sequence shown in Seq Id No: 8, 9, 10, 11, 12, 13, 14 or a fragment thereof which causes host transcription shut-off; or (b) a protein having an amino acid sequence which has an identity of 40% or more, such as 50%, 60%, 70%, 80% or 90% to the amino acid sequence shown in Seq Id No: 8, 9, 10, 11, 12, 13 or 14, the protein is preferably capable of causing host transcription shut-off; or (ix) a protein which inhibits bacterial host cell RNA polymerase, wherein said protein is (a) a protein having the amino acid sequence shown in Seq Id No: 17 or a fragment thereof which inhibits bacterial host cell RNA polymerase; or (b) a protein having an amino acid sequence which has an identity of 40% or more to the amino acid sequence shown in Seq Id No: 17 and which inhibits bacterial host cell RNA polymerase.

In a further preferred embodiment of the present invention said nucleotide sequence encoding a protein from a phage which inhibits growth of said bacterial host cell, said nucleotide sequence encoding said RNA polymerase, said nucleotide sequence encoding a protein of interest, is integrated into the genome of said host cell or is comprised by an extrachromosomal vector.

The term "vector" as used herein refers to a nucleic acid sequence into which an expression cassette comprising nucleotide of interest or a gene of the present invention or gene encoding the protein of interest may be inserted or cloned. Furthermore, the vector may encode an antibiotic resistance gene conferring selection of the host cell. Preferably, the vector is an expression vector.

The vector may be capable of autonomous replication in a host cell (e.g., vectors having an origin of replication which functions in the host cell). The vector may have a linear, circular, or supercoiled configuration and may be complexed with other vectors or other material for certain purposes.

Vectors used herein for expressing an expression cassette comprising a gene of the present invention or gene encoding the protein of interest usually contain transcriptional control elements suitable to drive transcription such as e.g. promoters, enhancers, polyadenylation signals, transcription pausing or termination signals as elements of an expression cassette. For proper expression of the polypeptides, suitable translational control elements are preferably included in the vector, such as e.g. preferably optimized 5' untranslated regions leading to ribosome binding sites (RBS) suitable for recruiting ribosomes and stop codons to terminate the translation process. In particular, the nucleotide sequence serving as the selectable marker genes as well as the nucleotide sequence encoding the protein of interest can be transcribed under the control of transcription elements present in appropriate promoters. The resultant transcripts of the selectable marker genes and that of the protein of interest harbour functional translation elements that facilitate substantial levels of protein expression (i.e. translation) and proper translation termination. In a preferred embodiment of the invention the selectable marker used is an auxotrophic marker gene used in a host strain containing an knock-out or deletion of said auxotrophic marker gene.

The vector may comprise a polylinker (multiple cloning site), i.e. a short segment of DNA that contains many restriction sites, a standard feature on many plasmids used for molecular cloning. Multiple cloning sites typically contain more than 5, 10, 15, 20, 25, or more than 25 restrictions sites. Restriction sites within an MCS are typically unique (i.e., they occur only once within that particular plasmid). MCSs are commonly used during procedures involving molecular cloning or sub cloning.

One type of vector is a plasmid, which refers to a circular double stranded DNA loop into which additional DNA segments may be introduced via ligation or by means of restriction-free cloning. Other vectors include cosmids, bacterial artificial chromosomes (BAC), yeast artificial chromosomes (YAC) or mini-chromosomes. Another type of vector is a viral vector, wherein additional DNA segments may be ligated into the viral genome.

The expression cassette comprising a gene of the present invention or gene encoding the protein of interest is inserted into the expression vector as a DNA construct. This DNA construct can be recombinantly made from a synthetic DNA molecule, a genomic DNA molecule, a cDNA molecule or a combination thereof. The DNA construct is preferably made by ligating the different fragments to one another according to standard techniques known in the art.

The expression cassette comprising a gene of the present invention or gene encoding the protein of interest may be part of the expression vector. Preferably, the expression vector is a DNA vector. The vector conveniently comprises sequences that facilitate the proper expression of the gene encoding the protein of interest and the antibiotic resistance gene. These sequences typically comprise but are not limited to promoter sequences, transcription initiation sites, transcription termination sites, and polyadenylation functions as described herein.

The expression cassettes may comprise an enhancer and/or an intron. Usually, introns are placed at the 5' end of the open reading frame. Accordingly, an intron may be comprised in the expression cassette for expressing the polypeptide of interest in order to increase the expression rate. Said intron may be located between the promoter and or promoter/enhancer element and the 5' end of the open reading frame of the polypeptide to be expressed. Several suitable introns are known in the state of the art that can be used in conjunction with the present invention.

The expression cassette or vector according to the invention which is present in the host may either be integrated into the genome of the host or it may be maintained in some form extrachromosomally.

Furthermore, the expression cassettes may comprise an appropriate transcription termination site. This, as continued transcription from an upstream promoter through a second transcription unit may inhibit the function of the downstream promoter, a phenomenon known as promoter occlusion or transcriptional interference. This event has been described in both prokaryotes and eukaryotes. The proper placement of transcriptional termination signals between two transcription units can prevent promoter occlusion. Transcription termination sites are well characterized and their incorporation in expression vectors has been shown to have multiple beneficial effects on gene expression.

The terms "5'" and "3'" used herein refer to a convention used to describe features of a nucleotide sequence related to either the position of genetic elements and/or the direction of events (5' to 3'), such as e.g. transcription by RNA polymerase or translation by the ribosome which proceeds in 5' to 3' direction. Synonyms are upstream (5') and downstream (3'). Conventionally, nucleotide sequences, gene maps, vector cards and RNA sequences are drawn with 5' to 3' from left to right or the 5' to 3' direction is indicated with arrows, wherein the arrowhead points in the 3' direction. Accordingly, 5' (upstream) indicates genetic elements positioned towards the left hand side, and 3' (downstream) indicates genetic elements positioned towards the right hand side, when following this convention.

The term "expression" as used herein means the transcription of a nucleotide sequence. Said nucleotide sequence encodes preferably a protein. Accordingly, said term also includes the production of mRNA (as transcription product from a nucleotide sequence) and translation of this mRNA to produce the corresponding gene product, such as a polypeptide, or protein.

The gene of interest, i.e. the nucleotide of interest or the nucleotide of interest, may be integrated into the genome of the microbial or bacterial host cell, e.g. by homologous recombination at a pre-selected site. An exemplary method for the genome integration of the gene of interested is described in WO 2008/142028, incorporated herewith in its entirety.

The RNA polymerase is advantageously heterologous to the bacterial host cell which comprises a nucleotide sequence encoding said RNA polymerase. "Heterologous" means that the RNA polymerase is not naturally occurring in said bacterial host cell, i.e., said bacterial host cell does not naturally comprise said RNA polymerase, unless a nucleotide sequence encoding said RNA polymerase is introduced in said bacterial host cell in accordance with the teaching of the present invention by means and methods known in the art. The RNA polymerase is thus ideally insensitive to a phage protein which inhibits growth of said bacterial host cell.

Preferably, the RNA polymerase is bacteriophage T3 RNA polymerase, T7 bacteriophage RNA polymerase, engineered orthogonal T7 RNA polymerase, bacteriophage SP6 RNA polymerase or bacteriophage Xp10 RNA polymerase. Further RNA polymerases, such as engineered orthogonal T7 polymerases are described in Temme et al. (2012), Nucleic Acids Research 40(17), 8773-8781. Preferably, the RNA polymerase is the T7 bacteriophage RNA polymerase.

In a preferred embodiment of the present invention the nucleotide sequence encoding the RNA polymerase is under the control of an inducible or constitutive promoter. Examples of inducible promoters are described herein in the context of an inducible promoter which controls a nucleotide sequence encoding a protein from a phage which inhibits growth of said bacterial host cell. These inducible promoters are also preferred examples for an inducible promoter that controls the RNA polymerase as described herein below.

In general, a second nucleotide or protein of interest could be under the control of a promoter that is recognized by a second heterologous RNA polymerase that is different to the first heterologous RNA polymerase to allow e.g. different expression levels of two different nucleotides or proteins of interest.

Preferably, the inducible promoter which controls a nucleotide sequence encoding a protein from a phage which inhibits growth of said bacterial host cell is regulated by arabinose, IPTG, tryptophan, xylose, lactose, rhamnose, phosphate, propionate, benzoic acid, phage lambda cl protein or heat.

As regards inducible promoters that control a nucleotide sequence encoding a protein from a phage which inhibits growth of said bacterial host cell as or that control a nucleotide sequence encoding said RNA polymerase, it is preferred that the same inducible promoters are applied. Preferred examples are described herein. This preferred embodiment allows to simultaneously induce expression of the phage protein and the RNA polymerase in order to uncouple growth and nucleic acid/protein production. However, of course, also different inducible promoters can be used in accordance with the teaching of the present invention. Accordingly, the first, second or third promoter may be different.

In a preferred embodiment of the bacterial host cell of the process or system of the invention, said host cell has a non-functional arabinose operon.

The systems and the processes of the present invention relate on the use of bioreactors, preferably at least two separate bioreactors. In one bioreactor, the seed reactor, the microbial or bacterial cells are cultured and expanded, wherein in the second bioreactor, the production reactor, the growth of the microbial or bacterial cell is inhibited and the production of the nucleotide or protein of interest is induced. The first and the second bioreactor preferably are coupled to allow the transfer of new microbial or bacterial host cells from the seed to the production reactor. Thus, each of the first and the second bioreactor has at least one inlet and at least one outlet.

"Bioreactor" or "reactor", including the "seed bioreactor" or the "production bioreactor", as used herein bioreactor refers to a reaction vessel for fermentation for production of cells and biosynthetic products, which may range in size from benchtop fermenters to industrial tanks. Bioreactors preferably allow automatic regulation of the flow of oxygen, culture medium and other nutrients, and maintaining the temperature and pH; they preferably minimize the potential for contamination and can produce a higher density of cells than can be produced in traditional cultures.

"Seed reactor" as used herein in the process and the system of the invention relates to the bioreactor that is used for propagation of the microbial or bacterial host cell. In the seed reactor the microbial or bacterial host cell is in an uninduced state with respect to the nucleotide sequence encoding a protein from a phage which inhibits growth of said microbial or bacterial host cell. Otherwise, propagation in the seed reactor could not take place.

The term "uninduced state with respect to the nucleotide sequence encoding a protein from a phage which inhibits growth of said bacterial host cell" relates to a microbial or bacterial host cell, in which the promoter of the gene encoding the protein from a phage which inhibits growth of the microbial or bacterial host cell has not been induced. As described herein, inhibition of the growth of the microbial or bacterial host cell is inhibited by the expression of a protein from a phage. Since the protein from a phage is under the control of an inducible promoter, the uninduced state within the context of the invention thus means that the inducible promoter has not been induced. Uninduced in this context may mean, e.g. that in case of a chemically inducible promoter the inducer is not or not in sufficient concentration present in the culture medium, or that the effects of the inducer are impaired by other factors (e.g. the presence of glucose may suppress induction of a lac operon even in the inducer lactose is present) or in case of a temperature-sensitive promoter, the temperature for activation is not reached. This is preferred in the seed reactor. Accordingly, the microbial or bacterial host cell preferably is cultured in an uninduced state with respect to the nucleotide sequence encoding a protein from a phage which inhibits growth of said bacterial host cell in the seed reactor for biomass production.

Accordingly, the seed reactor preferably does not comprise or does not essentially comprise an inducer for the first inducible promoter. The first inducible promoter controls a nucleotide sequence encoding a protein from a phage which inhibits growth of said microbial or bacterial host cell. The seed reactor preferably is substantially free of an inducer for the first promoter, i.e. preferably in a concentration that does not induce a detectable expression of the protein from a phage which inhibits growth of said microbial or bacterial host cell ("substantially free").

"Production reactor" as used herein in the process and the system of the invention relates to the bioreactor that is used for the production of the nucleotide or protein of interest. In the production reactor, the growth of the host cells is inhibited by inducing the first promoter, and the production of the production of the nucleotide or protein of interest, which is under control of the second inducible promoter, is induced. Accordingly, the microbial or bacterial host cell is in an induced state with respect to the nucleotide sequence encoding a protein from a phage which inhibits growth of said microbial or bacterial host cell. Otherwise, production in the production reactor could not take place.

Accordingly, the microbial or bacterial host cell preferably is in an "induced state with respect to the nucleotide sequence encoding a protein from a phage" in the production reactor. Thus, in this case the inducible promoter is induced and the growth of the microbial or bacterial host cell is inhibited. Accordingly, the microbial or bacterial host cell is cultured in an induced state with respect to the nucleotide sequence encoding a protein from a phage which inhibits growth of said bacterial host cell in the production reactor for production of said nucleotide sequence of interest by said bacterial host cells.

Accordingly, the production reactor or the at one of the least one production reactor comprises an inducer for the first inducible promoter. The first inducible promoter controls a nucleotide sequence encoding a protein from a phage which inhibits growth of said microbial or bacterial host cell.

Since the nucleotide or protein of interest is under the control of the second inducible promoter, the production reactor preferably comprises and inducer for the second inducible promoter. Accordingly, the at least one of the at least one production reactors comprises an inducer for the second inducible promoter.

The inducer for the first and the second inducible promoter may be different. The inducer for the first and the second inducible promoter may be the same. Accordingly, the first inducible promoter and the second inducible promoter preferably can be induced by the same inducer. The first and the second inducible promoter may be the same.

Bioreactors often comprise a variety of sensors that monitor important parameters such as pH, dissolved oxygen or temperature and means for controlling these parameters.

Accordingly, the seed reactor preferably comprises a means for regulating pH. The at least one production reactor preferably comprises a means for regulating pH. Means for regulating the pH may include a pH probe, a device for recording the signal of the pH probe, and/or a device for adding acid or base to the culture medium, preferably base.

The seed reactor preferably comprises means for regulating dissolved oxygen. The at least one production reactor preferably comprises means for regulating dissolved oxygen. Means for regulating dissolved oxygen may comprise a $pO_2$ probe, a control system for regulating $pO_2$ by pressure, ventilation rate, addition of oxygen, control of stirring and/or the like.

The seed reactor preferably comprises means for regulating temperature. The at least one production reactor preferably comprises means for regulating temperature. Means for regulating the temperature may comprise a thermometer, a heating device, a cooling device, wherein the temperature control by the heating and/or the cooling device preferably is carried out by heating and/or cooling the mantle of the bioreactor.

The seed reactor preferably comprises a gas inlet and a gas outlet and a means for regulating the gas flow. The at least one production reactor preferably comprises a gas inlet and a gas outlet and a means for regulating the gas flow. The at least one production reactor preferably comprises a biomass sensor.

Accordingly, the production reactor preferably comprises a means for regulating pH. The at least one production reactor preferably comprises a means for regulating pH. Means for regulating the pH may include a pH probe, a device for recording the signal of the pH probe, and/or a device for adding acid or base to the culture medium, preferably base.

The production reactor preferably comprises means for regulating dissolved oxygen. The at least one production reactor preferably comprises means for regulating dissolved oxygen. Means for regulating dissolved oxygen may comprise a $pO_2$ probe, a control system for regulating $pO_2$ by pressure, ventilation rate, addition of oxygen, control of stirring and/or the like.

The production reactor preferably comprises means for regulating temperature. The at least one production reactor preferably comprises means for regulating temperature. Means for regulating the temperature may comprise a thermometer, a heating device, a cooling device, wherein the temperature control by the heating and/or the cooling device preferably is carried out by heating and/or cooling the mantle of the bioreactor.

The production reactor preferably comprises a gas inlet and a gas outlet and a means for regulating the gas flow. The at least one production reactor preferably comprises a gas inlet and a gas outlet and a means for regulating the gas flow. The at least one production reactor preferably comprises a biomass sensor.

The biomass concentration may be regulated in the seed reactor by feed inflow and/or biomass outflow. The biomass concentration may be regulated in the at least one production reactor by feed inflow, biomass inflow, and/or biomass outflow.

The gas flow may be regulated in the at least one production reactor. The gas flow may be regulated in the at least one seed reactor.

The seed and the production reactor(s) are linked or coupled to allow the transfer of microbial or bacterial host cells from the seed reactor(s) to the production reactor(s). The flow of the culture medium comprising the host cells from the seed reactor to the production reactor preferably is controlled. This control can be done, e.g., by applying a chemostat or a turbidostat. Accordingly, the system of the present invention preferably further comprises (c) means for operating the seed and production reactors as linked chemostats or turbidostats. Preferably, the seed reactor outflow serves as inflow to the production reactor.

A "chemostat" (from chemical environment is static) as used herein relates to a bioreactor to which fresh medium, preferably comprising the microbial or bacterial host cells grown in the seed reactor, is continuously added (to the production reactor), while culture liquid containing left over nutrients, metabolic end products and the microbial or bacterial host cells, preferably comprising the nucleotide or protein of interest, are continuously removed at the same rate to keep the culture volume constant. One of the most important features of chemostats is that the microbial or bacterial host cells can be kept in a physiological steady state under constant environmental conditions. In this steady state, all culture parameters preferably remain constant (culture volume, dissolved oxygen concentration, nutrient and product concentrations, pH, cell density, etc.) as well as the number of the microbial or bacterial host cells (in the production reactor). In addition, environmental conditions can be controlled.

A "turbidostat" as used herein relates to a continuous microbiological culture device, similar to a chemostat, which has feedback between the turbidity of the culture vessel and the dilution rate. A turbidostat dynamically adjusts the flow rate (and therefore the dilution rate) to make the turbidity constant. At steady state, operation of both the chemostat and turbidostat are identical. While most turbidostats use a spectrophotometer/turbidimeter to measure the optical density for control purposes, there exist other methods, such as dielectric permittivity.

The system of the invention preferably comprises a first feed container containing a first feed medium comprising a carbon source, wherein the first feed container is operably connected to an inlet of the seed reactor, wherein the system preferably comprises means for regulating feed flow from the first feed container to the seed reactor.

"Carbon source" as used herein carbon source refers to the molecules used by an organism as the source of carbon for building its biomass. A carbon source can be an organic compound or an inorganic compound. Heterotrophs needs organic compounds as source of carbon and source of energy, while autotrophs can use inorganic compounds as carbon source and an abiotic sources of energy, as light (photoautotrophs) or inorganic chemical energy (chemolithotrophs). Examples for carbon sources include, but are not limited to, glucose, maltose, lactose, galactose, fructose, sorbitol, mannose, arabinose, xylose, ribose, glycerol, pyruvate, oxaloacetate, succinate, fumarate, malate or the like.

The "feed flow" describes the amount of culture medium, preferably comprising the microbial or bacterial host cell, that is transferred to the production reactor in a distinct period of time and may be expressed as volume per time, e.g. liters per minute. The feed flow may be regulated e.g. by an adjustable or controllable pump.

In one embodiment of the system of the invention, the system comprises a second feed container containing a second feed medium comprising a carbon source, wherein the second feed container is operably connected to an inlet of the at least one production reactor, wherein the system preferably comprises means for regulating feed flow from the second feed container to the at least one production reactor. The second feed may comprise the inducer.

The system of the present invention is not limited to a single seed reactor. Several seed reactors may be employed. Thus, the system of the invention may comprise at least one seed reactor, two seed reactors, three seed reactors, four seed reactors, five seed reactors or at least five seed reactors.

In one embodiment an outlet of the seed reactor and an outlet of a second feed reactor are connected to a mixing chamber, wherein an outlet of the mixing chamber is connected to an inlet of the at least one production reactor. This configuration has the advantage that the microbial or bacterial host cells can be contacted and/or homogenously mixed with the inducer prior to the introduction into the production reactor.

Just like a multitude of seed reactors may be used, also a plurality of production reactors can be used. Thus, the system or the process of the invention may comprise at least one bioreactor, at least two bioreactors, two bioreactors, at least three bioreactors, three bioreactors, at least four bioreactors, four bioreactors or at least five bioreactors.

The bioreactors of the present invention, i.e. the seed and/or the production reactor, may be any bioreactor suitable for the purposes of the present invention. In one embodiment, the seed reactor is a stirred tank reactor. In one embodiment, the seed reactor is a plug flow reactor. In one embodiment, the production reactor is a stirred tank reactor. In one embodiment, the production reactor is a plug flow reactor.

In one embodiment the outlet of the production reactor is connected to a cell retention system (e.g. cross-flow filtration system or a disc (stack) centrifuge) that preferably allows continuous separation of the cell free supernatant (culture medium) from the bacterial host cells (in case the retentate comprising the bacterial host cells is recirculated into the production reactor).

The size or the volume of the bioreactors may differ. The seed reactor preferably has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L. The at least one production reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L. The seed reactor preferably has a volume of up to 50 $m^3$, up to 45 $m^3$, up to 40 $m^3$, up to 35 $m^3$, up to 30 $m^3$, up to 25 $m^3$, up to 20 $m^3$, up to 15 $m^3$, up to 10 $m^3$, up to 5 $m^3$, up to 2.5 $m^3$ or up to 1 $m^3$. The production reactor preferably has a volume of up to 50 $m^3$, up to 45 $m^3$, up to 40 $m^3$, up to 35 $m^3$, up to 30 $m^3$, up to 25 $m^3$, up to 20 $m^3$, up to 15 $m^3$, up to 10 $m^3$, up to 5 $m^3$, up to 2.5 $m^3$ or up to 1 $m^3$.

The volume ratio of the seed reactor to the at least one production reactor may be from about 1:10 to about 2:1, from about 1:5 to about 2:1, from about 1:2 to about to about 2:1, from about 1.5:1 to about 1:1.5, or about 1:1.

In a preferred embodiment, the at least one production reactor comprises a culture medium comprising cells with a biomass concentration from about 10 to about 90 g/L cell dry weight, preferably from about 20 to about 80 g/L cell dry weight, preferably from about 30 to about 70 g/L cell dry weight, preferably from about 35 to about 60 g/L cell dry weight.

A large number of suitable methods exist in the art to produce polypeptides in host cells of the invention. Conveniently, the produced protein is harvested from the culture medium, lysates of the cultured host cell or from isolated (biological) membranes by established techniques. For example, an expression cassette comprising, inter alia, the nucleotide sequence encoding the protein of interest can be synthesized by PCR and inserted into the expression vector. Subsequently, a cell may be transformed with the expression vector. Thereafter, the cell is cultured to produce/express the desired protein(s), which is/are isolated and purified. For example, the product may be recovered from the host cell and/or culture medium by conventional procedures including, but not limited to, cell lysis, breaking up host cells, centrifugation, filtration, ultra-filtration, extraction, evaporation, spray drying or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

"Isolating the protein of interest" refers to the separation of the protein of interest produced during or after expression of the vector introduced. In the case of proteins or peptides as expression products, said proteins or peptides, apart from the sequence necessary and sufficient for the protein to be functional, may comprise additional N- or C-terminal amino acid sequences. Such proteins are referred to as fusion proteins.

When a polypeptide of interest is expressed in a host cell of the invention, it may be necessary to modify the nucleotide sequence encoding said polypeptide by adapting the codon usage of said nucleotide sequence to meet the frequency of the preferred codon usage of said host cell. As used herein, "frequency of preferred codon usage" refers to the preference exhibited by the host cell of the invention in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG).

A tag may be used to allow identification and/or purification of the protein of interest. Accordingly, it is preferred that a protein of interest comprises a tag. Hence, a nucleotide sequence encoding a protein of interest preferably also encodes a tag which is advantageously genetically fused in frame to the nucleotide sequence encoding said protein of interest. Said tag may be at the C- or N-terminus of said protein of interest. Examples of tags that may be used in accordance with the invention include, but are not limited to, HAT, FLAG, c-myc, hemagglutinin antigen, His (e.g., 6×His) tags, flag-tag, strep-tag, strepII-tag, TAP-tag, chitin binding domain (CBD), maltose-binding protein, immunoglobulin A (IgA), His-6-tag, glutathione-S-transferase (GST) tag, intein and streptavidin binding protein (SBP) tag.

A leader peptide tag may be used to target the protein of interest to the periplasmic space or to the extracellular space. Examples of leader peptide sequences in accordance with the invention are, but are not limited to, pelB (e.g. positions 1-19 of UniProt entry P14005, version 1 of the sequence), ompA (e.g. positions 1-21 of UniProt entry POA910, version 1 of the sequence), torA (e.g. positions 1-39 of UniProt entry P33225, version 2 of the sequence), dsbA (e.g. positions 1-19 of UniProt entry POAEG4, version 1 of the sequence), enterotoxin STII (e.g. positions 1-23 of UniProt entry P22542, version 1 of the sequence) and phoA (e.g. positions 1-21 of UniProt entry P00634, version 1 of the sequence).

The system and process of the present invention is also suitable for the production of a nucleotide of interest such as a plasmid. Instead of overexpressing the protein of interest, a nucleotide of interest is expressed in this embodiment. The nucleotide of interest may be a plasmid. In comparison its expression is not necessary to be induced but may be due to an intrinsic factor of the plasmid.

Thus, preferably the nucleic acid of interest is a plasmid, more preferably a plasmid with a high plasmid copy numbers. "Plasmid copy number" describes the average number of plasmid copies per cell. A "high" plasmid copy number describes plasmids with a plasmid copy number of at least 100, at least 200, at least 500, at least 1000 or even at least 5000.

After leaving the production reactor through the outlet, the microbial or bacterial host cells may be stored or directly processed. An exemplary process is described in WO 2004/085643, which is hereby incorporated by reference. However, isolation of nucleic acids such as plasmid DNA is well-known to a person skilled in the art. In general, the production of the nucleic acid of the invention includes the growth of the microbial/bacterial culture making use of the system or process of the invention, which is optionally followed by harvesting and lysis of the microbial/bacterial host cells and optionally the purification of plasmid DNA.

The first step of the processing usually is disintegrating the microbial/bacterial host cells by lysis, preferably alkaline lysis. The lysis reaction, in a preferred embodiment of the present invention, is performed according to methods known in the art, using an alkaline lysis solution that contains a detergent. A typical lysing solution consists of NaOH (0.2 M) and SDS (1%), but also other alkaline solutions and other detergents can be used (see e.g. WO 97/29190).

The lysing is followed by neutralization of the alkaline solution. Also this step may, in principle, be performed according to methods known per se, preferably according to methods that are gentle and can be run in a continuous and automated mode. In a preferred embodiment, in the neutralization step the lysed cell solution is mixed with the neutralizing solution. Typically a buffered solution with acidic pH and high salt concentration is used for neutralization. Preferable this solution consists of 3 M potassium acetate (KAc) at pH 5.5. But also other neutralizing salts can be used or added.

The plasmid DNA may then be precipitated by adding an aqueous solution comprising about 70% ethanol. By centrifugation, the nucleic acids may be pelleted and washed by aspirating the supernatant, resuspending the nucleic acid comprising pellet in the aqueous solution comprising about 70% ethanol followed by pelleting by centrifugation again. After washing, the pelleted nucleic acid may be dried.

Alternatively, or additionally to this process, also a nucleic-acid binding resin in form of a column may be used. Before capturing/purification by means of a resin, it may be necessary to adjust the parameters of the solution (like salt composition, conductivity, pH-value) to ensure binding of the desired biomolecule to the chromatographic support, usually a resin (this step is, in the meaning of the present invention, termed "conditioning step"). The simplest conditioning procedure is dilution of the cleared lysate with water or low salt buffer, especially in case the chromatographic resin in the subsequent capture step is achieved by anion exchange chromatography (WO 97/29190 AI). Furthermore, in particular when hydrophobic interaction chromatography is used as first purification step, a high concentration salt solution may be added and the possibly resulting precipitate (which is present if a certain salt concentration in the solution is exceeded) separated by filtration or centrifugation (WO 02/04027). In the case ammonium sulfate is used in high concentrations, this treatment reduces the RNA content (WO 98/11208).

For capturing and purification several steps are applied to obtain a highly purified biomolecule which meets the requirements for pharmaceuticals. As for the previous steps, enzymes, detergents and organic solvents should be avoided. Isolation and purification are performed according to methods known in the art, in particular by a combination of different chromatographic techniques (anion exchange chromatography AIEC, hydrophobic interaction chromatography HIC, size exclusion chromatography (SEC), ultra(dia)filtration, filtration or precipitation and extraction. A method that may advantageously be used, in particular for obtaining pDNA for therapeutic applications, comprises a combination of two steps that are based on different chromatographic principles, in which either of the two steps is selected from hydrophobic interaction chromatography (HIC), polar interaction chromatography (PIC) and anion exchange chromatography (AIEC) and in which at least in one of the two steps, preferably in both steps, the chromatographic support is a porous monolithic bed, preferably a rigid methacrylate-based monolith in the form of a monolithic column. Suitable monolithic columns are commercially available under the trademark CLM® from BIA Separations). This purification process may advantageously be performed with a chromatographic support in the form of a single monolithic bed comprising a tube-in-a-tube system, the outer and inner tube carrying different functional moieties. In such a system one of the monolithic tubes represents the support for the chromatographic principle of one step and the other tube represents the support for the chromatographic principle of the other step. Preferably, the capturing/purification step can be operated in a batch wise mode or in a quasi-continuous or continuous mode, employing technologies such as annular chromatography, carousel chromatography or a simulated moving.

The system of the present invention is not only suitable for protein production but can also be used for the continuous production of a compound of interest (see Example 3). This method may be used to convert a precursor compound to the compound of interest. Alternatively or additionally, the method can also be used to produce a compound of interest based on the nutrients already provided in the medium. Accordingly, the present invention also relates to a method for the (continuous) production of a compound of interest, comprising culturing the bacterial host cell as defined herein in the system of the invention and optionally adding a compound that is to be converted and/or used by said bacterial host cell for the production of said compound of interest to the seed and/or production reactor.

The term "compound of interest" as used herein may be but is not limited to precursors or building block molecules for plastics such as conversion of bicyclo[3.2.0]-hept-2-en-6-one to lactones, alcohols, such as conversion of prochiral carbonyl compounds to chiral, conversion of ferulic acid to coniferyl aldehyde to coniferyl alcohol, or conversion of eugenol to ferulic acid to coniferyl alcohol to vanillin.

In one embodiment, the compound of interest is lycopene. Here, the host cell can be genetically modified to further comprise enzymes of a lycopene producing pathway. In one illustrative example for such a lycopene producing pathway, the bacterial host cell is genetically modified to comprise the gene(s) crtI, and optionally crtB, and/or crtE. Preferably, said genes are from *C. glutamicum*, more preferably crtE comprises or consists of SEQ ID NO: 18 or a functional homolog thereof, crtB comprises or consists of SEQ ID NO: 19 or a functional homolog thereof and crtI comprises or consists of SEQ ID NO: 20 or a functional homolog thereof. A "functional homolog" is a nucleic acid having at least 80% sequence identity, at least 85% sequence identity, at least 90% sequence identity, at least 95% sequence identity or at least 99% sequence identity. The protein encoded by a functional homolog preferably has an activity, which has at least 80%, at least 85%, at least 90%, at least 95% or at least 99% of the activity of the protein being expressed by SEQ ID NO: 18, 19 or 20, respectively. In case the bacterial host cell comprises any one or all of SEQ ID NO: 18, 19 or 20 or a functional homolog thereof, it is preferably not necessary to add a compound to be converted.

The system of the present invention can also be used to degrade plastic materials such as polyesters. Polyester is a category of polymers that contain the ester functional group in every repeat unit of their main chain. Polyesters include naturally occurring chemicals, such as in the cutin of plant cuticles, as well as synthetics such as polybutyrate. An illustrative example of a polymer is Polyethylene terephthalate (PET). Accordingly, the compound to be converted may be polyester such as Polyethylene terephthalate (PET) and the compound of interest can be the corresponding polyester monomer such as mono-2-hydroxyethyl terephthalate (MHET). To enable the bacterial host cell to convert PET into its monomer, it may be genetically modified to comprise a PETase. PETases are an esterase class of enzymes that catalyze the hydrolysis of polyethylene terephthalate (PET) plastic to monomeric mono-2-hydroxyethyl terephthalate (MHET). Illustrative examples include lipases, esterases, and cutinases. PETase exhibits shared qualities with both lipases and cutinases in that it possesses an a/8-hydrolase fold; although, the active-site cleft observed in PETase is more open than in cutinases. The *Ideonella sakaiensis* PETase is similar to dienelactone hydrolase.

The present invention also relates to the following items:

1. System for use in continuous production of a protein of interest or a nucleotide of interest by a bacterial host cell, wherein the bacterial host cell comprises under the control of a first inducible promoter a nucleotide sequence encoding a protein from a phage which inhibits growth of said bacterial host cell, comprising (a) a seed reactor comprising said bacterial host cell in an uninduced state with respect to the nucleotide sequence encoding a protein from a phage which inhibits growth of said bacterial host cells, the seed reactor having at least one inlet and at least one outlet, and (b) at least one production reactor comprising said bacterial host cells in an induced state with respect to the nucleotide sequence encoding a protein from a phage which inhibits growth of said bacterial host cells, each production reactor having at least one inlet and at least one outlet, wherein an inlet of the production reactor is connected to an outlet of the seed reactor.

2. The system of item 1, wherein the bacterial host cell comprises a nucleotide encoding the protein of interest or the nucleotide of interest.

3. The system of item 1 or 2 wherein the protein of interest or the nucleotide of interest is produced in at least one production reactor.

4. The system of any one of the preceding items, wherein said nucleotide of interest encodes one or more proteins of interest.

5. The system of any one of the preceding items, wherein said nucleotide is a nucleic acid molecule.

6. The system of item 5, wherein said nucleic acid molecule is a plasmid, minichromosome, or RNA.

7. The system of any one of the preceding items, wherein said nucleotide of interest or said nucleotide encoding the protein of interest is under the control of a second inducible promoter or under the control of a constitutive promoter.

8. The system of any one of the preceding items, wherein the promoter of said heterologous nucleotide of interest is recognized by an RNA polymerase which is heterologous for said bacterial host cell, said heterologous RNA polymerase is encoded by a nucleotide sequence comprised by said bacterial host cell.

9. The system of item 8, wherein said RNA polymerase is bacteriophage T3 RNA polymerase, T7 bacteriophage RNA polymerase, engineered orthogonal T7 RNA polymerase, bacteriophage SP6 RNA polymerase or bacteriophage Xp10 RNA polymerase.

10. The system of item 8 or 9, wherein said nucleotide sequence encoding said RNA polymerase is under the control of a third inducible promoter or under the control of a constitutive promoter.

11. The system of any one of the preceding items, wherein said first, second or third inducible promoter is regulated by arabinose, IPTG, tryptophan, xylose, lactose, rhamnose, phosphate, propionate, benzoic acid, phage lambda cl protein or heat.

12. The system of item 11, wherein said first, second or third promoter are different.

13. The system any one of the preceding items, wherein said bacterial host cell has a non-functional arabinose operon.

14. The system of any one of the preceding items, wherein said bacterial host cell is *E. coli*, preferably *E. coli* B-lineage.

15. The system of any one of the preceding items, wherein growth is inhibited by inhibiting transcription, DNA-replication and/or cell division.

16. The system of any one of the preceding items, wherein said phage protein is (i) a protein which inhibits bacterial host cell RNA polymerase, wherein said protein is (a) a protein having the amino acid sequence shown in Seq Id No: 1 or a fragment thereof which inhibits bacterial host cell RNA polymerase; or (b) a protein having an amino acid sequence which has an identity of 40% or more to the amino acid sequence shown in Seq Id No: 1 and which inhibits bacterial host cell RNA polymerase;

(ii) a protein which inhibits bacterial host cell RNA polymerase, wherein said protein is (a) a protein having the amino acid sequence shown in Seq Id No: 2 or a fragment thereof which inhibits bacterial host cell RNA polymerase; or (b) a protein having an amino acid sequence which has an identity of 40% or more to the amino acid sequence shown in Seq Id No: 2 and which inhibits bacterial host cell RNA polymerase;

(iii) a protein which phosphorylates bacterial host cell RNA polymerase, wherein said protein is (a) a protein having the amino acid sequence shown in Seq Id No: 3 or a fragment thereof which phosphorylates bacterial host cell RNA polymerase; or (b) a protein having an amino acid sequence which has an identity of 40% or more to the amino acid sequence shown in Seq Id No: 3 and which phosphorylates bacterial host cell RNA polymerase;

(iv) a protein which inhibits bacterial host cell DNA replication, wherein said protein is (a) a protein having the amino acid sequence shown in Seq Id No: 4 or a fragment thereof which inhibits bacterial host cell DNA replication; or (b) a protein having an amino acid sequence which has an identity of 40% or more to the amino acid sequence shown in Seq Id No: 4 and which inhibits bacterial host cell DNA replication;

(v) a protein which inhibits bacterial host cell DNA replication, wherein said protein is (a) a protein having the amino acid sequence shown in Seq Id No: 5 or a fragment thereof which inhibits bacterial host cell DNA replication; or (b) a protein having an amino acid sequence which has an identity of 40% or more to the amino acid sequence shown in Seq Id No: 5 and which inhibits bacterial host cell DNA replication; or (vi) a protein which inhibits bacterial host cell DNA replication, wherein said protein is (a) a protein having the amino acid sequence shown in Seq Id No: 6 or a fragment thereof which inhibits bacterial host cell DNA replication; or (b) a protein having an amino acid sequence which has an identity of 40% or more to the amino acid sequence shown in Seq Id No: 6 and which inhibits bacterial host cell DNA replication;

(vii) a protein which inhibits bacterial host cell RNA polymerase, wherein said protein is (a) a protein having the amino acid sequence shown in Seq Id No: 7 or a fragment thereof which inhibits bacterial host cell RNA polymerase; or (b) a protein having an amino acid sequence which has an identity of 40% or more, such as 50%, 60%, 70%, 80% or 90% to the amino acid sequence shown in Seq Id No: 7 and which inhibits bacterial host cell RNA polymerase;

(viii) a protein which causes host transcription shut-off, wherein said protein is (a) a protein having the amino acid sequence shown in Seq Id No: 8, 9, 10, 11, 12, 13, 14 or a fragment thereof which causes host transcription shut-off;

(b) a protein having an amino acid sequence which has an identity of 40% or more, such as 50%, 60%, 70%, 80% or 90% to the amino acid sequence shown in Seq Id No: 8, 9, 10, 11, 12, 13 or 14 and which causes host transcription shut-off; or (ix) a protein which inhibits bacterial host cell RNA polymerase, wherein said protein is (a) a protein having the amino acid sequence shown in Seq Id No: 17 or a fragment thereof which inhibits bacterial host cell RNA polymerase; or (b) a protein having an amino acid sequence which has an identity of 40% or more to the amino acid sequence shown in Seq Id No: 17 and which inhibits bacterial host cell RNA polymerase.

17. The system of any one of the preceding items, wherein the bacterial host cell is cultured in an uninduced state with respect to the nucleotide sequence encoding a protein from a phage which inhibits growth of said bacterial host cell in the seed reactor for biomass production.

18. The system of any one of the preceding items, wherein the bacterial host cell is cultured in an induced state with respect to the nucleotide sequence encoding a protein from a phage which inhibits growth of said bacterial host cell in the production reactor for production of said nucleotide sequence of interest by said bacterial host cells.

19. The system of any one of the preceding items, further comprising (c) a means for operating the seed and production reactors as linked chemostats or turbidostats.

20. The system of any one of the preceding items, whereby the seed reactor outflow serves as inflow to the production reactor.

21. The system of any one of the preceding items, wherein the seed reactor does not comprise or does not essentially comprise an inducer for the first inducible promoter.

22. The system of any one of the preceding items, wherein at least one of the at least one production reactor comprises an inducer for the first inducible promoter.

23. The system of any one of the preceding items, wherein at least one of the at least one production reactor comprises an inducer for the second inducible promoter.

24. The system of any one of the preceding items, wherein the first inducible promoter and the second inducible promoter can be induced by the same inducer.

25. The system of any one of the preceding items, wherein the seed reactor comprises a means for regulating pH.

26. The system of any one of the preceding items, wherein the seed reactor comprises a means for regulating dissolved oxygen.

27. The system of any one of the preceding items, wherein the seed reactor comprises a means for regulating temperature.

28. The system of any one of the preceding items, wherein the seed reactor comprises a gas inlet and a gas outlet and a means for regulating the gas flow.

29. The system of any one of the preceding items, wherein the at least one production reactor comprises a means for regulating pH.

30. The system of any one of the preceding items, wherein the at least one production reactor comprises a means for regulating dissolved oxygen.

31. The system of any one of the preceding items, wherein the at least one production reactor comprises a means for regulating temperature.

32. The system of any one of the preceding items, wherein the at least one production reactor comprises a gas inlet and a gas outlet and a means for regulating the gas flow.

33. The system of any one of the preceding items, wherein the at least one production reactor comprises a biomass sensor.

34. The system of any one of the preceding items comprising a first feed container containing a first feed medium comprising a carbon source, wherein the first feed container is operably connected to an inlet of the seed reactor, wherein the system preferably comprises means for regulating feed flow from the first feed container to the seed reactor.

35. The system of any one of the preceding items comprising a second feed container containing a second feed medium comprising a carbon source, wherein the second feed container is operably connected to an inlet of the at least one production reactor, wherein the system preferably comprises means for regulating feed flow from the second feed container to the at least one production reactor.

36. The system of any one of the preceding items, wherein an outlet of the seed reactor and an outlet of a second feed reactor are connected to a mixing chamber, wherein an outlet of the mixing chamber is connected to an inlet of the at least one production reactor.

37. The system of any one of the preceding items, wherein the seed reactor is a stirred tank reactor or plug flow reactor.

38. The system of any one of the preceding items, wherein the at least one production reactor is a stirred tank reactor or a plug flow reactor.

39. The system of any one of the preceding items, wherein the seed reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

40. The system of any one of the preceding items, wherein the at least one production reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

41. The system of any one of the preceding items, wherein the volume ratio of the seed reactor to the at least one production reactor is from about 1:10 to about 2:1, from about 1:5 to about 2:1, from about 1:2 to about to about 2:1, from about 1.5:1 to about 1:1.5, or about 1:1.

42. The system of any one of the preceding items, wherein the at least one production reactor comprises a culture medium comprising cells with a biomass concentration from about 10 to about 90 g/L cell dry weight, preferably from about 20 to about 80 g/L cell dry weight, preferably from about 30 to about 70 g/L cell dry weight, preferably from about 35 to about 60 g/L cell dry weight.

43. A continuous fermentation process for the production of a protein of interest or a nucleotide of interest by a bacterial host cell, wherein the bacterial host cell comprise under the control of a first inducible promoter a nucleotide sequence encoding a protein from a phage which inhibits growth of said bacterial host cell, comprising (a) culturing said bacterial host cell in an uninduced state with respect to the nucleotide sequence encoding a protein from a phage which inhibits growth of said bacterial host cell in a seed reactor;

(b) transferring at least an amount of the bacterial host cells obtained in (a) from said seed reactor to a production reactor; and (c) culturing said bacterial host cells in said production reactor in an induced state with respect to the nucleotide sequence encoding a protein from a phage which inhibits growth of said bacterial host cells;

wherein the seed reactor and production reactor is configured as an independent continuous fermentor and wherein the seed reactor and production reactor are connected with each other.

44. The process of item 43, wherein (a) is for biomass production.

45. The process of item 43 or 44, wherein in (c) growth of said bacterial host cells is inhibited by culturing said bacterial host cells in an induced state with respect to the nucleotide sequence encoding a protein from a phage which inhibits growth of said bacterial host cells, while said nucleotide of interest or said protein of interest is produced.

46. The process of any one of items 43 to 45, wherein the bacterial host cell comprises the nucleotide of interest or a nucleotide encoding the protein of interest.

47. The process of any one of items 43 to 46, wherein said nucleotide of interest encodes one or more proteins of interest.

48. The process of any one of items 43 to 47, wherein said nucleotide is a nucleic acid molecule.

49. The process of item 48, wherein said nucleic acid molecule is a plasmid, minichromosome, or RNA.

50. The process of any one of items 43 to 49, wherein said nucleotide of interest or said nucleotide encoding the protein of interest is under the control of a second inducible promoter or under the control of a constitutive promoter.

51. The process of any one items 43 to 50, wherein the promoter of said heterologous nucleotide sequence of is recognized by an RNA polymerase which is heterologous for said bacterial host cell, said heterologous RNA polymerase is encoded by a nucleotide sequence comprised by said bacterial host cell.

52. The process of item 51, wherein said heterologous RNA polymerase is bacteriophage T3 RNA polymerase, T7 bacteriophage RNA polymerase, engineered orthogonal T7 RNA polymerase, bacteriophage SP6 RNA polymerase or bacteriophage Xp10 RNA polymerase.

53. The process of item 51 or 52, wherein said nucleotide sequence encoding said heterologous RNA polymerase is under the control of a third inducible promoter or under the control of a constitutive promoter.

54. The process of any one of items 43 to 53, wherein said first, second or third inducible promoter is regulated by arabinose, IPTG, tryptophan, xylose, lactose, rhamnose, phosphate, propionate, benzoic acid, phage lambda cl protein or heat.

55. The process of item 54, whereby said first, second or third promoter are different.

56. The process of any one of items 43 to 55, wherein said bacterial host cell has a non-functional arabinose operon.

57. The process of any one of items 43 to 56, wherein said bacterial host cell is *E. coli*, preferably *E. coli* B-lineage.

58. The process of any one of items 43 to 57, wherein (a) further comprises culturing said bacterial host cells in an uninduced state with respect to the nucleotide sequence encoding a protein from a phage which inhibits growth of said bacterial host cells in culture medium in a production reactor for biomass production.

59. The process of any one of items 43 to 58, wherein (c) further comprises inducing said first inducible promoter controlling said nucleotide sequence encoding a protein from a phage which inhibits growth of said bacterial host cells.

60. The process of any one of items 43 to 59, wherein (b) or (c) comprises inducing said second inducible promoter controlling said nucleotide of interest or said nucleotide encoding the protein of interest.

61. The process of any one of items 43 to 60, wherein (a), (b) or (c) comprises inducing said third inducible promoter controlling said nucleotide sequence encoding said heterologous RNA polymerase.

62. The process of any one of items 43 to 61, further comprising (d) harvesting the product resulting from the production of said nucleotide sequence of interest.

63. The process of any one of items 43 to 62, wherein the seed reactor does not comprise or does not essentially comprise an inducer for the first inducible promoter.

64. The process of any one of items 43 to 63, wherein at least one of the at least one production reactor comprises an inducer for the first inducible promoter.

65. The process of any one of items 43 to 64, wherein at least one of the at least one of the at least one production reactor comprises an inducer for the second inducible promoter.

66. The process of any one of items 43 to 65, wherein the first inducible promoter and the second inducible promoter can be induced by the same inducer.

67. The process of any one of items 43 to 66, wherein pH is regulated in the seed reactor.

68. The process of any one of items 43 to 67, wherein dissolved oxygen is regulated in the seed reactor.

69. The process of any one of items 43 to 68, wherein temperature is regulated in the seed reactor.

70. The process of any one of items 43 to 69, wherein gas flow is regulated in the seed reactor.

71. The process of any one of items 43 to 70, wherein the biomass concentration is regulated in the seed reactor by feed inflow and/or biomass outflow.

72. The process of any one of items 43 to 71, wherein pH is regulated in the at least one production reactor.

73. The process of any one of items 43 to 72, wherein dissolved oxygen is regulated in the at least one production reactor.

74. The process of any one of items 43 to 73, wherein temperature is regulated in the at least one production reactor.

75. The process of any one of items 43 to 74, wherein gas flow is regulated in the at least one production reactor.

76. The process of any one of items 43 to 75, wherein the at least one production reactor comprises a biomass sensor.

77. The process of any one of items 43 to 76, wherein the biomass concentration is regulated in the at least one production reactor by feed inflow, biomass inflow, and/or biomass outflow.

78. The process of any one of items 43 to 77, wherein the mean residence time of biomass in the at least one production reactor is from about 5 h to about 24 h, preferably from about 7 h to about 20 h, preferably from about 10 h to about 15 h.

79. The process of any one of items 43 to 78, comprising a first feed container containing a first feed medium comprising a carbon source, wherein the first feed container is operably connected to an inlet of the seed reactor, wherein feed flow from the first feed container to the seed reactor is preferably regulated.

80. The process of any one of items 43 to 79, comprising a second feed container containing a second feed medium comprising a carbon source, wherein the second feed container is operably connected to an inlet of the at least one production reactor, wherein feed flow from the second feed container to the at least one production reactor is preferably regulated.

81. The process of any one of items 43 to 80, wherein an outlet of the seed reactor and an outlet of a second feed reactor are connected to a mixing chamber, wherein an outlet of the mixing chamber is connected to an inlet of the at least one production reactor.

82. The process of any one of items 43 to 81, wherein the seed reactor is a stirred tank reactor or a plug flow reactor.

83. The process of any one of items 43 to 82, wherein the at least one production reactor is a stirred tank reactor or a plug flow reactor.

84. The process of any one of items 43 to 83, wherein the seed reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

85. The process of any one of items 43 to 84, wherein the at least one production reactor has a volume of at least about 0.25 L, at least about 0.5 L, at least about 1 L, at least about 5 L, at least about 10 L, at least about 25 L, at least about 50 L, at least about 100 L, at least about 250 L, at least about 500 L, or at least about 1000 L.

86. The process of any one of items 43 to 85, wherein the volume ratio of the seed reactor to the at least one production reactor is from about 1:10 to about 2:1, from about 1:5 to about 2:1, from about 1:2 to about to about 2:1, from about 1.5:1 to about 1:1.5, or about 1:1.

87. The process of any one of items 43 to 86, wherein the at least one production reactor comprises a culture medium comprising cells with a biomass concentration from about 10 to about 90 g/L cell dry weight, preferably from about 20 to about 80 g/L cell dry weight, preferably from about 30 to about 70 g/L cell dry weight, preferably from about 35 to about 60 g/L cell dry weight.

88. The process of any one of items 43 to 87, wherein the bacterial host cells in the at least one production reactor is genetically stable for at least about 5 days, preferably at least about 7 days, preferably at least about 10 days.

89. The process of any one of items 43 to 88, wherein the process is operated for at least about 5 days, preferably at least about 7 days, preferably at least about 10 days.

It must be noted that as used herein, the singular forms "a", "an", and "the", include plural references unless the context clearly indicates otherwise. Thus, for example, reference to "an expression cassette" includes one or more of the expression cassettes disclosed herein and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

The term "about" or "approximately" as used herein means within 20%, preferably within 10%, and more preferably within 5% of a given value or range. It includes also the concrete number, e.g., about 20 includes 20.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well-known in the art. Generally, nomenclatures used in connection with techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N. Y. (2001); Ausubel et al., Current Protocols in Molecular Biology, J, Greene Publishing Associates (1992, and Supplements to 2002); Handbook of Biochemistry: Section A Proteins, Vol 11976 CRC Press; Handbook of Biochemistry: Section A Proteins, Vol II 1976 CRC Press. The nomenclatures used in connection with, and the laboratory procedures and techniques of, molecular and cellular biology, protein biochemistry, enzymology and medicinal and pharmaceutical chemistry described herein are those well-known and commonly used in the art.

EXAMPLES

The following Examples illustrate the invention, but are not to be construed as limiting the scope of the invention.

Example 1: Continuous Fermentation Process for Green Fluorescent Protein (GFP)

Figure 1:
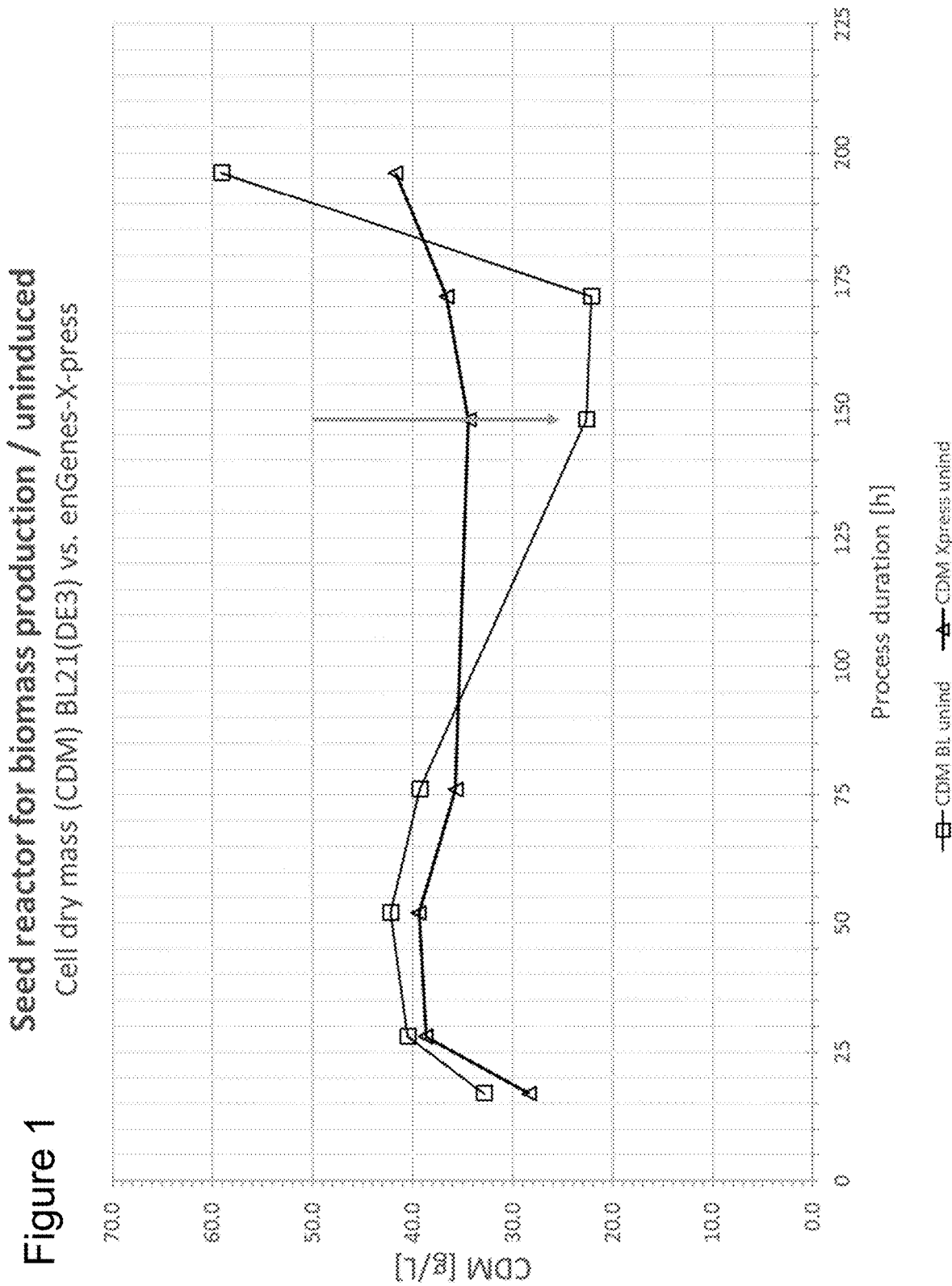
FIG. 1: Cell dry mass concentration [CDM, in g/L] for the seed reactor (1 stage) for biomass concentration (uninduced, without addition of IPTG and L-arabinose) in Example 1. Empty squares (□) shows BL21(DE3)pET30a<GFP> whereas empty triangle (Δ) shows enGenes-X-press pET30a<GFP>. CDM was followed for a period of 196 h, corresponding to 8 days. Abrupt population collapse is indicated by a blue arrow. Here, a drop in CDM is observable for BL21(DE3)pET30a<GFP> after 150 h in chemostat mode, not observable for enGenes-X-press pET30a<GFP>, thereby improving stability and productivity of the continuous production process unexpectedly even in at the seed stage reactor.
Figure 2:
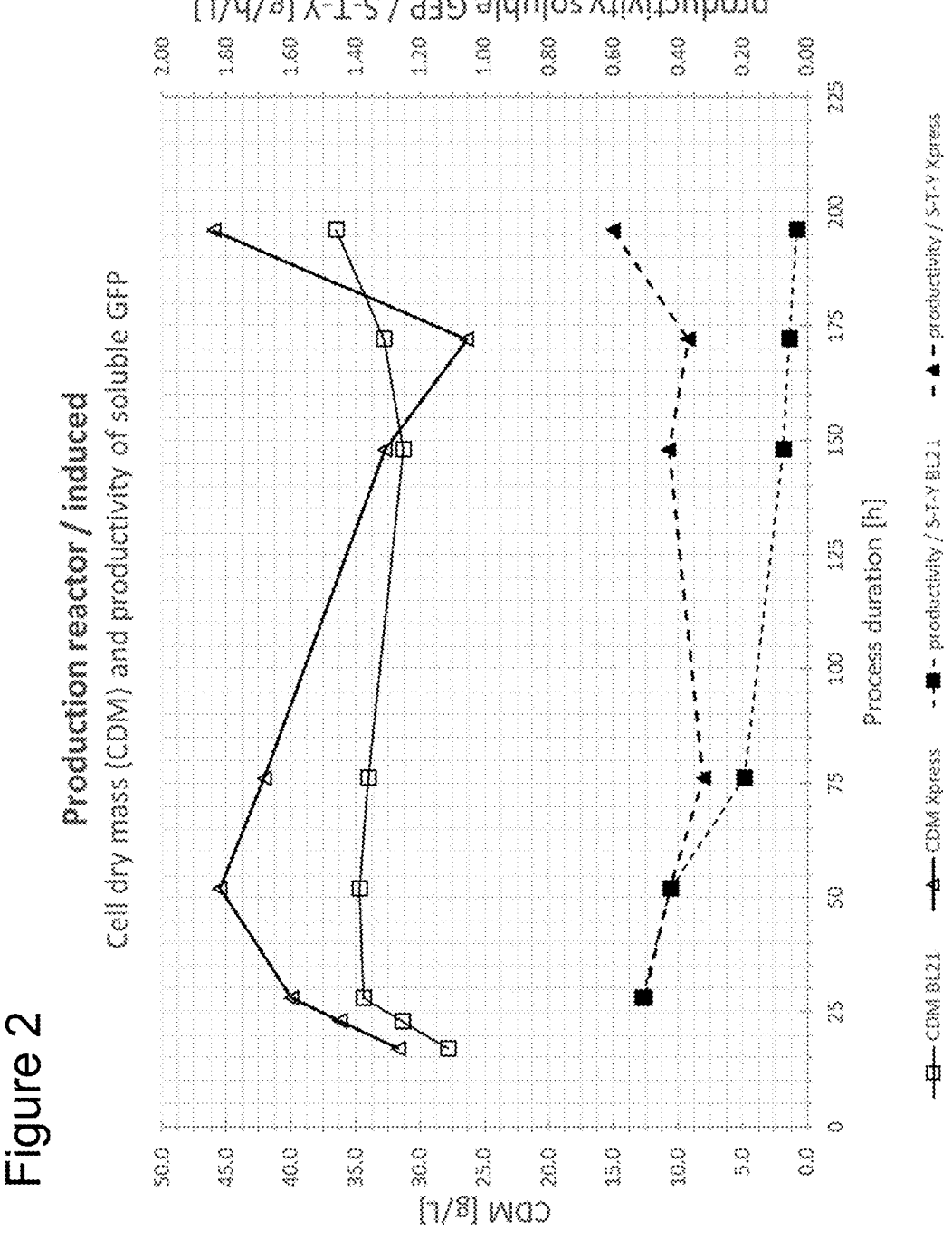
FIG. 2: Cell dry mass concentration [CDM, in g/L] and productivity for total GFP [g/h] for the production reactor (2nd stage) (induced, with addition of IPTG and L-arabinose in case of X-press) in Example 1. Empty squares (□) shows BL21(DE3)pET30a<GFP> whereas empty triangle (Δ) shows enGenes-X-press pET30a<GFP>. Dashed line with filled square (■) shows BL21(DE3)pET30a<GFP> whereas dashed line with filled triangle (▲) shows enGenes-X-press pET30a<GFP>. CDM and total volumetric yield were followed for a period of 196 h, corresponding to 8 days. enGenes-X-press pET30a<GFP> shows a 20-fold increase in total GFP productivity (0.6 g/L/h vs. 0.03 g/L/h) after 196 h operated in 2-stage chemostat mode in comparison to BL21(DE3)pET30a<GFP>.

To test the ability of the enGenes-X-press strain for continuous growth decoupled recombinant protein production the fluorescent model protein GFP was employed. The two stage continuous fermentation experiments were carried out using the host *E. coli* strain BL21(DE3) as a reference strain, i.e. a strain that does not comprise under the control of a first inducible promoter a nucleotide sequence encoding a protein from a phage which inhibits growth of said bacterial host cell. The model protein GFP is expressed from the pET30a plasmid in the reference strain. The reference strain is thus called BL21(DE3)pET30a<GFP> herein. The enGenes-X-press strain is used as an example of bacterial host cell that comprises under the control of a first inducible promoter a nucleotide sequence encoding a protein from a phage which inhibits growth of said bacterial host cell as required by the invention. The difference between enGenes-X-press and an *E. coli* BL21(DE3) is the following: araABCD is knocked out, Gp2 is integrated at the attTn7 site and under the control of the arabinose-inducible promoter of araB. The genotype of enGenes-X-press can therefore be described as BL21(DE3)::TN7(Gp2ΔAra) For protein production, enGenes-X-press has been transformed with a pET30a plasmid comprising GFP (SEQ ID NO: 15), leading to a genotype of BL21(DE3)::TN7(Gp2ΔAra)pET30<GFP> or, in short, enGenes-X-press pET30a<GFP>. enGenes-X-press pET30a<GFP> was generated according to WO 2016/174195, hereby incorporated by reference. As shown in FIGS. 1 and 2, the use of a enGenes-X-press instead of "standard" BL21(DE3) in a in a continuous fermentation process of the invention provides for a significant increase in productivity (space-time-yield) in comparison to "standard" continuous fermentation processes known in prior art.

Figure 3:
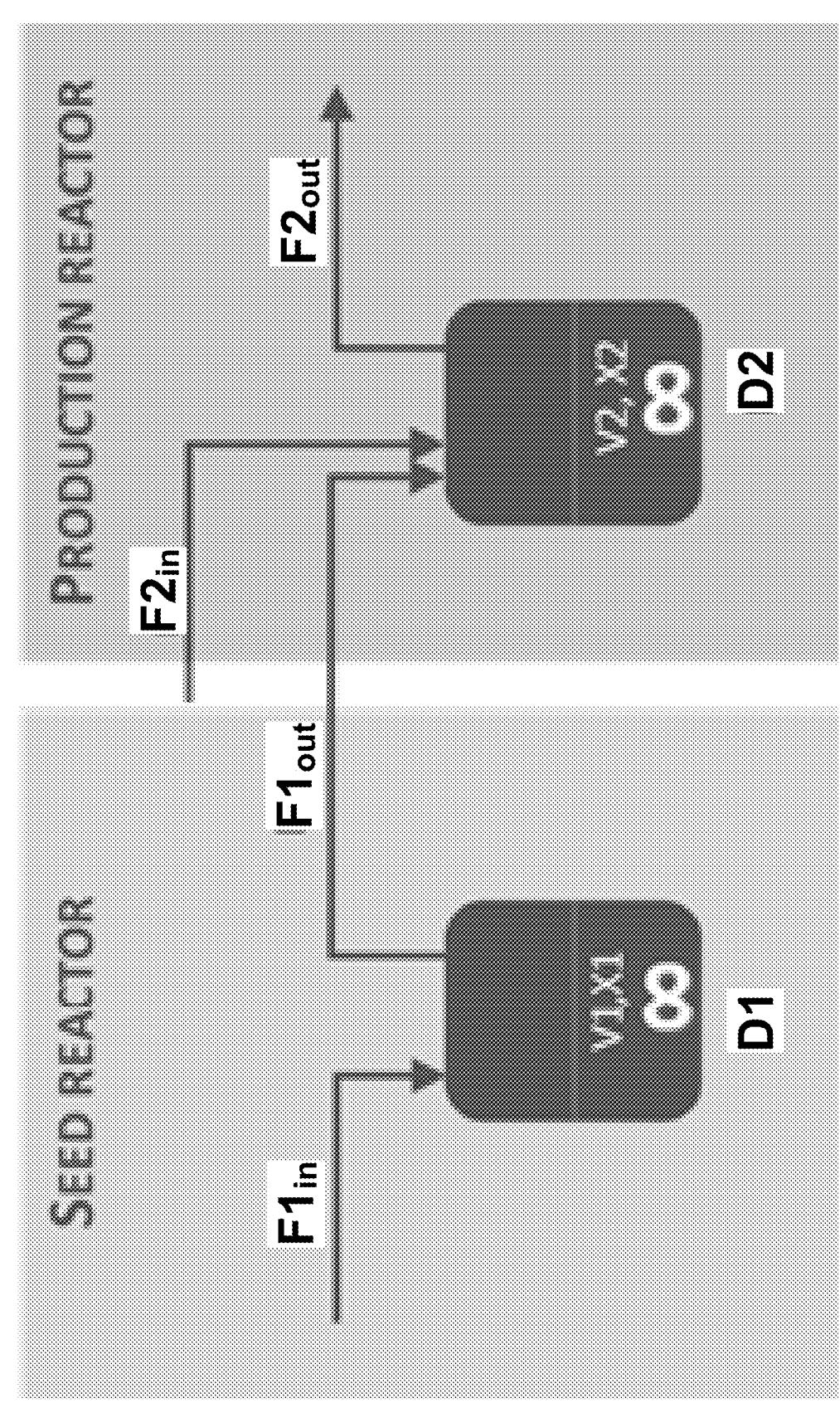
FIG. 3: Schematic overview of the 2 stage process of the invention. $F1_{IN}$ is indicative of the feed medium flow into the seed vessel with a volume V1 and to achieve a biomass concentration of X1; $F1_{OUT}$ is indicative of the volume stream from the seed vessel to the production vessel, to achieve the volume V2 and the biomass concentration X2.

The design of this 2 stage chemostat cultivation processes with a seed and a production bioreactor is shown in FIG. 3. In both bioreactors a batch process followed by a fed-batch phase was conducted. The batch volume was set to 600 mL and the batch medium used allowed for production of 5 g CDM, the feed volume was set to 460 mL with medium designed to produce another 27 g of CDM which corresponds to a final CDM concentration of 30 g/L. In a next step the seed bioreactor was shifted to chemostat mode with a dilution rate of 0.05 h$^{-1}$. The medium used as continuous feed to reactor (F1$_{in}$) provide nutrients to maintain a CDM concentration of 40 g/L. The outflow from the seed bioreactor (F1$_{out}$) represents one of the feeds to the production bioreactor. To provide the carbon source required to maintain metabolic activity of the induced system in the production reactor, a second medium feed with a flow rate of 11.31 mL/h and a glucose concentration of 400 g/L was introduced. To operate the production reactor at the same dilution rate of 0.05 h$^{-1}$ the outflow F1$_{out}$ was started at the timepoint when working volume of 1260 mL was reached in the production bioreactor. Temperature was stabilized at 30° C. The culture in the production vessel was induced by either adding 20 μmol IPTG/g CDM (BL21/DE3) strain) or 20 μmol IPTG/g CDM and 100 mM L-arabinose (enGenes-X-press strain) to the medium fed to the production reactor. GFP, accumulated in soluble and insoluble form was quantified via ELISA (soluble form) and SDS PAGE for the insoluble fraction according to Reischer et al. (2004) Journal of Biotechnology, 108(2):115-125, incorporated hereby by reference. Cell dry mass CDM was determined by centrifugation of 10 mL of cell suspension. The minimal medium used for cultivations contained 3 g KH$_2$PO$_4$ and 6 g K$_2$HPO$_4$·3H$_2$O per litre; these concentrations provided the required buffer capacity and served as sources of P and K. The other components were added in relation to the theoretical grams of CDM to be produced (calculated for 5 g in batch-phase and 136 g CDM in feed-phase, based on the constant glucose yield coefficient YX/S of 0.3 g/g): 0.25 g sodium citrate (trisodium salt·2H$_2$O; ACROS organics), 0.10 g MgSO$_4$.7H$_2$O, 0.02 g CaCl$_2$·2H$_2$O, 50 μL trace element solution, and 3 g glucose·H$_2$O. The trace element solution was prepared in 5 N HCl and included 40 g/L FeSO$_4$·7H$_2$O, 10 g/L MnSO$_4$·H$_2$O, 10 g/L AlCl$_3$·6H$_2$O, 4 g/L CoCl$_2$ (Fluka), 2 g/L ZnSO$_4$·7H$_2$O, 2 g/L Na$_2$MoO$_2$·2H$_2$O, 1 g/L CuCl$_2$·2H$_2$O, and 0.5 g/L H$_3$BO$_3$. We also added 4 mg CuCl$_2$.2H$_2$O and 3.2 mg ZnSO$_4$·7H$_2$O per g CDM. To accelerate initial growth of the population, the complex component yeast extract (0.15 g per g theoretical CDM) was added to the minimal medium to obtain the batch medium.

The inventors observed an abrupt population collapse in the seed reactor with BL21(DE3)pET30a<GFP> indicated by a significant decrease in CDM after 148 h process time (from 40 g/L to 20 g/L CDM, FIG. 1) whereas that collapse was surprisingly not observable for enGenes-X-press pET30a<GFP> cells (engineered to allow growth decoupling of protein production and cell growth using the T7 phage derived Gp2 protein that is under the control of an arabinose promoter, integrated into the *E. coli* genome at the attTn7 site, generated according to WO 2016/174195, hereby incorporated by reference). GFP productivity in the 2$^{nd}$ stage production reactor was more constant for the X-press strain (range between 0.3 g/h and 0.6 g/h) whereas for the reference BL21(DE3) the inventors observed a steady decline in total GFP yields (from 0.5 g/h to 0.03 g/h, FIG. 2). Even though the CDM of the reference strain BL21(DE3) in the seed reactors seems to recover at 200 h, the productivity of BL21(DE3) remains low with a continuous decreasing trend which is in contrast to the enGenes-X-press cells. This drop in GFP productivity in BL21(DE3) can be explained on the population level by doing FACS analysis, measuring the fluorescence intensity of individual cells at 488 nm extinction. The results in FIG. 4 show FACS histograms of BL21(DE3)pET30a<GFP> strain (left hand side) and X-press pET30a<GFP> (right hand side) in the seed stage reactor and clearly shows that the GFP positive population nearly disappears after the drop in CDM (from 148 h to 196 h). In contrast to this observation the population of X-press cells stays more uniform, able to maintain a high level of GFP positive cells, even in the seed reactor stage. This development at the seed reactor stage for biomass production is then also reflected at the production stage reactor (FIG. 5) where the peak for GFP positive cells begins to shift for BL21(DE3)pET30a<GFP> and nearly disappears at the end of process (196 h). This is also in good agreement with the low GFP productivity for BL21(DE3) at the end of the process, overall indicating a lower population stability of BL21(DE3) strains compared to growth-decoupled enGenes-X-press cells. The growth-decoupled protein production in the production reactor stage of the invention prevents or reduces manifestation of faster growing, plasmid-free, non-producing cells and thereby stabilizes the production system due to the lack of genetic changes being the consequence of adaptive evolution. Adaptive evolution is not at play in a population of non-dividing cells, a phenomenon also known as genetic instability.

The growth-decoupled enGenes-X-press strain produced about 90 g of GFP over the course of 196 h. The reference *E. coli* strain BL21(DE3) produced less than 5 g of GFP over the course of their respective cultivations, with a steadily declining productivity. In addition to producing lower overall peak levels of test protein, the reference *E. coli* strain BL21(DE3) was only capable of sustaining peak levels of production for a few days, whereas the enGenes-X-press strain sustained high expression levels throughout the entire fermentation. Importantly, the enGenes-X-press fermentations were not subject to culture collapse in the seed reactor nor the production reactor (culture collapse was always observed at the seed reactor level for the reference strain), indicating the enhanced genetic stability of the X-press strain itself.

The described growth-decoupled 2-stage continuous production system is capable of producing at least 20 times more product than the same 2-stage cultivation system (using a typical *E. coli* strain) in non-growth decoupled mode. The used *E. coli* enGenes-X-press strain that allows growth-decoupled production in the $2^{nd}$ stage production bioreactor showed improved genetic stability and population stability unanticipated in the $1^{St}$ stage seed bioreactor. The improved genetic stability of the fermentation organism improves the longevity and did not show signs of population collapse in the observed timespan. This unique growth-decoupled 2-stage fermentation process results in a highly productive stable platform for making proteins and other fermentation products at high levels relative to current strains used, not applicable for genetic decoupling of recombinant product formation.

Example 2: Continuous Fermentation Process for SpA (Protein A) Protein from *Staphylococcus aureus*

This example is essentially carried out as described in example 1, while using SpA having a periplasmic leader sequence instead of GFP as model protein. Accordingly, the reference strain is *E. coli* BL21(DE3)pET30a<pelbB-SpA> and the growth-decoupled bacterial host cell of described herein is enGenes-X-press pET30<pelB-SpA>. The nucleic acid sequence of pelB-SpA used in Example 2 is shown in SEQ ID NO: 16. Comparison of cell dry mass and productivity profiles of each of these strains, shown in FIGS. 6 and 7, shows that growth decoupled protein production in a 2 stage process is significantly improved in comparison to commonly used BL21(DE3) production strains.

In these experiments all strains were transformed with the same pET30a<pelbB-SpA> plasmid with kanamycin as selection marker. All strains were tested in the 2-stage system configured as shown in FIG. 3 already described in example 1. Operation conditions were identical to the experiments described in example 1. SpA concentrations were determined using an HPLC IMAC column and a His-tagged Protein A standard directly from cell free culture supernatants. Cell dry mass CDM was determined by centrifugation of 10 mL of cell suspension.

In this experiment the inventors also observed an abrupt population collapse in the seed reactor of BL21(DE3) pET30a<pelB-SpA> cells indicated by a significant decrease in CDM after 168 h (from 46 g/L to 7 g/L CDM) whereas that collapse was not observable for enGenes-X-press pET30a<pelB-SpA> cells (FIG. 6). SpA productivity in the production reactor was again constant for X-press strain at a high level ranging from 0.3 to 0.5 g/h whereas for BL21(DE3) the inventors observed a peak of 0.6 g/h after 75 h in the production phase followed by a steady decline in total SpA yields for the reference strain. This maximum SpA productivity is in coincidence with the population collapse in the seed reactor and led to breakdown of the production system since the low biomass concentrations in the seed reactor could no longer sustain the targeted biomass concentration in the production bioreactor. The reduced biomass in the production reactor will inevitably also lead to a reduced productivity.

The growth-decoupled enGenes-X-press strain produced about 120 g of SpA within the 309 h in chemostat mode (FIG. 7). The reference strain *E. coli* BL21(DE3) was only capable of sustaining peak levels of production for a few days, whereas the enGenes-X-press strain sustained peak expression throughout the entire fermentation duration. Importantly, the enGenes-X-press fermentations were again not subject to culture collapse in the seed reactor nor the production reactor (culture collapse was always observed at the seed reactor level), confirming the high stability of this system in continuous cultivation mode.

Example 3: Continuous Fermentation Process for Lycopene Production Using Lycopene Pathway Genes from *Corynebacterium glutamicum*

This example is essentially carried out as described in example 1, while using a pET-derived plasmid pET30a<crtE-crtB-crtl>cer encoding genes from *Corynebacterium glutamicum* MB001 [crtE (locus tag: cgp_0723, EC-number: 2.5.1.29, SEQ ID NO: 18); crtB (locus tag: cgp_0721, EC-number: 2.5.1., SEQ ID NO: 19); crtl (locus tag: cgp_0720, EC-number: 1.3.99., SEQ ID NO: 20)] having a. polycistronic arrangement (controlled by one T7 promoter/terminator) and three RBS (ribosomal binding sites, one for each gene). Accordingly, the reference strain is *E. coli* BL21(DE3)pET30a<crtE-crtB-crtl>cer and the growth-decoupled bacterial host cell of described herein is enGenes-X-press pET30a<crtE-crtB-crtl>cer. Comparison of cell dry mass and productivity profiles of each of these strains, shown in FIG. 8, shows that growth decoupled protein production in a 2-stage process is significantly improved in comparison to commonly used BL21(DE3) production strains.

In these experiments all strains were transformed with the same pET30a<crtE-crtB-crtl>cer plasmid with kanamycin as selection marker. All strains were tested in the 2-stage system configured as shown in FIG. 3 already described in example 1. Experiment were performed with a dilution rate of 0.1 h−1, working volume for phase 1 was 700 mL and for phase 2 1000 mL. Lycopene concentrations were determined by linear regression analysis using spectrophotometry and a lycopene standard. Lycopene has been extracted from the biomass using acetone (100%) and was measured at wavelength 460 nm using an Ultrospec 500 pro (Amersham Bioscience, UK) spectrometer. Cell dry mass (CDM) was gravimetrically determined by centrifugation of 10 mL of cell suspension. dsDNA concentration was measured using the Qubit Flurometer (Thermo Fisher Scientific) and the corresponding Qubit™ dsDNA BR Assay Kit following the manufacturer's instructions. The determined concentration in the cell free supernatant has then been normalized to cell dry mass (see FIG. 9).

In this experiment the inventors observed an decline in lycopene production after 10 doublings post induction (70 h) with BL21(DE3)pET30a<crtE-crtB-crtl>cer also indicated by a significant decrease in CDM after 70 h (from 54.0 g/L to 24.6 g/L CDM). This decrease in lycopene production and cell dry mass concentration was not observable for enGenes-X-press pET30a<crtE-crtB-crtl>cer cells (FIG. 8). Lycopene production in the production reactor was steadily increasing again for X-press strain with a final amount of 334 mg lycopene produced at the one litre scale after 310 h post induction whereas for BL21(DE3) the inventors observed a peak of 141 mg after 84 h in the production phase with already declining biomass yields. Therefore, the process was terminated after 142 h because the reduced biomass in the production reactor will inevitably also lead to a reduced productivity.

Importantly, the enGenes-X-press fermentations were again not subject to culture collapse in the seed reactor nor the production reactor. In the case of example one culture collapse or cell lysis was observed in the production rather than the seed reactor (as shown for example 1 and 2). Again, this confirms the improved stability of the enGenes-X-press strain also for the production of metabolites.

The invention claimed is:

1. A continuous fermentation process for the production of a protein of interest or a polynucleotide of interest by a bacterial host cell, wherein the bacterial host cell comprises a nucleic acid encoding a protein from a phage which inhibits growth of said bacterial host cell, said nucleic acid under the control of a first inducible promoter, wherein said protein from phage which inhibits growth of said bacterial host cell (i) inhibits bacterial host cell RNA polymerase, (ii) inhibits host cell DNA replication, or (iii) causes host cell transcriptional shut-off, wherein said first inducible promoter promotes expression of said nucleic acid, comprising (a) culturing said bacterial host cell in an uninduced state with respect to the nucleic acid encoding the protein from the phage which inhibits growth of said bacterial host cell in a seed reactor;

(b) transferring at least an amount of the bacterial host cells obtained in (a) from said seed reactor to a production reactor; and (c) culturing said bacterial host cells in said production reactor in an induced state with respect to the nucleic acid encoding the protein from the phage which inhibits growth of said bacterial host cells;

wherein the seed reactor and production reactor is configured as an independent continuous fermentor and wherein the seed reactor and production reactor are connected with each other, wherein (a), (b), and (c) occur simultaneously during at least a portion of the continuous fermentation process, and wherein the seed reactor and the production reactor are configured as linked chemostats or turbidostats.

2. The process of claim 1, wherein (a) is for biomass production.

3. The process of claim 1, wherein in (c) growth of said bacterial host cells is inhibited by culturing said bacterial host cells in an induced state with respect to the nucleotide sequence encoding a protein from a phage which inhibits growth of said bacterial host cells, while said polynucleotide of interest or said protein of interest is produced.

4. The process of claim 1, wherein the bacterial host cell comprises the polynucleotide of interest or a nucleotide encoding the protein of interest.

5. The process of claim 1, wherein said polynucleotide of interest or a polynucleotide encoding said protein of interest is under the control of a second inducible promoter or under the control of a constitutive promoter.

6. The process of claim 5, wherein said second inducible promoter or said constitutive promoter is recognized by an RNA polymerase which is heterologous for said bacterial host cell, said heterologous RNA polymerase is encoded by a nucleotide sequence comprised by said bacterial host cell.

7. The process of claim 1, wherein said bacterial host cell has a non-functional arabinose operon.

8. The process of claim 1, wherein said bacterial host cell is *E. coli*.

9. The process of claim 1, wherein (a) further comprises culturing said bacterial host cells in an uninduced state with respect to the nucleotide sequence encoding a protein from a phage which inhibits growth of said bacterial host cells in culture medium in a production reactor for biomass production.

10. The process of claim 1, further comprising (d) harvesting said protein of interest or said polynucleotide of interest.

11. The process of claim 1, wherein the bacterial host cells in the at least one production reactor is genetically stable for at least about 5 days.

12. The process of claim 1, wherein the process is operated for at least about 5 days.

13. The process of claim 1, wherein said protein from a phage which inhibits growth of said bacterial host cell has at least 80% sequence identity to a polypeptide having an amino acid sequence selected from the group consisting of SEQ ID NOs: 1-14 and 17.

14. The process of claim 13, wherein said protein has at least 90% sequence identity to a polypeptide having an amino acid sequence selected from the group consisting of SEQ ID NOs: 1-14 and 17.

15. The process of claim 1, wherein said protein from a phage which inhibits growth of said bacterial host cell is selected from the group consisting of Gp2, Nun, GP0.7, Gp6, Gp8, A*, YkzG Epsilon-Subunit, *Bacillus* phage SPO1 GP40, *Staphylococcus* phage G1 GP67, *Thermus thermophilus* phage P23-45 GP39, Enterobacteria phage PhiEco32 GP79, *Xanthomonas oryzae* bacteriophage Xp10 P7 protein, Enterobacteria phage T4 Alc protein, Enterobacteria phage T4 Asia protein, and Gp5.7.

* * * * *

SEQUENCE LISTING

<160> NUMBER OF SEQ ID NOS: 20

<210> SEQ ID NO 1
<211> LENGTH: 64
<212> TYPE: PRT
<213> ORGANISM: artificial
<220> FEATURE:
<223> OTHER INFORMATION: Gp2 phage protein

<400> SEQUENCE: 1

Met Ser Asn Val Asn Thr Gly Ser Leu Ser Val Asp Asn Lys Lys Phe
1               5                   10                  15

Trp Ala Thr Val Glu Ser Ser Glu His Ser Phe Glu Val Pro Ile Tyr
            20                  25                  30

Ala Glu Thr Leu Asp Glu Ala Leu Glu Leu Ala Glu Trp Gln Tyr Val
        35                  40                  45

Pro Ala Gly Phe Glu Val Thr Arg Val Arg Pro Cys Val Ala Pro Lys
    50                  55                  60

<210> SEQ ID NO 2
<211> LENGTH: 110
<212> TYPE: PRT
<213> ORGANISM: artificial
<220> FEATURE:
<223> OTHER INFORMATION: Nun phage protein

<400> SEQUENCE: 2

Met Val Lys Lys Thr Ile Tyr Val Asn Pro Asp Ser Gly Gln Asn Arg
1               5                   10                  15

Lys Val Ser Asp Arg Gly Leu Thr Ser Arg Asp Arg Arg Ile Ala
            20                  25                  30

Arg Trp Glu Lys Arg Ile Ala Tyr Ala Leu Lys Asn Gly Val Thr Pro
        35                  40                  45

Gly Phe Asn Ala Ile Asp Asp Gly Pro Glu Tyr Lys Ile Asn Glu Asp
    50                  55                  60

Pro Met Asp Lys Val Asp Lys Ala Leu Ala Thr Pro Phe Pro Arg Asp
65                  70                  75                  80

Val Glu Lys Ile Glu Asp Glu Lys Tyr Glu Asp Val Met His Arg Val
                85                  90                  95

Val Asn His Ala His Gln Arg Asn Pro Asn Lys Lys Trp Ser
            100                 105                 110

<210> SEQ ID NO 3
<211> LENGTH: 883
<212> TYPE: PRT
<213> ORGANISM: artificial
<220> FEATURE:
<223> OTHER INFORMATION: Gp0.7 phage protein

<400> SEQUENCE: 3

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

-continued

```
Met Ile Ala Arg Ile Asn Asp Trp Phe Glu Glu Val Lys Ala Lys Arg
              85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
            275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Ala Val
        370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495
```

```
Leu Glu Asn Thr Trp Trp Ala Glu Gln Asp Ser Pro Phe Cys Phe Leu
            500             505             510

Ala Phe Cys Phe Glu Tyr Ala Gly Val Gln His His Gly Leu Ser Tyr
            515             520             525

Asn Cys Ser Leu Pro Leu Ala Phe Asp Gly Ser Cys Ser Gly Ile Gln
            530             535             540

His Phe Ser Ala Met Leu Arg Asp Glu Val Gly Gly Arg Ala Val Asn
545             550             555             560

Leu Leu Pro Ser Glu Thr Val Gln Asp Ile Tyr Gly Ile Val Ala Lys
            565             570             575

Lys Val Asn Glu Ile Leu Gln Ala Asp Ala Ile Asn Gly Thr Asp Asn
            580             585             590

Glu Val Val Thr Val Thr Asp Glu Asn Thr Gly Glu Ile Ser Glu Lys
            595             600             605

Val Lys Leu Gly Thr Lys Ala Leu Ala Gly Gln Trp Leu Ala Tyr Gly
            610             615             620

Val Thr Arg Ser Val Thr Lys Arg Ser Val Met Thr Leu Ala Tyr Gly
625             630             635             640

Ser Lys Glu Phe Gly Phe Arg Gln Gln Val Leu Glu Asp Thr Ile Gln
            645             650             655

Pro Ala Ile Asp Ser Gly Lys Gly Leu Met Phe Thr Gln Pro Asn Gln
            660             665             670

Ala Ala Gly Tyr Met Ala Lys Leu Ile Trp Glu Ser Val Ser Val Thr
            675             680             685

Val Val Ala Ala Val Glu Ala Met Asn Trp Leu Lys Ser Ala Ala Lys
            690             695             700

Leu Leu Ala Ala Glu Val Lys Asp Lys Lys Thr Gly Glu Ile Leu Arg
705             710             715             720

Lys Arg Cys Ala Val His Trp Val Thr Pro Asp Gly Phe Pro Val Trp
            725             730             735

Gln Glu Tyr Lys Lys Pro Ile Gln Thr Arg Leu Asn Leu Met Phe Leu
            740             745             750

Gly Gln Phe Arg Leu Gln Pro Thr Ile Asn Thr Asn Lys Asp Ser Glu
            755             760             765

Ile Asp Ala His Lys Gln Glu Ser Gly Ile Ala Pro Asn Phe Val His
            770             775             780

Ser Gln Asp Gly Ser His Leu Arg Lys Thr Val Val Trp Ala His Glu
785             790             795             800

Lys Tyr Gly Ile Glu Ser Phe Ala Leu Ile His Asp Ser Phe Gly Thr
            805             810             815

Ile Pro Ala Asp Ala Ala Asn Leu Phe Lys Ala Val Arg Glu Thr Met
            820             825             830

Val Asp Thr Tyr Glu Ser Cys Asp Val Leu Ala Asp Phe Tyr Asp Gln
            835             840             845

Phe Ala Asp Gln Leu His Glu Ser Gln Leu Asp Lys Met Pro Ala Leu
            850             855             860

Pro Ala Lys Gly Asn Leu Asn Leu Arg Asp Ile Leu Glu Ser Asp Phe
865             870             875             880

Ala Phe Ala
```

```
<210> SEQ ID NO 4
<211> LENGTH: 52
<212> TYPE: PRT
<213> ORGANISM: artificial
```

```
<220> FEATURE:
<223> OTHER INFORMATION: Gp6 phage protein

<400> SEQUENCE: 4

Met Arg Lys Ser Leu Ile Met Gly Thr Lys Glu Asp Val Ala Lys Met
1               5                   10                  15

Lys Ala Lys Arg Gln Met Asn Lys Ala Val Thr Phe Ala Glu Arg Tyr
            20                  25                  30

Ser Thr Ser Glu Pro Val Arg Arg Ile Val Thr Phe Asn His Pro Ala
        35                  40                  45

Ile Lys Gly Met
    50

<210> SEQ ID NO 5
<211> LENGTH: 71
<212> TYPE: PRT
<213> ORGANISM: artificial
<220> FEATURE:
<223> OTHER INFORMATION: Gp8 phage protein

<400> SEQUENCE: 5

Met Glu Gln Leu Asn Tyr Gly Tyr Lys Ile Lys Arg Asn Gln Val Arg
1               5                   10                  15

Gly Ser Trp Leu Phe Leu Val Tyr Gly Lys Pro Ile Tyr Glu Leu His
            20                  25                  30

Arg Gly Glu Lys Ser Lys Thr Tyr Tyr Val Thr His Ile Ala Thr Gly
        35                  40                  45

Lys Thr Pro Ala Cys Ala Gly Leu Leu Arg Asp Ala Ile Met Lys Ala
    50                  55                  60

Cys Met Leu Glu Gly Leu Leu
65                  70

<210> SEQ ID NO 6
<211> LENGTH: 341
<212> TYPE: PRT
<213> ORGANISM: artificial
<220> FEATURE:
<223> OTHER INFORMATION: A* phage protein

<400> SEQUENCE: 6

Met Lys Ser Arg Arg Gly Phe Ala Ile Gln Arg Leu Met Asn Ala Met
1               5                   10                  15

Arg Gln Ala His Ala Asp Gly Trp Phe Ile Val Phe Asp Thr Leu Thr
            20                  25                  30

Leu Ala Asp Asp Arg Leu Glu Ala Phe Tyr Asp Asn Pro Asn Ala Leu
        35                  40                  45

Arg Asp Tyr Phe Arg Asp Ile Gly Arg Met Val Leu Ala Ala Glu Gly
    50                  55                  60

Arg Lys Ala Asn Asp Ser His Ala Asp Cys Tyr Gln Tyr Phe Cys Val
65                  70                  75                  80

Pro Glu Tyr Gly Thr Ala Asn Gly Arg Leu His Phe His Ala Val His
                85                  90                  95

Phe Met Arg Thr Leu Pro Thr Gly Ser Val Asp Pro Asn Phe Gly Arg
            100                 105                 110

Arg Val Arg Asn Arg Arg Gln Leu Asn Ser Leu Gln Asn Thr Trp Pro
        115                 120                 125

Tyr Gly Tyr Ser Met Pro Ile Ala Val Arg Tyr Thr Gln Asp Ala Phe
    130                 135                 140
```

-continued

```
Ser Arg Ser Gly Trp Leu Trp Pro Val Asp Ala Lys Gly Glu Pro Leu
145             150             155             160

Lys Ala Thr Ser Tyr Met Ala Val Gly Phe Tyr Val Ala Lys Tyr Val
                165             170             175

Asn Lys Lys Ser Asp Met Asp Leu Ala Ala Lys Gly Leu Gly Ala Lys
            180             185             190

Glu Trp Asn Asn Ser Leu Lys Thr Lys Leu Ser Leu Leu Pro Lys Lys
            195             200             205

Leu Phe Arg Ile Arg Met Ser Arg Asn Phe Gly Met Lys Met Leu Thr
        210             215             220

Met Thr Asn Leu Ser Thr Glu Cys Leu Ile Gln Leu Thr Lys Leu Gly
225             230             235             240

Tyr Asp Ala Thr Pro Phe Asn Gln Ile Leu Lys Gln Asn Ala Lys Arg
            245             250             255

Glu Met Arg Leu Arg Leu Gly Lys Val Thr Val Ala Asp Val Leu Ala
            260             265             270

Ala Gln Pro Val Thr Thr Asn Leu Leu Lys Phe Met Arg Ala Ser Ile
        275             280             285

Lys Met Ile Gly Val Ser Asn Leu Gln Ser Phe Ile Ala Ser Met Thr
        290             295             300

Gln Lys Leu Thr Leu Ser Asp Ile Ser Asp Glu Ser Lys Asn Tyr Leu
305             310             315             320

Asp Lys Ala Gly Ile Thr Thr Ala Cys Leu Arg Ile Lys Ser Lys Trp
            325             330             335

Thr Ala Gly Gly Lys
            340

<210> SEQ ID NO 7
<211> LENGTH: 69
<212> TYPE: PRT
<213> ORGANISM: artificial
<220> FEATURE:
<223> OTHER INFORMATION: Bacillus subtilis YkzG (Epsilon-Subunit)

<400> SEQUENCE: 7

Met Ile Tyr Lys Val Phe Tyr Gln Glu Lys Ala Asp Glu Val Pro Val
1               5               10              15

Arg Glu Lys Thr Asp Ser Leu Tyr Ile Glu Gly Val Ser Glu Arg Asp
            20              25              30

Val Arg Thr Lys Leu Lys Glu Lys Lys Phe Asn Ile Glu Phe Ile Thr
        35              40              45

Pro Val Asp Gly Ala Phe Leu Glu Tyr Glu Gln Gln Ser Glu Asn Phe
        50              55              60

Lys Val Leu Glu Leu
65

<210> SEQ ID NO 8
<211> LENGTH: 350
<212> TYPE: PRT
<213> ORGANISM: artificial
<220> FEATURE:
<223> OTHER INFORMATION: Bacillus phage SPO1 GP40

<400> SEQUENCE: 8

Met His Ile Tyr Thr Tyr Trp Gly Leu Lys Tyr Val Pro Ser Asn Ser
1               5               10              15

Thr Met Val Ala Lys Glu Gly Asp Leu Ile Leu Leu Gly Asn Glu Val
            20              25              30
```

-continued

```
His Lys Val Val Lys Val Leu His Arg Phe Arg Asn Ile Thr Asp Leu
        35              40                  45

Gln Ile Thr Asn Trp Lys Gly Thr Glu Thr Arg Tyr Asn Leu His Val
    50              55                  60

Thr Glu Tyr Lys Val Leu Val Pro Tyr Asp Thr His Lys Glu Glu Asn
65              70              75                  80

Glu Ala Met Ser Asp Ser Leu Ile Thr His Asn Gly Lys Asp Tyr Val
            85              90                  95

Leu Cys Lys Ile Pro Ala Arg Val Gly Asp Leu Ile Arg Thr Glu Asp
            100             105                 110

Lys Arg Val Trp Glu Val Leu Gln Lys Ser Lys Asp Gly Leu Val Leu
        115                 120                 125

Tyr Asn Glu Glu Lys Gly Glu Gln Arg Ser Ala Val Tyr Ser Glu Ile
    130                 135                 140

Gly Pro Tyr His Val Leu Val Pro Arg Asp Thr Asp Thr His Thr Pro
145             150                 155                 160

Thr Arg Glu Glu Leu Ala Ala Val Ile Met Asn Lys Ala Phe Thr Arg
            165                 170                 175

Thr Glu Thr Gln Asp Ser Gln Glu Asp Thr Gly Thr His Lys Gly Leu
            180                 185                 190

Gly Leu Thr Gly Thr Asp Leu Tyr His Ser Leu Arg Asp Leu Asp Ala
        195                 200                 205

Lys Val Gln Ser Gly Tyr Tyr Thr Ala Thr Glu Asn Glu Glu Asp Val
    210                 215                 220

Lys Ser Glu Ile Glu Ala Thr Lys Lys His Met Lys Ala Val Lys Glu
225                 230                 235                 240

Ser Gly Lys Thr Val Asn Asp Tyr Arg Lys Glu Glu Asn Thr Lys Arg
            245                 250                 255

Cys Lys Leu Lys Ala Leu Thr Asn Lys Phe Asn Arg Leu Phe Leu Lys
            260                 265                 270

Ser Val Ile Asp Thr Asp Ser Leu Gln Val Gly Lys Ala Tyr Leu Ile
        275                 280                 285

Gly Gly Arg Asp Met Lys Asn Val His Gly Leu Tyr Thr Gly Thr Thr
    290                 295                 300

Phe Asp Gln Gln His Ala Asn Phe Leu Ile Val Glu Thr Asp Arg Met
305                 310                 315                 320

His Arg Thr Leu Thr Val Ser Ala Glu Gln Leu Phe Ala Glu Glu Arg
            325                 330                 335

His Ile Val Asp Ile Glu Lys Arg Val Glu Gln Thr Glu Asp
        340                 345                 350

<210> SEQ ID NO 9
<211> LENGTH: 202
<212> TYPE: PRT
<213> ORGANISM: artificial
<220> FEATURE:
<223> OTHER INFORMATION: Staphylococcus phage G1 GP67

<400> SEQUENCE: 9

Met Thr Asn Ser Lys Lys Lys Gly Asp Thr Phe Glu Arg Lys Ile Ala
1               5                   10                  15

Lys Glu Leu Thr Ala Trp Trp Gly Tyr Gln Phe Asn Arg Ser Pro Gln
            20                  25                  30

Ser Gly Gly Ala Ser Trp Gly Lys Asp Asn Asn Ala Val Gly Asp Ile
        35                  40                  45
```

-continued

```
Val Val Pro Gln Glu Ala Asn Phe Pro Leu Val Val Glu Cys Lys His
    50              55                  60

Arg Glu Glu Trp Thr Ile Asp Asn Val Leu Leu Asn Asn Arg Glu Pro
65                  70                  75                  80

His Thr Trp Trp Glu Gln Val Ile Asn Asp Ser Ser Lys Val Asn Lys
                85                  90                  95

Thr Pro Cys Leu Ile Phe Thr Arg Asn Arg Ala Gln Ser Tyr Val Ala
            100             105             110

Leu Pro Tyr Asp Glu Lys Val Tyr Glu Asp Leu Arg Asn Asn Glu Tyr
        115             120             125

Pro Val Met Arg Thr Asp Phe Ile Ile Asp Asn Ile Arg Lys Asp Lys
    130             135             140

Phe Phe Tyr Asp Val Leu Ile Thr Thr Met Asn Gly Leu Thr Ser Phe
145             150             155             160

Thr Pro Ser Tyr Ile Ile Ser Cys Tyr Asp Lys Lys Asp Ile Lys Pro
            165             170             175

Tyr Lys Lys Val Glu Ser Asn Leu Ser Glu Val Ser Lys His Glu Asp
            180             185             190

Glu Leu Ile Asn Asp Leu Leu Ser Asp Ile
        195             200

<210> SEQ ID NO 10
<211> LENGTH: 141
<212> TYPE: PRT
<213> ORGANISM: artificial
<220> FEATURE:
<223> OTHER INFORMATION: Thermus thermophilus phage P23-45 GP39

<400> SEQUENCE: 10

Met Val Glu Gly Phe Val Glu Pro Tyr Ile Arg Leu Phe Glu Ala Ile
1               5                   10                  15

Pro Asp Ala Glu Thr Glu Leu Ala Thr Phe Tyr Asp Ala Asp Leu Asp
                20                  25                  30

Thr Leu Pro Pro Arg Met Phe Leu Pro Ser Gly Asp Leu Tyr Thr Pro
            35                  40                  45

Pro Gly Pro Val Arg Leu Glu Glu Ile Lys Arg Lys Arg Val Arg
    50              55                  60

Leu Val Lys Val Ser Ile Tyr Arg Phe Glu His Val Gly Leu Gly Leu
65                  70                  75                  80

Ala Ala Arg Pro Tyr Ala Tyr Ala Tyr Ala Trp Gln Gly Asp Asn Gly
                85                  90                  95

Ile Leu His Leu Tyr His Ala Pro Val Val Leu Glu Asp Val Pro Glu
            100             105             110

Val Leu Glu Leu Asp Glu Val Thr Tyr Asn Glu Ser Tyr Val Arg Leu
        115             120             125

Met Arg Ala Met Gly His Val Asp Ala Phe Ile Asp Leu
    130             135             140

<210> SEQ ID NO 11
<211> LENGTH: 82
<212> TYPE: PRT
<213> ORGANISM: artificial
<220> FEATURE:
<223> OTHER INFORMATION: Enterobacteria phage PhiEco32 GP79

<400> SEQUENCE: 11

Met Asp Met Phe Ser Leu Glu Asp Leu Val Gln Asn Gly Met Met Glu
```

-continued

```
1               5                   10                  15

Gln Lys Glu Pro Leu Ile Val Gly Ser Arg Lys Glu Leu Arg Lys Leu
                20                  25                  30

Cys Glu Glu Trp Gly Ile Thr Asn Gln Arg Met Ile Gly Asn Gln Phe
            35                  40                  45

Ser Ala Ile Val Thr Phe Leu Lys Arg Gly Asp Lys Tyr Ser Met Glu
        50                  55                  60

Cys Val Glu Arg Ile Ile Thr Glu Ala Gln Gln Asp Lys Gly Val Thr
65                  70                  75                  80

Tyr Leu

<210> SEQ ID NO 12
<211> LENGTH: 73
<212> TYPE: PRT
<213> ORGANISM: artificial
<220> FEATURE:
<223> OTHER INFORMATION: Xanthomonas oryzae bacteriophage Xp10 P7

<400> SEQUENCE: 12

Met Asn Glu Phe Thr Gln Ile Ser Gly Tyr Val Asn Ala Phe Gly Ser
1               5                   10                  15

Gln Arg Gly Ser Val Leu Thr Val Lys Val Glu Asn Asp Glu Gly Trp
                20                  25                  30

Thr Leu Val Glu Glu Asp Phe Asp Arg Ala Asp Tyr Gly Ser Asp Pro
            35                  40                  45

Glu Phe Val Ala Glu Val Ser Ser Tyr Leu Lys Arg Asn Gly Gly Ile
        50                  55                  60

Lys Asp Leu Thr Lys Val Leu Thr Arg
65                  70

<210> SEQ ID NO 13
<211> LENGTH: 167
<212> TYPE: PRT
<213> ORGANISM: artificial
<220> FEATURE:
<223> OTHER INFORMATION: Enterobacteria phage T4 Alc

<400> SEQUENCE: 13

Met Asp Leu Gln Leu Ile Thr Thr Glu Met Val Val Glu Ala Tyr Gly
1               5                   10                  15

Asp Thr Thr Asp Gly Ile Ser Val Phe Lys Gly Asn Arg Arg Val Gly
                20                  25                  30

Tyr Ile Thr Gly Leu Lys Lys Asp Leu Ala Lys Gln Val Lys Arg Lys
            35                  40                  45

Thr Thr Ile Lys Glu Tyr Arg Asn Arg Arg Leu Glu Gln Ala Arg Asp
        50                  55                  60

Met Leu Pro Asp Ala Val Glu Glu Met Lys Val Phe Leu Glu Asn Gln
65                  70                  75                  80

Leu Ala Lys Tyr Asp Cys Glu Val Phe Ile Asn Gln Thr Gln Pro Asn
                85                  90                  95

Val His Ile Asn Ser Cys Lys Cys Tyr Ile Ile Val Asn Pro Leu Thr
                100                 105                 110

Gly Lys His Arg Leu Gly Ile Ser Asn Pro Asn Arg Ser Ala Ser Asp
            115                 120                 125

Met Ala Glu Asp Val Glu Ala Cys Phe Lys Ile Ser Lys Ser Pro Ala
        130                 135                 140

Glu His His Ile Leu Ile Asn Gly Leu Ser Gln Asp Asp Ile Val Glu
```

-continued

```
145              150              155              160

Val Ile Lys Thr Leu Cys Met
                    165

<210> SEQ ID NO 14
<211> LENGTH: 90
<212> TYPE: PRT
<213> ORGANISM: artificial
<220> FEATURE:
<223> OTHER INFORMATION: Enterobacteria phage T4 Asia

<400> SEQUENCE: 14

Met Asn Lys Asn Ile Asp Thr Val Arg Glu Ile Ile Thr Val Ala Ser
1               5                   10                  15

Ile Leu Ile Lys Phe Ser Arg Glu Asp Ile Val Glu Asn Arg Ala Asn
            20                  25                  30

Phe Ile Ala Phe Leu Asn Glu Ile Gly Val Thr His Glu Gly Arg Lys
        35                  40                  45

Leu Asn Gln Asn Ser Phe Arg Lys Ile Val Ser Glu Leu Thr Gln Glu
    50                  55                  60

Asp Lys Lys Thr Leu Ile Asp Glu Phe Asn Glu Gly Phe Glu Gly Val
65                  70                  75                  80

Tyr Arg Tyr Leu Glu Met Tyr Thr Asn Lys
            85                  90

<210> SEQ ID NO 15
<211> LENGTH: 714
<212> TYPE: DNA
<213> ORGANISM: Artificial
<220> FEATURE:
<223> OTHER INFORMATION: GFPmut3.1

<400> SEQUENCE: 15
atgagtaaag gggaagaact atttacaggt gtggtcccga ttctcgtgga attggacggt      60
gacgtgaatg gacataaatt ttccgtcagt ggcgagggtg agggtgatgc aacttacgga     120
aagctaacat tgaagttcat ttgtacaact ggcaaacttc ctgttccgtg gcctacgctt     180
gtcaccacat tcggctacgg cgtacagtgc ttcgcacggt acccagacca catgaagcag     240
catgactttt ttaaatccgc tatgcctgaa gggtacgtcc aggagaggac gatcttcttc     300
aaggatgacg gtaactataa acccgagct gaagtgaaat tcgaggggga caccctagtt      360
aaccgaatag agcttaaagg aatagacttc aaagaggacg ggaacatctt aggccataag     420
ctggaatata ctataattc acacaacgtg tacattatgg cggataagca aaaaaacggt      480
ataaaggtaa acttcaaaat tcgccataac atcgaagacg gtcggttca acttgctgac      540 cactaccagc agaataccc gattggcgac ggccccgtat tactccccga caaccattat     600
ttgagtacgc aatccgccct ctctaaagac ccgaatgaga agcgtgatca tatggtttta    660
ttagaatttg ttacggcggc gggaataact cacggcatgg atgaactgta caaa           714

<210> SEQ ID NO 16
<211> LENGTH: 978
<212> TYPE: DNA
<213> ORGANISM: Artificial
<220> FEATURE:
<223> OTHER INFORMATION: PelB-SpA

<400> SEQUENCE: 16
atgaaatacc tgcttccgac cgctgctgct ggtctgctgc tcctcgctgc ccagccggcg      60
```

-continued

```
atggcggcac agcatgatga agctcagcag aacgctttct accaagtgct taacatgccg       120
aacttgaacg cggaccagcg taatggcttc attcaatcac tgaaggacga cccttcccaa       180
tcagctaatg tccttggaga ggcgcagaaa ttaaatgact ctcaagcgcc caaagcagac       240
gcccagcaaa ataattttaa taaggatcaa cagtcagcat tctacgaaat tcttaacatg       300
ccaaatttaa acgaagcaca acgtaacggt ttcattcaat cgctgaaaga tgatcccagt       360
caatcgacaa atgtacttgg tgaagcgaaa aaacttaacg agtcgcaagc tccaaaagcg       420
gacaacaact tcaataagga gcagcagaat gctttctatg agattctgaa tatgccgaat       480
ctgaacgaag agcagcgcaa cggctttatc cagtccttga aggacgaccc cagccaaagc       540
gctaacctgt tgtcagaagc taaaaaactt aatgagtcac aagctccaaa ggcagacaat       600
aagttcaaca aggaacagca gaacgctttt tatgagattc ttcacctgcc gaatttaaat       660
gaagagcaac gcaatggttt tatccaatcg ttaaaagatg atccttcgca atcagcgaac       720
cttttggccg aagcaaaaaa gttaaacgac gcccaagcgc ccaaggcaga caacaagttt       780
aataaagaac aacaaatgc gttttacgaa attttgcacc ttccgaactt aacagaagag       840
cagcgtaatg ggttcatcca gtctttgaag gatgacccat ccgtctcaaa agagattctt       900
gctgaggcta agaagttgaa tgatgcacag gcgccgaagg aagaggactc tttggagcat       960
catcaccacc accactaa                                                     978
```

<210> SEQ ID NO 17
<211> LENGTH: 69
<212> TYPE: PRT
<213> ORGANISM: Artificial
<220> FEATURE:
<223> OTHER INFORMATION: T7 phage Gp5.7

<400> SEQUENCE: 17

```
Met Ser Asp Tyr Leu Lys Val Leu Gln Ala Ile Lys Ser Cys Pro Lys
1               5                   10                  15

Thr Phe Gln Ser Asn Tyr Val Arg Asn Asn Ala Ser Leu Val Ala Glu
            20                  25                  30

Ala Ala Ser Arg Gly His Ile Ser Cys Leu Thr Thr Ser Gly Arg Asn
        35                  40                  45

Gly Gly Ala Trp Glu Ile Thr Ala Ser Gly Thr Arg Phe Leu Lys Arg
    50                  55                  60

Met Gly Gly Cys Val
65
```

<210> SEQ ID NO 18
<211> LENGTH: 1119
<212> TYPE: DNA
<213> ORGANISM: Corynebacterium glutamicum

<400> SEQUENCE: 18

```
atggacaatg gcatgacaat caccacagaa cattcaactc atcctgatct tgatttcaat        60
gatgagattt atcgggaact aaaccgcatc tgcgcttcgc tatctcaaca gtgcagcaca       120
tatcaaccag agttccgtac ctgcctagat gctgctttcc aagctttgcg aggtggcaag       180
ttaatccgcc ctcgaatgct actggggcta tacaacacgt tgtagacga tgacattgag        240 gtcaaactca acaccgtttt acaggtagca gtggctttag aactactgca ttttttccctt       300 ttggttcatg acgatgttat tgacggagac ctctatcgcc gaggcaaact taattttatt       360
gggcagattc tcatgcatcg cacacctgaa agttttgcac aaatccagcg cgatccagag       420
```

```
catctagatt gggcacaatc taatggactg cttatgggaa atcttttct tgctgccacc        480 catcaaatct tcgcgcgcct tgaccttcca catcaccaac gggttcgact tttagattta        540
ctcaaccaca cgataaatga cactattgtg ggtgagtttc ttgatgtggg attaagcagc        600
aaagccatca gccccaatat ggacattgct ctagaaatga gtcggctaaa aacagccaca        660
tacacttttg aacttccaat gagagcagcg gcaattctcg cggaactacc tcaggagatt        720
gaaacaaaga taggtgagat aggcacaaac ttgggcatcg cttatcaatt gcaggacgat        780
tacttatcta cttttggtga cgcagccgaa cacggcaaag atgccttttc tgaccttcga        840
gaaggaaaag aaactacaat tatcgccttc gctcgagata ctgctaaatg gactgatatt        900
caagacaact tcggctccgc agatctgagc acctctcagg cagagcgaat tcaacatctt        960
ctcatacagt gtggagcaaa gaatcactcc ttgaatgcca tctccgacca cttaaatatc       1020
tgccgttcga tgatcaaaac actaagcccc caggtagatc ccaaggctca aaatttatta       1080
cttaaacaag ttgagcaact agccagccgc aaatcttag                             1119
```

```
<210> SEQ ID NO 19
<211> LENGTH: 915
<212> TYPE: DNA
<213> ORGANISM: Corynebacterium glutamicum

<400> SEQUENCE: 19
atgacacacc aaaattcgcc tctcttcctt aaaagtgcac tgagacttta caatcgggcc         60
tcattcaagg cttcacataa agtgatcgaa gaatattcga cgagcttcag tctgtctacg        120
tggttgctat ccccacgcat acgaaatgac atacgaaatc tctatgcagt agttcgtatc        180
gccgatgaga ttgtcgacgg cactgcacat gccgctggtt gctcaactgc caaaatcgaa        240
gagattctcg atgcctatga aattgcggtt cttgcagcac cacaacaacg cttcaacaca        300
gatcttgttt tacaagctta tggtgaaact gcccgacgct gtgatttcga acaagagcat        360
gtaatagcct tctttgcatc aatgcgtaag gacctcaaag ctaatacaca cgacccagat        420
agcttcacaa cgtatgtcta tggctccgcg gaagttatag gcctgctttg tctcagcgtt        480
ttcaaccaag gtagaacgat tagcaaaaaa cggctagaga ttatgcaaaa cggagcccgc        540
tcattgggag cggcattcca gaaaattaac tttctccgtg acttggcaga agatcagcaa        600
aatttgggcc gatttattt ccccaaaacc agccaaggaa ctcttactaa agaacaaaaa        660
gaagatctca tcgctgatat ccgtcaagac ctagcaattg cccacgatgc atttccagaa        720
ataccagtgc aggctcgcat cggagtgatc tctgcttatt tgctctttca aaaactcact        780
gaccgaattg aggctactcc taccgccgat ttattgcggg agcgaatcag agttccactt        840
catatcaaac tctctacact cgctagagcc acgatgaaag gtctatctat gagcatctac        900
agaaagaatt cgtga                                                        915
```

```
<210> SEQ ID NO 20
<211> LENGTH: 784
<212> TYPE: DNA
<213> ORGANISM: Corynebacterium glutamicum

<400> SEQUENCE: 20
aattcgtgag ctgggagttc gtagacggaa acaaacgcag aatccaagcg aaggagatat         60
acatgtgatg aaggtctcga ctaaaactcc acgctcctca ggtaccgccg tagtcatagg        120
cgcaggtgtt gctggtttag ccacttctgc acttttagca cgtgatggct ggcaagtaac        180
tgttttggaa aaaaatactg atgtcggtgg ccgagctgga tcgcttgaaa tatcaggctt        240
```

-continued

```
tcctggcttt cgatgggata ccggaccttc ttggtacctc atgcccgagg cctttgacca    300
tttcttcgca ctttttggtg catgtacttc tgattatctc gatttggtag aattaacgcc    360
tggttatcga gttttttctg gcacacatga cgctgtcgat gtccccactg ggcgtgaaga    420
agcaattgcg ctattcgaat ccatcgaacc cggcgcgggt gcaaaactag gaaattatct    480
tgatagcgcg gcagacgcct atgacattgc cattgataga ttcctttata ataatttctc    540
cacgttaggc ccgctgcttc accgggatgt actgacccga gctggccgac tgttttctct    600
actgacccgt tctttacaaa agtacgtaaa tagtcaattc agtagcccgg tgttgcgcca    660
gatcctaacc tatccagcag tcttcctgtc ttcccgaccc actactaccc catcgatgta    720
ccacttgatg agtcataccg atttggtgca gggagtgaaa taccctatag gtggttttac    780
tgca                                                                 784
```